(12) United States Patent
Allgeier et al.

(10) Patent No.: US 8,299,085 B2
(45) Date of Patent: Oct. 30, 2012

(54) QUINAZOLINE DERIVATIVES

(75) Inventors: Hans Allgeier, Loerrach (DE);
Wolfgang Froestl, Ecublens (CH);
Manuel Koller, Schliern (CH); **Henri
Mattes, Brunstatt (FR); Joachim
Nozulak, Heitersheim (DE); Silvio
Ofner, Muenchenstein (CH); David
Orain, Hesingue (FR); Vittorio Rasetti**,
Riehen (CH); Johanne Renaud, Basel
(CH); Nicolas Soldermann, Rosenau
(FR); Philipp Floersheim, Basel (CH)

(73) Assignee: Novartis AG, Basel (CH)

( * ) Notice: Subject to any disclaimer, the term of this patent is extended or adjusted under 35 U.S.C. 154(b) by 1518 days.

(21) Appl. No.: 11/572,007

(22) PCT Filed: Jul. 26, 2005

(86) PCT No.: PCT/EP2005/008113
§ 371 (c)(1),
(2), (4) Date: Feb. 27, 2007

(87) PCT Pub. No.: WO2006/010591
PCT Pub. Date: Feb. 2, 2006

(65) Prior Publication Data
US 2007/0208018 A1 Sep. 6, 2007

(30) Foreign Application Priority Data
Jul. 27, 2004 (GB) .................................. 0416730.0

(51) Int. Cl.
*A01N 43/54* (2006.01)
*A61K 31/517* (2006.01)
(52) U.S. Cl. ..................................... 514/266.3; 544/285
(58) Field of Classification Search ................ 514/266.3; 544/285
See application file for complete search history.

(56) References Cited

U.S. PATENT DOCUMENTS

| | | | |
|---|---|---|---|
| 6,562,839 | B1 | 5/2003 | Takano et al. |
| 7,247,610 | B2 | 7/2007 | Ikonomidou |
| 2003/0153584 | A1 | 8/2003 | Weaver et al. |
| 2006/0128645 | A1 | 6/2006 | Ozawa et al. |
| 2008/0153836 | A1 | 6/2008 | Allgeier et al. |
| 2010/0144747 | A1* | 6/2010 | Allgeier et al. .......... 514/252.02 |

FOREIGN PATENT DOCUMENTS

| | | |
|---|---|---|
| DE | 196 50 975 A1 | 6/1998 |
| EP | 1 452 530 A1 | 9/2004 |
| EP | 1 491 211 A1 | 12/2004 |
| WO | WO 93/10783 A2 | 6/1993 |
| WO | WO 93/24442 A1 | 12/1993 |
| WO | 95/19346 | 7/1995 |
| WO | WO 9519346 A1 * | 7/1995 |
| WO | WO 96/04288 A1 | 2/1996 |
| WO | WO 97/07799 A1 | 3/1997 |
| WO | WO 97/40017 A2 | 10/1997 |
| WO | WO 98/11892 A1 | 3/1998 |
| WO | WO 98/38187 A1 | 9/1998 |
| WO | WO 98/50036 A1 | 11/1998 |
| WO | WO 01/53273 A1 | 7/2001 |
| WO | WO 03/000928 A2 | 1/2003 |
| WO | WO 2004/028634 A1 | 4/2004 |
| WO | WO 2004/058679 A2 | 7/2004 |
| WO | WO 2004/058704 A2 | 7/2004 |
| WO | WO 2004/067524 A1 | 8/2004 |
| WO | WO 2005/030217 A1 | 4/2005 |
| WO | WO 2005/033311 A2 | 4/2005 |
| WO | WO 2006/010591 A2 | 2/2006 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
Hans Allgeier, U.S. PTO Office Action, U.S. Appl. No. 12/569,402, Oct. 14, 2010, 10 pgs.
Hans Allgeier, U.S. PTO Ex Parte Quayle Action, U.S. Appl. No. 12/569,402, Jan. 20, 2011, 13 pgs.
Hans Allgeier, U.S. PTO Notice of Allowance, U.S. Appl. No. 12/569,402, Mar. 31, 2011, 12 pgs.
Chilean Office Action, CL Application No. 809-06, Jan. 28, 2011 and English translation thereof, 10 pgs.
Hans Allgeier, U.S. PTO Notice of Allowance, U.S. Appl. No. 11/911,040, Dec. 1, 2009, 13 pgs.
Hans Allgeier, U.S. PTO Notice of Allowance, U.S. Appl. No. 11/911,040, Sep. 4, 2009, 10 pgs.
Singapore Office Action, Patent App. No. 200706385-2, Oct. 5, 2009, 8 pgs.
Hans Allgeier, U.S. PTO Notice of Allowance, U.S. Appl. No. 12/569,402, Jul. 6, 2011, 9 pgs.
Indian Office Action, Jul. 27, 2011, 3 pgs.

(Continued)

*Primary Examiner* — James O Wilson
*Assistant Examiner* — Alexander R Pagano
(74) *Attorney, Agent, or Firm* — Paul D. Strain, Esq.; Strain & Strain PLLC

(57) ABSTRACT

The present invention relates to 1H-Quinazoline-2,4-dione derivatives of formula(I)

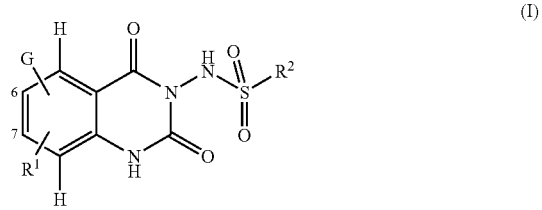

wherein the substituents are defined as in the specification, their preparation, their use as pharmaceuticals, and pharmaceutical compositions containing them.

6 Claims, No Drawings

OTHER PUBLICATIONS

Allgeier, U.S. PTO Restriction Requirement, U.S. Appl. No. 13/192,816, May 10, 2012, 12 pgs.

Takano et al., "Synthesis and AMPA Receptor Antagonistic Activity of a Novel Class of Quinoxalinecarboxylic Acid with a Substituted Phenyl Group at the C-7 Position", Bioorganic & Medicinal Chemistry Letters, vol. 13 (2003), pp. 3521-3525.

Ohmori et al., "6-(1H-Imidazol-1-yl)-7-nitro-2,3(1H,4H)-quinoxalinedione Hydrochloride (YM90K) and Related Compounds: Structure-Activity Relationships for the AMPA-Type Non-NMDA Receptor", J. Med. Chem., vol. 37 (1994), pp. 467-475.

Colotta et al., "3-Hydroxy-quinazoline-2,4-dioe as a useful scaffold to obtain selective Gly/NMDA and AMPA receptor antagonists", Bioorg. Med. Chem. Lett., XP-002389894, vol. 14 (2004), pp. 2345-2349.

Jörg Striessnig, "Pathophysiology of migraine headache: Insight from pharmacology and genetics", Drug Discovery Today, vol. 2, No. 4 (2005), pp. 453-462.

Hans Allgeier, U.S. PTO Office Action, U.S. Appl. No. 11/911,040, Jan. 27, 2009, 8 pgs.

Catarzi et al., "Synthesis and Biological Evaluation of Analogues of 7-Chloro-4,5-dihydro-4-oxo-8-(1,2,4-triazol-4-yl)-1,2,4-triazolo[1,5-a]quinoxaline-2-carboxylic Acid (TQX-173) as Novel Selective AMPA Receptor Antagonists", J. Med. Chem. vol. 47, No. 1 (2004), pp. 262-272.

Hans Allgeier, U.S. PTO Office Action, U.S. Appl. No. 11/911,040, May 29, 2009, 11 pgs.

Hans Allgeier, U.S. PTO Office Action (Interview Summary), U.S. Appl. No. 11/911,040, Jul. 23, 2009, 4 pgs.

Allgeier, U.S. PTO Office Action, U.S. Appl. No. 13/192,816, Aug. 22, 2012, 23 pgs.

* cited by examiner

QUINAZOLINE DERIVATIVES

The present invention relates to 1H-Quinazoline-2,4-diones, their preparation, their use as pharmaceuticals, and pharmaceutical compositions containing them.

In particular the present invention provides compounds of formula (I)

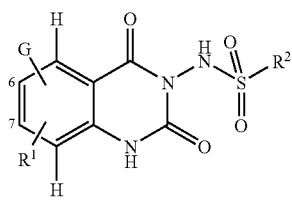

wherein
G is $NR^3R^4$ or $OR^5$, wherein
  $R^3$, $R^4$ and $R^5$ are independently hydrogen, aryl, aralkyl, acyl or alkyl optionally substituted by aryl, heterocyclyl, aryloxy, aralkyloxy or alkoxycarbonylamino, or
  $R^3$ and $R^4$ together with the adjacent nitrogen atom form heteroaryl or heterocyclyl containing at least one nitrogen ring atom and attached via this nitrogen ring atom, wherein heteroaryl and heterocyclyl are optionally substituted by aryl, aralkyl, aryloxyalkyl, aminocarbonylalkyl, mono- or dialkyl aminocarbonylalkyl or morpholinocarbonylalkyl,
$R^1$ is nitro or trifluoromethyl, and
$R^2$ is alkyl, aryl or aralkyl,
and their salts.

As indicated above alkyl, heteroaryl and heterocyclyl are optionally substituted, preferably unsubstituted, mono-, di-, or trisubstituted with said substituents, more preferably unsubstituted or monosubstituted with said substituents.

Unless indicated otherwise, the expressions used in this invention have the following meaning:

Acyl is alkylcarbonyl, arylcarbonyl or aralkylcarbonyl.

Alkyl is linear, branched or cyclic, saturated or unsaturated, preferably saturated, alkyl, preferably $(C_1-C_8)$-alkyl, more preferably $(C_1-C_6)$-alkyl, most preferably $(C_1-C_4)$-alkyl. Alkyl is optionally substituted by one or more substituents, preferably one to three substituents. The substituents are preferably halogen, hydroxyl, cyano, $(C_1-C_4)$-alkoxy, $(C_1-C_4)$-alkoxycarbonyl, amino, $(C_1-C_4)$-alkylamino, di-$(C_1-C_4)$-alkylamino, $(C_1-C_4)$-alkoxycarbonylamino, or $(C_1-C_4)$-alkylcarbonylamino.

Alkane (e.g. in alkanesulfonyl) and alk (e.g. in alkoxy) are defined analogously to Alkyl, especially regarding linearity, saturation, preferential size, and optional substitution.

Aryl is preferably phenyl, naphthyl or 5- to 10-membered heteroaryl, more preferably phenyl or 5- to 6-membered heteroaryl. Aryl is optionally substituted, preferably un-, mono-, di- or trisubstituted. Substituents are preferably halogen, more preferably fluorine or chlorine, nitro, cyano, formyl, carboxamido, hydroxyl, amino, $(C_1-C_4)$-alkylamino, di-(CI-$C_4$)-alkylamino, $(C_1-C_4)$-alkyl, $(C_1-C_4)$-alkoxy, $(C_1-C_4)$-alkoxycarbonyl, $(C_1-C_4)$-alkanesulfonyl, $(C_1-C_4)$-alkyl-carbonyl, $(C_1-C_4)$-alkoxycarbonylamino, or $(C_1-C_4)$-alkylcarbonylamino.

Aralkyl is alkyl substituted by aryl.

Halogen is preferably bromine, chlorine or fluorine.

Heteroaryl is a mono- or polycyclic, preferably mono- or bicyclic, most preferably monocylic aromatic residue containing one or more, preferably one to three hetero ring atoms preferably selected from nitrogen, oxygen, and sulfur, most preferably nitrogen. Heteroaryl is preferably 5- to 10-membered heteroaryl, more preferably 5- to 6-membered heteroaryl. Heteroaryl is optionally substituted, preferably un-, mono-, di- or trisubstituted. Substituents are preferably halogen, more preferably fluorine or chlorine, nitro, cyano, formyl, carboxamido, hydroxyl, amino, $(C_1-C_4)$-alkylamino, di-$(C_1-C_4)$-alkylamino, $(C_1-C_4)$-alkyl, $(C_1-C_4)$-alkoxy, $(C_1-C_4)$-alkoxycarbonyl, $(C_1-C_4)$-alkanesulfonyl, $(C_1-C_4)$-alkyl-carbonyl, $(C_1-C_4)$-alkoxycarbonylamino, or $(C_1-C_4)$-alkylcarbonylamino.

Heterocycl is a mono- or polycyclic, preferably mono- or bicyclic, most preferably monocylic, saturated or partially unsaturated cyclic residue containing three or more ring atoms, preferably three to ten ring atoms, of which one or more, preferably one to three are hetero atoms preferably selected from nitrogen, oxygen, and sulfur. Heterocyclyl is optionally substituted, preferably by halogen, cyano, carboxamido, hydroxyl, amino, $(C_1-C_4)$-alkylamino, di-$(C_1-C_4)$-alkylamino, $(C_1-C_4)$-alkyl, $(C_1-C_4)$-alkoxy, $(C_1-C_4)$-alkoxycarbonyl, $(C_1-C_4)$-alkyl-carbonyl, $(C_1-C_4)$-alkoxycarbonylamino, or $(C_1-C_4)$-alkylcarbonylamino.

Salts are preferably physiologically acceptable salts, formed, as applicable, by the addition of an acid or base.

The said optional substituents listed for Alkyl, Aryl, Heteroaryl, and Heterocyclyl in the Definitions are to be understood as substituents in addition to those listed in the general formulae, i.e. e.g. Alkyl can bear substituents listed in a general formula and/or in the Definitions.

The tautomeric forms of the compounds of formula I are also embraced by the invention. In those compounds, where there is one or more asymmetric atom, esp. carbon atom, the compounds exist in individual, optically active isomeric forms or as mixtures thereof, e.g. as racemic or diastereomeric mixtures. The present invention embraces individual optically active isomers as well as mixtures, e.g. racemic or diastereomeric mixtures, thereof.

Preference is given to compounds of formula (Ia)

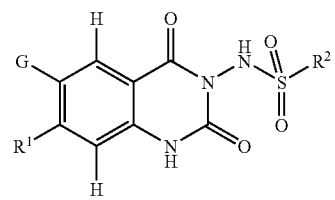

wherein R1, G and R2 are as defined in this specification.

Further preference is given to of compounds formula (Ib)

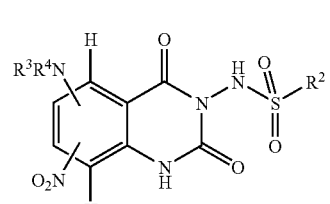

wherein $R^2$, $R^3$, and $R^4$ are as defined in this specification.

Further preference is given to compounds of formula (Ic)

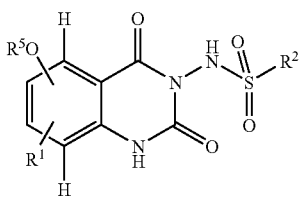

(Ic)

wherein $R^1$, $R^2$ and $R^5$ are as defined in this specification.

Further preference is given to compounds of formula (Id)

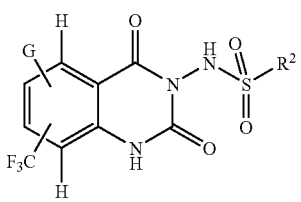

(Id)

wherein G and $R^2$ are as defined in this specification.

Further preference is given to compounds of formula (Ie)

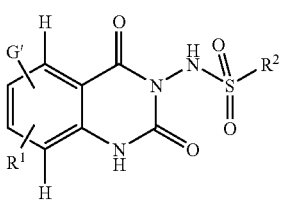

(Ie)

wherein $R^1$ and $R^2$ are as defined in this specification.

Further preference is given to compounds of formula (Ih)

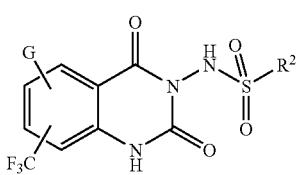

(Ih)

wherein G and $R^2$ are as defined in this specification.

Preferably, G is $R^3R^4N$.

Preferably, $R^3$ is hydrogen, aryl, aralkyl, acyl or alkyl optionally substituted by heterocyclyl, aryloxy, aralkyloxy or alkoxycarbonylamino, and $R^4$ is hydrogen or alkyl, or $R^3$ and $R^4$ together with the adjacent nitrogen atom form heteroaryl or heterocyclyl containing at least one nitrogen ring atom and attached via this nitrogen ring atom, wherein heteroaryl and heterocyclyl are optionally substituted by aryl, aralkyl, aryloxyalkyl, aminocarbonylalkyl or morpholinocarbonylalkyl, Preferably, $R^3$ and $R^4$ together with the adjacent nitrogen atom form 5-membered heteroaryl containing at least one nitrogen ring atom and attached via this nitrogen ring atom, most preferably imidazol-1-yl.

Preferably, $R^1$ represents nitro.

Preferably, $R^2$ represents methyl, ethyl, phenyl, benzyl, nitrophenyl or pyridyl, most preferably methyl, ethyl or phenyl.

In another embodiment, the invention provides compounds of the formula (I),
wherein
G is $NR^3R^4$ or $OR^5$, wherein
$R^3$ is hydrogen, aralkyl or alkyl optionally substituted by aryl, heterocyclyl, aryloxy, aralkyloxy or alkoxycarbonylamino, $R^4$ is hydrogen or alkyl, or
$R^3$ and $R^4$ together with the adjacent nitrogen atom form heteroaryl or heterocyclyl containing at least one nitrogen ring atom and attached via this nitrogen ring atom, wherein heteroaryl and heterocyclyl are optionally substituted by aryl, aminocarbonylalkyl, mono- or dialkyl aminocarbonylalkyl or morpholinocarbonylalkyl, and
$R^5$ is alkyl,
$R^1$ is nitro or trifluoromethyl, and
$R^2$ is alkyl,
and their salts.

Particular preferred are compounds of formula (Ia) wherein $R^1$ represents nitro and $R^2$ represents methyl.

Particular preferred are compounds of formula (Ia) wherein $R^1$ represents trifluormethyl and $R^2$ represents methyl.

Particular preferred are compounds of formula (Ia) wherein $R^1$ represents nitro and $R^2$ represents ethyl.

Particular preferred are compounds of formula (Ia) wherein $R^1$ represents trifluormethyl and $R^2$ represents ethyl.

Particular preferred are compounds of formula (Ia) wherein $R^1$ represents nitro and $R^2$ represents phenyl.

Particular preferred are compounds of formula (Ia) wherein $R^1$ represents trifluormethyl and $R^2$ represents phenyl.

Particular preferred are compounds of formula (I) wherein G represents a saturated unsubstituted heterocycle.

Particular preferred are compounds of formula (I) wherein Represents methyl and R4 represents hydroxaethyl.

The prefererred, particular preferred ranges and formula may be compared at will. The definitions apply to the compounds of formula (I) and the corresponding starting materials and intermediates.

In a further aspect, the present invention provides processes for the production of compounds of the invention.

Process 1:

Compounds of the formula (Ib)

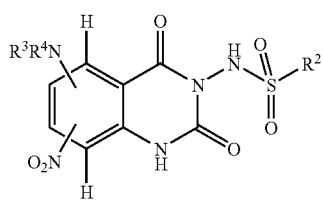

(Ib)

wherein $R^2$, $R^3$, and $R^4$ have the meaning indicated above, can be prepared by reacting a compound of the formula (II)

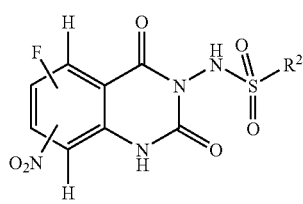

(II)

wherein R² has the meaning indicated above, with a compound of the formula (III)

R³R⁴N—H      (III), wherein R³ and R⁴ have the meaning indicated above.

For this purpose, a mixture of the compound of formula (II) with an excess of the compound of formula (III), preferably 1.5 to 30 eqivalents, most preferably 2 to 10 equivalents, neat or dissolved in a suitable inert solvent, such as 1,3-dimethyl-imidazolidin-2-one, dimethylsulfoxide, acetic acid or ethanol, can be heated in a closed vial to high temperatures, e.g. 150° C., using an oil bath or a microwave reactor for the required amount of time, e.g. 5 min to 1 h, or, alternatively, in a suitably high boiling inert solvent like dimethylsulfoxide in an open system to lower temperatures, e.g. 120° C., for longer periods of times, e.g. 16 h. If necessary, protected moieties such as hydroxyl or amino functions within the reaction product can be deprotected, or the reaction product can be further transformed, e.g. by reduction or oxidation.

The compound of formula (II) can be obtained by conventional means from amine (IV),

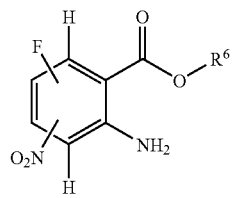

(IV)

wherein R⁶ is alkyl,
by conversion to the isocyanate (V)

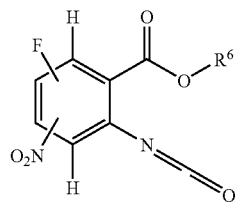

(V)

wherein R⁶ has the meaning indicated above, e.g. by reaction with phosgene, and subsequent cyclocondensation with sulfonylhydrazine (VI),

H₂N—NH—SO₂—R²      (VI)

wherein R² has the meaning indicated above, in a suitable inert solvent such as tetrahydrofuran, followed by the addition of a base, e.g. aqueous sodium hydroxide solution or an organic base such as triethylamine or Huenig's base.

The compounds of formulae (IV) and (VI) are known or can be prepared by or in analogy to literature-known procedures.

The following reaction scheme is illustrative for Process 1:

Scheme 1

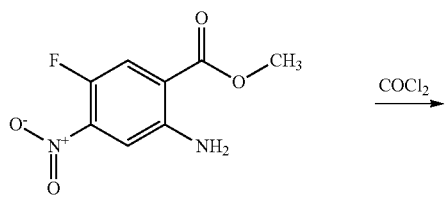

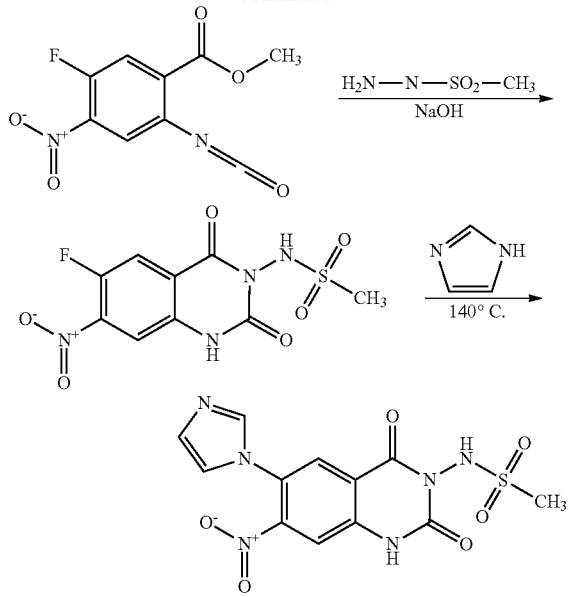

Process 2:
Compounds of the formula (Ic)

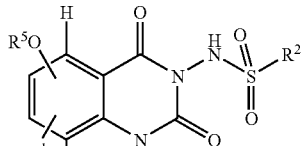

(Ic)

wherein R¹, R² and R⁵ have the meaning indicated above, can be obtained by reaction of a compound of formula (VII)

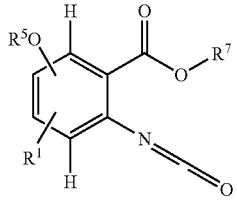

(VII)

wherein R¹ and R⁵ have the meaning indicated above, and R⁷ is alkyl,
with a compound of formula (VI), in a suitable inert solvent such as tetrahydrofuran, optionally in the presence of a suitable base such as aqueous sodium hydroxide solution or an organic base such as triethylamine or Hünig's base. Suitable temperatures for this reaction are in the range of 0-40° C., preferably 22° C.

The isocyanate (VII) can be prepared from amide (VIII)

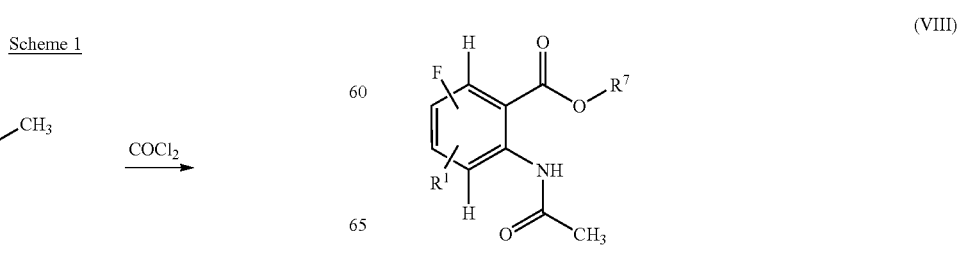

(VIII)

wherein $R^1$ and $R^7$ have the meaning indicated above,
by reaction with alcoholate (IX)

wherein $R^5$ has the meaning indicated above,
and $M^+$ is a metal, preferably alkaline metal ion, in a suitable inert solvent, e.g the corresponding alcohol $R^5$—OH, followed by hydrolysis of the acetamide, e.g. with 98% sulfuric acid, to the amine (X),

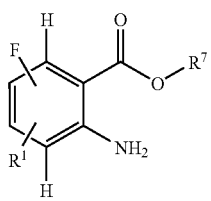

wherein $R^1$ and $R^7$ have the meaning indicated above, and conversion to the isocyanate (VII), e.g. with phosgene or triphosgene.

The compounds of formula (VII) are known or can be prepared by or in analogy to literature-known procedures.

The following reaction scheme is illustrative for Process 2:

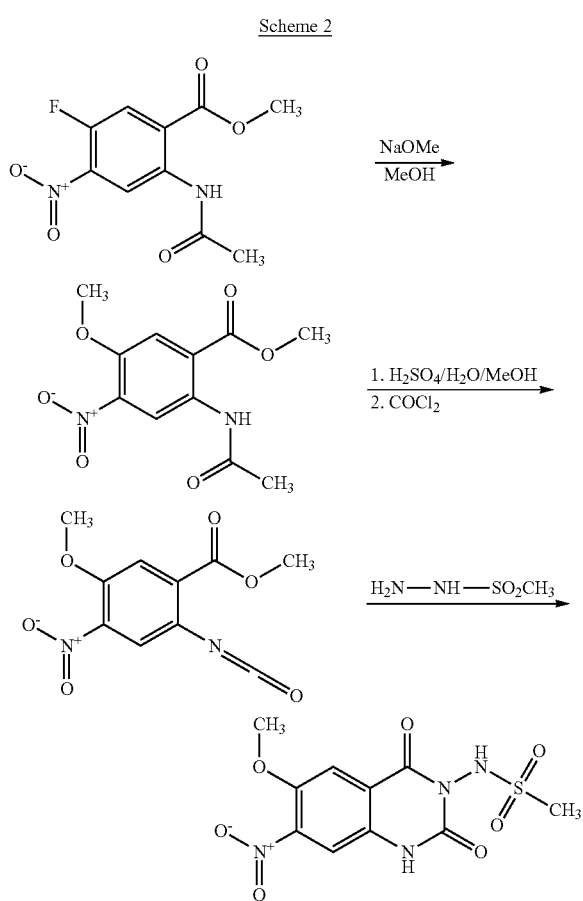

Process 3:
Compounds of the formula (Id),

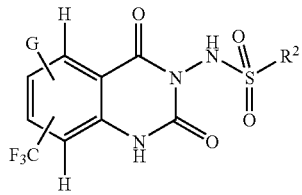

wherein G and $R^2$ have the meaning indicated above, can be prepared by reaction of the compound of formula (XI),

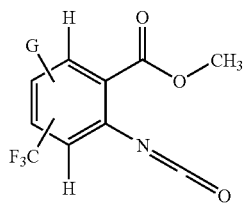

wherein G has the meaning indicated above, with the compound of formula (VI).

The reaction is carried out in a suitable inert solvent such as tetrahydrofuran, followed by the addition of a base, e.g. aqueous sodium hydroxide solution or an organic base such as triethylamine or Huenig's base.

The isocyanate (XI) can be prepared by nucleophilic substitution of fluoride (XII),

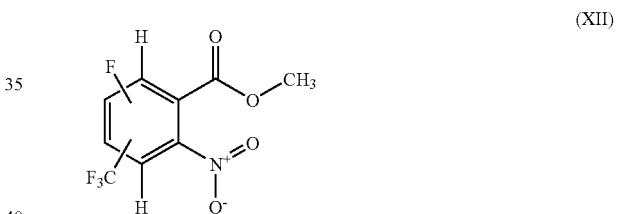

with amine (III) or alkoxide (IX) to yield nitro compound (XIII),

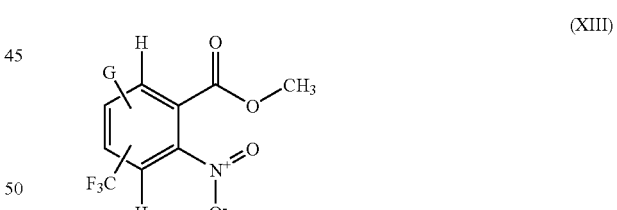

wherein G has the meaning indicated above,
followed by reduction to amine (XIV),

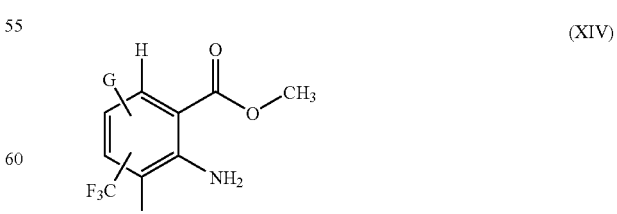

wherein G has the meaning indicated above, with a suitable reducing agent, e.g. by hydrogenation using palladium on charcoal as a catalyst, and transformation into isocyanate (XI), e.g. with phosgene or triphosgene.

The compounds of formula (XII) are known or can be prepared by or in analogy to literature-known procedures.

The following reaction scheme is illustrative for Process 3:

Scheme 3

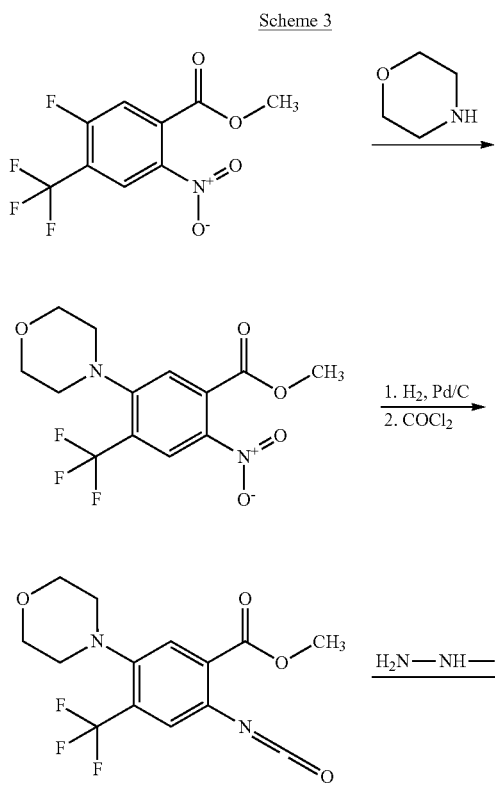

Process 4:
Compounds of the formula (Ie)

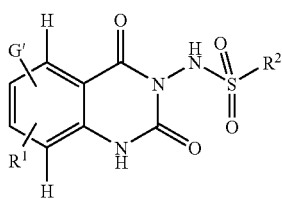

(Ie)

wherein $R^1$ and $R^2$ have the meaning indicated above, and G' is $R^{3'}R^{4'}N$ or $R^{5'}O$, wherein $R^{3'}$, $R^{4'}$, and $R^{5'}$ have the meaning of $R^3$, $R^4$, and $R^5$ respectively, as indicated above with the proviso that the carbon atoms of $R^{3'}$, $R^{4'}$, and $R^{5'}$ adjacent to the nitrogen and oxygen of $R^{3'}R^{4'}N$ and $R^{5'}O$, respectively, are primary or secondary carbon atoms, can be obtained by condensation, alkylation or reductive alkylation of compounds of the formula (If),

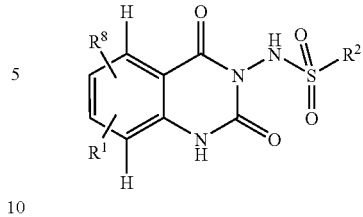

(If)

wherein $R^1$ and $R^2$ have the meaning indicated above, and $R^8$ is amino or hydroxyl,
with suitable halide or aldehyde precursors of $R^{3'}$, $R^{4'}$, or $R^{5'}$ in the presence of a condensation catalyst, a base or a reducing agent, e.g. sodium cyano borohydride, respectively.

The compounds of formula (If) can be obtained by deprotection of compounds of the formula (Ig)

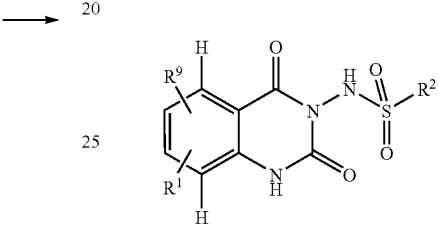

(Ig)

wherein $R^1$ and $R^2$ have the meaning indicated above, and $R^9$ is protected amino or hydroxyl, which in turn can be prepared by one of the above processes 1-3.

The suitable halide or aldehyde precursors of $R^{3'}$, $R^{4'}$, or $R^{5'}$ are known or can be prepared by or in analogy to literature-known procedures.

The following reaction scheme is illustrative for Process 4:

Scheme 4

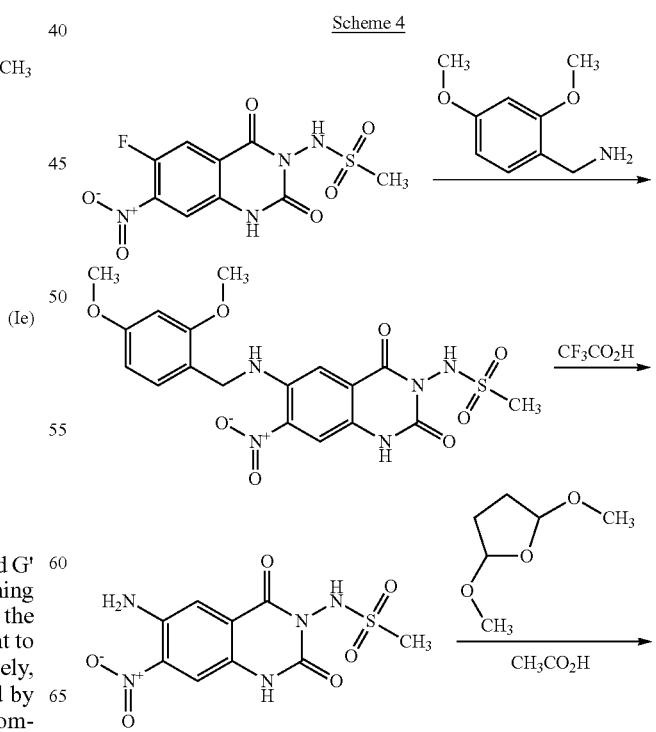

-continued

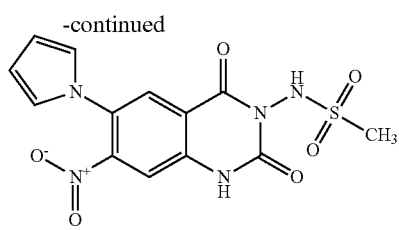

Process 5:
Compounds of the formula (Ih),

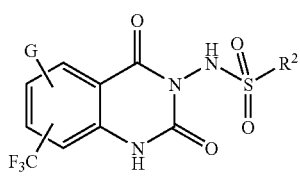

(Ih)

wherein G and R² have the meaning indicated above, are obtainable by reaction of the compound of formula (XVI),

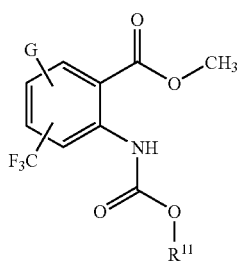

(XVI)

wherein G has the meaning indicated above, $R^{11}$ represents phenyl which his optionally substituted by halogen or $C_1$-$C_4$ alkyl, with the compound of formula (VI).

The reaction is preferably carried out in a suitable inert solvent such as tetrahydrofuran, followed by the addition of a base, e.g. aqueous sodium hydroxide solution or an organic base such as triethylamine, ethyl-diisopropylamine or Huenig's base.

The reaction is particular preferable for compounds of formula (If) wherein G is in the 6-position and CF3 groupd is in the 7-position.

The carbamate (XVI) can be prepared by substitution reaction of the corresponding amino compound of formula (XVII),

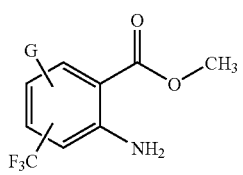

(XVII)

with a chloroformate (XVIII)
ClC(O)OR¹¹ (XVIII)

wherein $R^{11}$ has the meaning as indicated above, in the presence of a diluent, such as dioxane, to yield the carbamate (XVI).

The compounds of formula (XVIII) and (XVII) are known or can be prepared by or in analogy to literature-known procedures.

The following reaction scheme is illustrative for Process 5:

Scheme 5

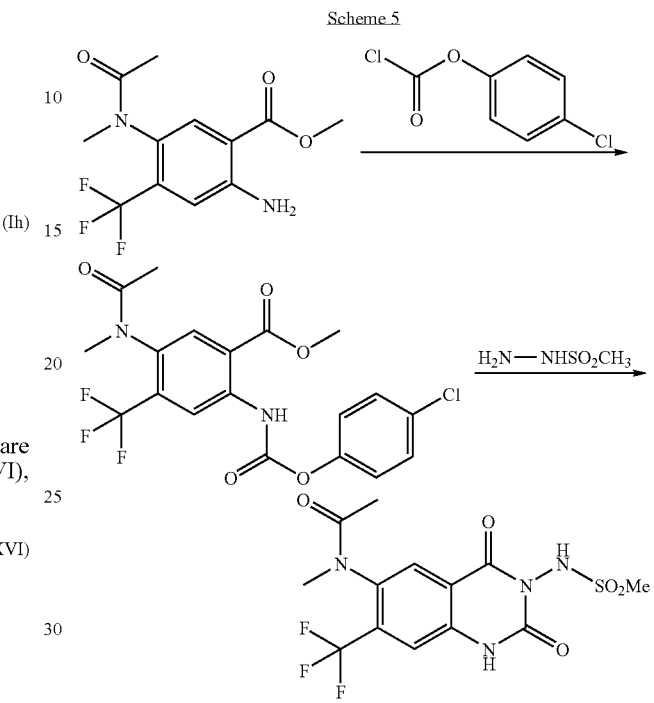

The following consideration may apply, as the case may be, to all processes described herein as well as for the preparation of the corresponding starting materials and intermediates:

One or more functional groups, for example carboxy, hydroxy, amino, or mercapto, may need to be protected in the starting materials by protecting groups. The protecting groups employed may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Acid addition salts may be produced from the free bases in known manner, and vice-versa. Compounds of formula I in optically pure form can be obtained from the corresponding racemates according to well-known procedures, e.g. HPLC with chiral matrix. Alternatively, optically pure starting materials can be used.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

In a further aspect, the compounds provides new intermediates as defined above. These intermediates are useful for the manufacture of compounds of formula (I) and also show interesting pharmaceutical properties. These compounds are also subject of the present invention.

The compounds of the invention exhibit pharmacological activity and are, therefore, useful as pharmaceuticals. In particular, the compounds are potent competitive AMPA receptor antagonists with some activity at kainate receptors.

The compounds of the invention are especially effective as pharmaceuticals in the treatment of epilepsy, esp. in partial seizures (simple, complex and partial evolving to secondarily generalized seizures) and generalized seizures [absence (typical and atypical), myoclonic, clonic, tonic, tonic-clonic and atonic].

The compounds of the invention are also especially effective as pharmaceuticals in the treatment of psychosis in schizophrenia, in bipolar disorder, in Parkinson's Disease and in drug-induced psychosis, as well as in the improvement of positive and negative symptoms and effective in treatment resistant patients (cf. Kalkman HO, Loetscher E GAD67: the link between GABA-deficit hypothesis and the dopaminergic- and glutamatergic theories of psychosis. J. Neural. Transm. 2003, 1110, 803-812).

Furthermore, the compounds of the invention are useful as pharmaceuticals in the treatment of any pathology, disorder or clinical condition involving AMPA receptor mediated neuronal damage, e.g. neurodegenerative disorders, such as multiple sclerosis, amyotrophic lateral sclerosis, Parkinson's Disease, Huntington's Disease or Alzheimers Disease, schizophrenia, esp. chronic schizophrenia, anxiety, depression, bipolar mood disorders, sleep disorders, cognitive disorders, emesis, tinnitus, pain, neuronal pain, migraine, tumor growth, withdrawal symptoms, ischemic and hypoxic conditions such as stroke, subarachnoid haemorrhage, perinatal hypoxia, brain and spinal cord trauma, head injury, high intracranial pressure, and any surgical procedure potentially associated with hypoxia of the central nervous system, and conditions produced by the actions of environmental, exogenous neurotoxins, including those produced by infections as well as those produced by metabolic changes and hepatic encephalopathy associated with liver failure.

For all these indications, the appropriate dosage will, of course, vary depending upon, for example, the compound of the invention employed, the host, the mode of administration and the nature and severity of the conditions being treated. However, in general, satisfactory results in animals are indicated to be obtained at daily dosages from about 0.1 to about 30 mg/kg animal body weight. In larger mammals, for example humans, an indicated daily dosage is in the range from about 5 mg to about 2 g of a compound of the invention conveniently administered, for example, in divided doses up to four times a day.

The active agents of the invention may be administered by any conventional route, in particular enterally, preferably orally, e.g. in the form of tablets or capsules, or parenterally, e.g. in the form of injectable solutions or suspensions.

In accordance with the foregoing, the present invention provides compounds for use as a pharmaceutical, in particular for use in the treatment of any pathology, disorder or clinical condition involving AMPA receptors in their etiology or involving AMPA-receptor mediated neuronal damage, and especially for use in any of the specific indications hereinbefore recited.

The present invention also provides a pharmaceutical composition comprising compounds in association with at least one pharmaceutical carrier or diluent. Such compositions may be manufactured in conventional manner. Unit dosage forms contain, for example, from about 1 mg to about 400 mg of an active agent according to the invention.

The present invention furthermore provides the use of a compound according to the invention, for the manufacture of a medicament for the treatment of any pathology, disorder or clinical condition involving AMPA receptors in their etiology or involving AMPA-receptor mediated neuronal damage.

Moreover the present invention provides a method for the treatment of any pathology, disorder or clinical condition involving AMPA receptors in their etiology or involving AMPA-receptor mediated neuronal damage, in a subject in need of such treatment, which comprises administering to such subject a therapeutically effective amount of a compound according to the invention.

Furthermore, the compounds of the invention can be combined with other drugs useful for the various indications, e.g. in the case of epilepsy with other anti-epileptic drugs like barbiturates and derivatives thereof, benzodiazepines, carboxamides, hydantoins, succinimides, valproic acid and other fatty acid derivates, other AMPA-antagonists. The compounds of the invention can also be combined with neuroleptic drugs selected from the list consisting of atypical antipsychotic drugs such as clozapine, olanzapine, risperidone and typical antipsychotic drugs such as haloperidol.

This application discloses in a further aspect the use of the compounds of formula (I) for the treatment of pathological conditions which respond to blockade of excitatory amino acid receptors, such as AMPA receptors, for example of neurodegenerative disorders, stroke, epilepsy, anxiety and pain.

It has now surprisingly been found that the compounds are also useful in the treatment of neuropathic pain.

The activity of the compounds in the treatment of neuropathic pain is evidenced, for example, in the following model of neuropathic pain in the rat:

Wistar rats are anaesthetised with enflurane and a small incision is made mid-way up one thigh to expose the sciatic nerve. The nerve is cleared of connective tissue and a 7-0 silk suture is inserted into the nerve using a ⅜ curved reverse-cutting min-needle, and tightly ligated so that the dorsal ⅓ to ½ of the nerve thickness is held within the ligature. The muscle and skin are closed with sutures and clips and the wound dusted with antibiotic powder. This procedure produces a mechanical hyperalgesia which develops within 2-3 days and is maintained for at least 4 weeks. Mechanical hyperalgesia is assessed by measuring paw withdrawal thresholds on both the ipsilateral (ligated) and contralateral (unligated) hindpaw to an increasing pressure stimulus applied to the paw using an analgesymeter (Ugo-Basile) with a wedge-shaped probe (area 1.75 mm$^2$) and a cut-off threshold of 250 g. The end point is taken as the first sign of pain response (struggling, vocalisation or paw withdrawal). Hyperalgesia is indicated by the difference in ipsilateral and contralateral withdrawal thresholds. Reversal of established hyperalgesia by administered compounds is measured 12-14 days following surgery, using 6 animals per treatment group. Paw withdrawal thresholds are measured prior to and then up to 6 hours following drug or vehicle administration. Statistical analysis is carried out on withdrawal threshold readings using ANOVA followed by Tukey's HSD test comparing drug treated and time-matched vehicle treated animals.

In this model, the compounds significantly reverse neuropathic mechanical hyperalgesia at 10 mg/kg p.o. With selected compounds of formula (I), a maximal reversal of neuropathic mechanical hyperalgesia of 35% is achieved after 3 hours on adminstration of 10 mg/kg p.o.

The activity of the compounds of formula I in the treatment of neuropathic pain can be confirmed in clinical trials, for example in the following study aimed at evaluating the efficacy of a compound in treating chronic pain in patients with diabetic neuropathy:

Patients are randomized to receive 2400 mg/day of the compound or placebo in a 1:1 ratio.

The study consists of a Pre-randomization Phase (1 week) and a Double-blind Phase (5 weeks). The double-blind Phase consists of three periods: a one week Titration Period, a three-week Maintenance Period and a one-week Follow-up Period.

During the 1-week Pre-randomization Phase, the eligibility of the patients is evaluated. Patients meeting all inclusion/exclusion criteria are randomized to either the compound or placebo in the Double-blind Phase. During the 1-week Titration Period, study medication is up-titrated from 800 mg/day (given b.i.d.) to 2400 mg/day (given b.i.d.). Patients who complete the 1-week Titration Period then enter the 3-week Maintenance Period. Patients who complete the 3-week Maintenance period or prematurely discontinue double-blind treatment then enter the 1-week Follow-up Period. Study medication is completely withdrawn on entry into the Follow-up Period. During the Double-blind Phase, serial efficacy and safety assessments are obtained.

120 male and female outpatients, aged 18-65 years with a clinical diagnosis of diabetes mellitus (type I or II) and a history of pain associated with diabetic neuropathy for 6 months to 3 years prior to study entry, are randomized 1:1 to the compound or placebo.

The total score of the Short-Form McGill Pain Questionnaire (SF-MPQ) at the end of Maintenence Period is used as primary efficacy parameter. Average weekly pain severity rating (daily patient pain diary) from start of randomized treatment to end of Maintenance Period, usage of rescue medication during the Titration and Maintenance Period, and average pain severity rating during the Follow-up Period (rebound pain), are used as secondary efficacy parameters.

The SF-MPQ total pain score at the end of the Maintenance Period is analyzed using an analysis of covariance model adjusting for the effect of treatment on post-treatment scores by using the baseline SF-MPQ total pain score as a covariate. Average weekly pain severity is analyzed using an analysis of covariance model with repeated measures using the treatment week and the mean pain severity rating during the Pre-randomization Phase as covariates. Usage of rescue medication during the Double-blind Phase is analyzed using the Cochran-Mantel-Haenszel test controlling for center. The mean pain severity rating during the Follow-up Period (rebound pain) is analyzed using an analysis of covariance model adjusting for the effect of treatment on the mean pain severity rating of the Follow-up Period with the mean pain severity rating during the Prerandomization Phase as a covariate.

In this study, the compounds, more particularly

N-{6-[(2-Hydroxy-ethyl)-methyl-amino]-2,4-dioxo-7-trifluoromethyl-1,4-dihydro-2H-quinazolin-3-yl}-methanesulfonamide N -(6-[1,4]Oxazepan-4-yl-2,4-dioxo-7-trifluoromethyl-1,4-dihydro-2H-quinazolin-3-yl)-methanesulfonamide N-(6-Morpholin-4-yl-2,4-dioxo-7-trifluoromethyl-1,4-dihydro-2H-quinazolin-3-yl)-methanesulfonamide are found to decrease pain severity ratings relative to placebo during the Maintenance and Follow-up Periods, in a statistically significant way.

The compounds are therefore useful in the treatment of neuropathic pain and associated hyperalgesia, including trigeminal and herpetic neuralgia, diabetic neuropathic pain, migraine, causalgia and deafferentation syndromes such as brachial plexus avulsion.

In a further aspect of the present invention, it has surprisingly been found that the compounds are also useful in the treatment of affective and attention disorders.

The activity of the compounds in the treatment of affective disorders including bipolar disorders, e.g. manic-depressive psychoses, extreme psychotic states e.g. mania, is evidenced, for example, in the following tests suitable for detecting drugs reversing psycho-motor stimulatory effects.

Test 1: NMDA-Antagonist Induced Locomotion:

Male Wistar Kyoto rats (Iffa Crédo, Lyon, France) weighing between 250 and 310 g are used. In principle 4 treatment groups are formed: 1) the compound (doses 1, 3 or 10 mg/kg) followed by the competitive NMDA receptor antagonist (S)-2-amino-3-(2'-chloro-5-phosphonomethyl-biphenyl-3-yl)-propionic acid, hereinafter SDZ 220-581 (10 mg/kg), 2) solvent-pretreatment followed by SDZ 220-581 (10 mg/kg), 3) solvent followed by solvent, 4) the compound (1, 3, 10 mg/kg) followed by solvent. Rats are randomly allocated to these pretreatment groups (n=10/dose group). Drugs are administered subcutaneous (s.c.), 15 min prior to SDZ 220-581. Immediately after the animals received SDZ 220-581, they are placed into the activity monitor for a period of 60 min. Locomotor activity is analysed over the initial 30 minutes.

Locomotion is recorded with a videotracking system (VideoMot2, TSE Technical and Scientific Equipment GmbH, Bad Hombourg, Germany), using a closed circuit digital videocamera (WV-BP.330/GE, Panasonic, Osaka, Japan). The video-signal from the camera is digitized and used for data analysis. Animals are on a normal 12/12 h day-night cycle, with light on at 06:00 H. Experiments are performed in a dimly lit room between 07:00 H and 15:00 H. Animals are placed in a round arena (diameter 42 cm, height 32 cm) made of grey polyvinylchloride plastic. The camera is placed such, that four animals (one per arena) can be recorded simultaneously.

In this test, the compounds (1-10 mg/kg, s.c.) do not significantly alter locomotor activity as compared to vehicle-treated animals at any time during a period of 30 min. However, the competitive NMDA receptor antagonist SDZ 220-581 (10 mg/kg, s.c.) induces a strong locomotor response. Thus, whereas control animals walk approximately 8-10 m during 30 min, SDZ 220-581-treated animals walked approximately 30 m. This locomotor response is reduced in a dose dependent manner by the compounds. With selected compounds of formula(I) (e.g. at 10 mg/kg), the effect of the NMDA-antagonist SDZ 220-581 is almost normalized.

Test 2: NMDA-Channel Blocker Induced Head Swaying and Circling:

Adult male Wistar Kyoto rats (340-380 g; Iffa Credo, Lyon, France) are used. The animals are randomized to the following treatment groups (n=10 per group): the compound (dosed 0, 3 or 10 mg/kg) followed by phencyclidine (PCP; an NMDA channel blocker, dosed 0 or 10 mg/kg). Compound (at t=−15 min) and PCP (at t=0 min) are administered s.c. in a volume of 1 ml/kg. Video-recordings of the animals behaviour over the period 0-30 min following PCP are scored by an observer who is unaware about the animals pretreatment. Head-swaying (rocking the head repeatedly by at least 2 cm left and right) and circling (turning around by using the forepaws, whereas the hindpaws remain more or less on the original position) are scored as present (1) or absent (0), every five minutes for the duruation of 1 minute. The scores for individual animals is summed and group scores used for statistical analysis (t-test with Bonferroni correction).

In this test, PCP (10 mg/kg, s.c.) induces weak head-swaying and circling. Pretreatment with the compounds (3 and 10 mg/kg, s.c.) significantly enhances these behavioural responses to PCP (P<0.05).

NMDA-antagonist induced locomotor responses reflect a mania-like state. Blockade of this activity indicates an antimanic activity. Furthermore, enhancement of head-swaying and circling suggest a behavioural desinhibition (=anxiolytic-/antidepressant-like) and sociotropic activity. Therefore, the compounds are useful in the treatment of affective disorders including bipolar disorders, e.g. manic-depressive psychoses, extreme psychotic states e.g. mania and excessive mood swings where behavioural stabilization is desired. In addition, the compounds are indicated in ADHD (attention deficit hyperactivity disorders) and other attention disorders, e.g. autism, anxiety states, generalized anxiety and agoraphobia, as well as those behavioural states characterized by social withdrawal e.g. negative symptoms.

In a further aspect of the present invention, it has surprisingly been found that the compounds are also useful in the treatment of schizophrenia and psychosis like symptoms in other indications, e.g. Parkinson's disease.

The antischizophrenic activity of the compounds is indicated in standard tests, e.g. in the amphetamine-induced hyperlocomotion test. Blockade of amphetamine-induced hyperlocomotion is well known as screening paradigm for antischizophrenic activity.

Male Wistar rats (Iffa Crédo, Lyon, France) weighing between 215 and 315 g are used. In principle 4 treatment groups are formed: 1) the compound (doses 1, 3 or 10 mg/kg) followed by amphetamine (1 mg/kg), 2) solvent-pretreatment followed by amphetamine (1 mg/kg), 3) solvent followed by solvent, 4) the compound (10 mg/kg) followed by solvent. Rats are randomly allocated to these pretreatment groups (n=10/dose group). Drugs are administered subcutaneous (s.c.), 15 min prior to amphetamine. Immediately after the animals received amphetamine, they are placed into the activity monitor for a period of 60 min. Locomotor activity is analysed over the initial 30 minutes.

Locomotion is recorded with a videotracking system (VideoMot2, TSE Technical and Scientific Equipment GmbH, Bad Hombourg, Germany), using a closed circuit digital videocamera (WV-BP.330/GE, Panasonic, Osaka, Japan). The video-signal from the camera is digitized and used for data analysis. Animals are on a normal 12/12 h. day-night cycle, with light on at 06:00 H. Experiments are performed in a dimly lit room between 07:00 H and 15:00 H. Animals are placed in a round arena (diameter 42 cm, height 32 cm) made of grey polyvinylchloride plastic. The camera is placed such, that four animals (one per arena) can be recorded simultaneously.

Amphetamine is dissolved in physiological saline as 1 mg/ml and administered s.c. in a volume of 1 ml/kg. The compound is dissolved in a few drops of NaOH (0.1 N) and further diluted with physiological saline as required to obtain solutions of 10, 3 and 1 mg/ml. It is administered s.c. in a volume of 1 ml/kg.

Comparison between groups is done with Student's t-test, corrected for multiple testing using the Bonferroni procedure.

In this test, the compounds of formula (I) reduce the amphetamine-induced locomotion at doses of about 1 mg to about 10 mg/kg s.c.

In still a further aspect of the present invention, it has surprisingly been found that the compounds are also useful in the treatment of tinnitus.

The activity in tinnitus of the compounds is indicated in standard tests, e.g. in the salicylate-induced tinnitus model.

It has been demonstrated [C. A. Bauer et al., Hearing Research 147 (2000) 175-182] that chronic salicylate exposure causes upregulation of glutamic acid decarboxylase (GAD) expression in the rat inferior colliculus (IC), associated with the development of tinnitus. Furthermore, electrophysiological recordings from auditory neurons using patch clamp recording techniques [D. Peruzi et al. Neuroscience 101 (2000) 403-416, X. Lin et al., Journal of Neurophysiology 79 (1998) 2503-2512] and single neuron recordings [J. J. Eggermont and M. Kenmochi, Hearing Research 117 (1998) 149-160] showed that the excitability of neurons is changed following salicylate and quinine treatment.

Administration of salicylate or quinine caused an increase in the firing rate auditory neurons measured by extracellular electrophysiological recording techniques. Using in vitro electrophysiological recording techniques superfusion with salicylate increases the excitability of the recorded neurons. On administration of the compounds at concentrations of about 1 nM to 100 µM, the effects of salicylate were reversed.

For the treatment of the above mentioned indications, appropriate dosage will of course vary depending upon, for example, the compound employed, the host, the mode of administration and the nature and severity of the condition being treated. However, in general, satisfactory results in animals are indicated to be obtained at a daily dosage of from about 1 to about 50 mg/kg animal body weight. In larger mammals, for example humans, an indicated daily dosage is in the range from about 10 to about 1000 mg of a compound according to the invention, conveniently administered, for example, in divided doses up to four times a day.

In a further aspect of the present invention, it has surprisingly been found that the compounds are also useful in the treatment of myopia and other ocular disorders.

Such disorders include, but are not limited to, age-related macular degeneration, diabetic retinopathy, cystoid macular edema (CME), pathologic myopia, Leber's hereditary optic neuropathy, retinitis pigmentosa, and other hereditary retinal degenerations.

The activity against myopia of the compounds is indicated in standard tests, e.g. in the model according to R. A. Stone et al. [Proc. Natl. Acad. Sci. (USA) 86, 704-706 (1989)] wherein experimental myopia is produced in chicken, on administration of about 0.1 to about 1 mg/kg in eye drops.

Efficacy in the described ocular disorders might be established for example in the following animal models:

1) Spontaneous development of a secondary form of glaucoma (e.g. pigment dispersion, angle closure or angle dysgenesis) in mice (for example, but not exclusively, strains DBA/2J, DBA/2Nnia, and AKXD28/Ty mice as described in Anderson et al., BMC Genetics 2001; 2:1, Chang et al., Nature Genetics 1999; 21: 405-409, John et al., Invest. Ophthalmol. Vis. Sci. 1998; 39: 951-962, Sheldon et al., Lab. Animal Sci. 1995; 15:508-518)
2) Genetic animal models for retinal degeneration, e.g. rd mouse (as described in Li et al., Invest. Ophthalmol. Vis. Sci. 2001; 42: 2981-2989), Rpe65-deficient mouse (Van Hooser et al., PNAS 2000.; 97: 8623-8628), RCS rat (Faktorovich et al., Nature 1990; 347:83-86), rds mouse (Ali et al., Nature Genetics 2000, 25: 306-310), rcd1 dog (Suber et al., PNAS 1993; 90: 3968-3972)
3) Experimental retinal degeneration induced by
   light exposure in mice (as described in Wenzel et al., Invest. Ophthalmol. Vis. Sci. 2001; 42: 1653-1659) or rats (Faktorovich et al., J. Neurosci. 1992; 12: 3554-3567)
   administration of N-methyl-N-nitrosourea (Kiuchi et al., Exp. Eye Res. 2002; 74: 383-392) or sodium iodate (Sorsby & Harding, Vision Res. 1962; 2: 139-148).
4) Experimental model for the injury of the optic nerve (ON)
   by ON crush in mice (Levkovitch-Verbin et al., Invest. Ophthalmol. Vis. Sci. 2000; 41: 4169-4174) and rats (Yoles and Schwartz, Exp. Neurol. 1998; 153:1-7)
   by ON transection in rats (as described in Martin et al., Invest. Ophthalmol. Vis. Sci. 2002; 43: 2236-2243, Solomon et al. J. Neurosci. Methods 1996; 70:21-25)
   by experimental transient (acute) retinal ischemia in rats after ophthalmic vessel ligature (as described in Lafuente et al., Invest. Ophthalmol. Vis. Sci. 2001; 42:2074-2084) or cannulation of the anterior chamber (Buchi et al., Ophthalmologica 1991; 203:138-147)
   by intraocular endothelin-1 injection in rats (Stokely at al., Invest. Ophthalmol. Vis. Sci. 2002; 43: 3223-3230) or rabbits (Takei et al., Graefes Arch. Clin. Exp. Ophthalmol 1993; 231:476-481).

For the treatment of myopia and other ocular disorders, appropriate dosage will of course vary depending upon, for example, the compound employed, the host, the mode of administration and the nature and severity of the myopia. However, in general, satisfactory results in animals are indicated to be obtained at a daily dosage of from about 0.01 to about 1 mg/kg animal body weight. In larger mammals, for example humans, an indicated daily dosage is in the range from about 0.25 to about 10 mg of a compound according to the invention, conveniently administered, for example, in divided doses up to four times a day.

For the above mentioned indications, the compounds may be administered in any usual manner, e.g. orally, for example in the form of tablets or capsules, or parenterally, for example in the form of injection solutions or suspensions.

For the treatment of myopia and other ocular disorders, the compounds may be administered topically in or around the eye, for example as eyedrops, ophthalmic suspensions or ointments, subconjunctival, peribulbar, retrobulbar or intravitreal injections, possibly with the use of slow-release devices, such as conjunctival inserts, microspheres or other periocular or intraocular depot devices.

The compounds are preferably applied topically to the eye in ca. 0.002 to ca. 0.02% ophthalmological solutions. The ophthalmic vehicle is such that the compound is maintained in contact with the ocular surface for a sufficient time period to allow the compound to penetrate the corneal and internal regions of the eye. The pharmaceutically acceptable ophthalmic vehicle may be e.g. and ointment, vegetable oil, or encapsulating material.

Suitable compounds for the treatment of the above mentioned indications include
N-{6-[(2-Hydroxy-ethyl)-methyl-amino]-2,4-dioxo-7-trifluoromethyl-1,4-dihydro-2H-quinazolin-3-yl}-methanesulfonamide
N-(6-[1,4]Oxazepan-4-yl-2,4-dioxo-7-trifluoromethyl-1,4-dihydro-2H-quinazolin-3-yl)-methanesulfonamide
N-(6-Morpholin-4-yl-2,4-dioxo-7-trifluoromethyl-1,4-dihydro-2H-quinazolin-3-yl)-methanesulfonamide
and their pharmaceutically acceptable salts.

The present invention also provides pharmaceutical compositions comprising a compound of formula I in association with at least one pharmaceutical carrier or diluent, for use in the treatment of neuropathic pain, affective and attention disorders, schizophrenia, tinnitus, myopia and other ocular disorders. Such compositions may be manufactured in conventional manner. Unit dosage forms for the treatment of neuropathic pain, affective and attention disorders, schizophrenia and tinnitus may contain for example from about 2.5 mg to about 500 mg of the compound of formula 1. Unit dosage forms for the treatment of myopia and other ocular disorders may contain for example from about 0.05 mg to about 5 mg of the compound of formula I.

The invention further provides the use of a compound of formula (I) for the manufacture of a pharmaceutical composition for the prevention, treatment or delay of progression of neuropathic pain, affective and attention disorders, schizophrenia, tinnitus, myopia and other ocular disorders.

The invention furthermore provides a method for the prevention, treatment or delay of progression of neuropathic pain, affective and attention disorders, schizophrenia, tinnitus, myopia and other ocular disorders in a subject in need of such treatment, which comprises administering to said subject a therapeutically effective amount of a compound of formula I.

In a further aspect, it has now surprisingly been found that the compounds are also useful in the treatment of multiple sclerosis and related demyelinating diseases, e.g. neuromyelitis optica.

The activity of the compounds in the treatment of multiple sclerosis is evidenced, for example, in the following model of experimental autoimmune encephalomyelitis (EAE), the primary animal model for the indication multiple sclerosis (MS), an autoimmune disease of the central nervous system.

Female Dark Agouti rats (DA-rats) are kept in a climate-controlled room with 12 hr light/dark cycles, housed in sawdust-lined cages with 4 to 5 rats per cage, and given standard rodent chow and water ad libitum. Severely paralyzed animals are especially provided with easier access to food and water. The rats are allowed at least one week to adapt to their surroundings, then they are randomly distributed into experimental groups (10 per group) and individually numbered with a tail mark. Rats are 8-9 weeks old (about 135 g) at the time of immunization on day 0. For optimal EAE induction, the immunization procedure utilizes freshly isolated brain and spinal cord (40:60 ratio) from adult DA rats as a source of syngeneic encephalitogenic neuroantigens. The central nervous system (CNS) tissue samples, also referred to as DA-b/sc, are stored in Eppendorf tubes at −70° C. until needed.

Rats are lightly anesthetized with isoflurane and immunized by a single intradermal (i.d.) injection at the dorsal root of the tail with 200 µl inoculum containing 1 part (volume: volume) CNS tissue emulsified in the appropriate diluent to 1 part incomplete Freund's adjuvant (IFA) supplemented with

*Mycobacterium tuberculosis* strain H37RA (Difco, Detroit, Mich.). The IFA-*mycobacterium* mixture is hereafter designated CFA (complete Freund's adjuvant). More specifically, DA-b/sc is emulsified in 'syringe A' containing 0.9% NaCl using a Polytron PT 3100 homogenizer (Kinematica, Lucerne, Switzerland) at 28,000 rpm for about 3 min. The antigen emulsion is gradually added to CFA in 'syringe B' while homogenizing. All solutions are kept on ice and not allowed to overheat with high speed mixing.

Adjuvant control animals are injected with CFA alone (1.6 mg *M. tuberculosis* per rat) and treated with the vehicle. Animals in the other experimental groups are injected with the neuroantigen-CFA emulsion (65 mg DA-b/sc and 1.6 mg *mycobacterium* per rat) and treated with vehicle alone or vehicle containing the test compound. The study is usually terminated on day 63, nine weeks after immunization on day 0.

Clinical EAE scoring: The animals are examined daily for neurological signs and body weight change. Clinical grades of EAE are assessed using a disease scale from 0 to 4:
0=no disease
1=complete loss of tail tonus
2=weakness of hindlimb(s) or ataxia
3=complete paralysis of either both hindlimbs or forelimbs
4=moribund condition with paralysis of both forelimbs and hindlimbs;
[disease-related mortality]

Scores of 3-4 are often accompanied by urinary incontinence. EAE-related mortality is recorded with a maximum score of 4. Other recorded data include day of EAE onset and % disease incidence per group.

Compound application: The compounds are applied for 14 to 21 days, starting on day 0 (prophylactic treatment) or on day 12 post-immunization (therapeutic treatment). The compounds are applied bid or tid and are given orally, intraperitoneally, or subcutaneously.

Statistical analysis: Since disease severity and duration are both key parameters to consider in drug testing, clinical scores are analysed as area under the curve (AUC) of scores over time.

In this EAE model, 10 to 20% of the antigen-immunized control animals can die due to disease-related causes. To account for this relevant information in the statistical analysis, the method of Gould was applied [Gould AL. A new approach to the analysis of clinical drug trials with withdrawals. Biometrics 1980; 36:721-7]. Animals in each group were ranked by their AUC value (increasing disease severity). Deceased rats were positioned according to the time of death, thereby giving them higher ranks than the survivors. Ranks were compared using non-parametric Wilcoxon Mann-Whitney tests (StatXact V3, Cytel Software Corp.). Probabilities (p)≦0.05 are considered statistically significant.

In this model, the compounds ameliorate the severity of EAE symptoms. For selected compounds of formula (I) an effect is seen at 2×10 mg/kg, i.p.

Suitable compounds for the treatment of multiple sclerosis
N-{6-[(2-Hydroxy-ethyl)-methyl-amino]-2,4-dibxo-7-trifluoromethyl-1,4-dihydro-2H-quinazolin-3-yl}-methanesulfonamide
N -(6-[1,4]Oxazepan-4-yl-2,4-dioxo-7-trifluoromethyl-1,4-dihydro-2H-quinazolin-3-yl)-methanesulfonamide
N-(6-Morpholin-4-yl-2,4-dioxo-7-trifluoromethyl-1,4-dihydro-2H-quinazolin-3-yl)-methanesulfonamide
and their pharmaceutically acceptable salts.

The present invention also provides pharmaceutical compositions comprising a compound of formula I in association with at least one pharmaceutical carrier or diluent, for use in the treatment of multiple sclerosis and related demyelinating diseases, e.g. neuromyelitis optica. Such compositions may be manufactured in conventional manner. Unit dosage forms for the treatment multiple sclerosis and related demyelinating diseases, e.g. neuromyelitis optica may contain for example from about 2.5 mg to about 500 mg of the compound of formula I.

The invention further provides the use of a compound of formula (I) for the manufacture of a pharmaceutical composition for the prevention, treatment or delay of progression of multiple sclerosis and related demyelinating diseases, e.g. neuromyelitis optica.

The invention furthermore provides a method for the prevention, treatment or delay of progression of multiple sclerosis and related demyelinating diseases, e.g. neuromyelitis optica in a subject in need of such treatment, which comprises administering to said subject a therapeutically effective amount of a compound of formula (I).

In a further aspect, the present invention relates to methods and materials for the treatment of dementia.

Surprisingly, it has been found that dementia can be treated by administration of an AMPA receptor antagonist. Hence, the present invention relates to a method for the treatment and/or prevention dementia comprising the step of administering to a warm-blooded animal, including a human, in need thereof an effective amount of AMPA receptor antagonist.

The term "AMPA receptor antagonists" as used herein refers to compounds of formula (I)

Particular suitable compounds for the treatment of dementia are
N-{6-[(2-Hydroxy-ethyl)-methyl-amino]-2,4-dioxo-7-trifluoromethyl-1,4-dihydro-2H-quinazolin-3-yl}-methanesulfonamide
N-(6-[1,4]Oxazepan-4-yl-2,4-dioxo-7-trifluoromethyl-1,4-dihydro-2H-quinazolin-3-yl)-methanesulfonamide
N-(6-Morpholin-4-yl-2,4-dioxo-7-trifluoromethyl-1,4-dihydro-2H-quinazolin-3-yl)-methanesulfonamide
and their pharmaceutically acceptable salts.

The term "dementia" as used herein includes, but is not restricted to, Alzheimer's dementia with or without psychotic symptoms. In particular, the methods and materials described herein are suitable for the treatment of behavioral disturbances observed with such types of It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

The pharmacological activity of a compound of formula(I) may, for example, also be demonstrated in a clinical study. Such clinical studies are preferably randomized, double-blind, clinical studies in patients with Alzheimer's Disease. The beneficial effects on Alzheimer's Disease can be determined directly through the results of these studies or by changes in the study design which are known as such to a person skilled in the art.

It is one objective of this invention to provide a pharmaceutical composition comprising a quantity, which is therapeutically effective against dementia, comprising at least one AMPA receptor antagonist, and at least one pharmaceutically acceptable carrier.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active ingredient, alone or in combination with one or more pharmaceutically acceptable carries, especially suitable for enteral or parenteral application. The preferred route of administration of the dosage forms of the present invention is orally.

The novel pharmaceutical composition contain, for example, from about 10% to about 100%, preferably from about 20% to about 60%, of the active ingredients. Pharmaceutical preparations for the therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of active ingredient or ingredients contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils or alcohols; or carriers such as starches, sugars, microcristalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are obviously employed.

Furthermore, the present invention relates to the use of a compound of formula (I) for the preparation of a medicament for the treatment of dementia.

Additionally, the present invention provides a method of treating a warm-blooded animal having dementia comprising administering to the animal a compound of formula (I) in a quantity which is jointly therapeutically effective against dementia and in which the compounds can also be present in the form of their pharmaceutically acceptable salts.

The effective dosage of each of the active ingredients employed in the compound of formula (I) may vary depending on the particular compound or pharmaceutical composition employed, the mode of administration, the severity of the condition being treated. Thus, the dosage regimen the compound of formula (I) is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

The invention is illustrated, but not limited, by the following examples.

WORKING EXAMPLES

Abbreviations:
CNQX 7-Nitro-2,3-dioxo-1,2,3,4-tetrahydro-quinoxaline-6-carbonitrile
DMSO Dimethyl sulfoxide
HV high vacuum
HEPES 4-(2-Hydroxyethyl)piperazine-1-ethanesulphonic acid
HPLC High Performance Liquid Chromatography
IR Infrared spectroscopy
m.p. melting point
MPLC Medium pressure liquid chromatography
RP reversed phase
SPL Sound Pressure Level
TFA trifluoro acetic acid
TLC thin layer chromatography Example 1

N-(6-Imidazol-1-yl-7-nitro-2,4-dioxo-1,4-dihydro-2H-quinazolin-3-yl)-methanesulfonamide

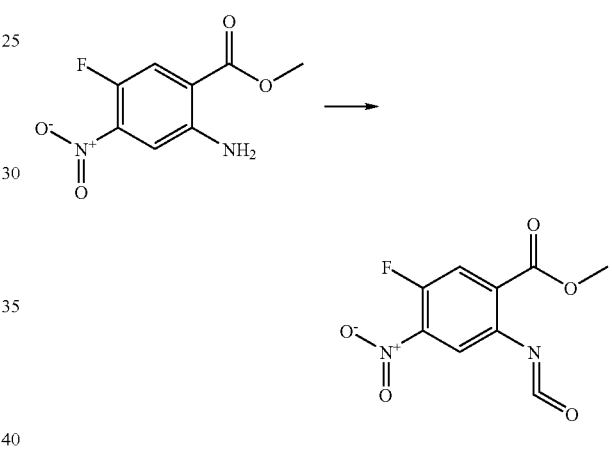

A solution of 15 ml of phosgene in toluene (20%) is dropped to a suspension of 1 g of 2-amino-5-fluoro-4-nitro-benzoic acid methyl ester in 20 ml of dry toluene at −15° C. A slow stream of phosgene is introduced and the reaction mixture heated to reflux. After 45 minutes, argon is blown through the yellow solution and the solvent distilled off thereby yielding 1.1 g 10 of 5-fluoro-2-isocyanato4-nitro-benzoic acid methyl ester as a yellow solid, sufficiently pure for the next step. IR (CHCl$_3$): 2240 cm$^{-1}$.

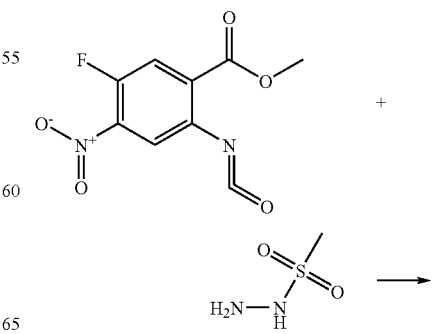

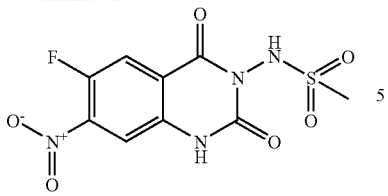

To a solution of 1.1 g (4.58 mmol) of 5-fluoro-2-isocyanato-4-nitro-benzoic acid methyl ester in 20 ml of dry tetrahydrofuran 0.504 g (4.58 mmol) of methanesulfonyl hydrazide in 7 ml of 15 dry tetrahydrofuran are added. The resulting suspension is stirred for 1 hour, then treated with 4.58 ml of 1 M NaOH solution and stirred for 3.5 hours. After acidification with 5.7 ml of 2 M HCl solution, the mixture is concentrated until formation of a precipitate, filtered, and the residue washed with water and recrystallized from tetrahydrofuran giving 0.774 g of the title compound as a beige powder, m.p. 240-255° C. (decomp.).

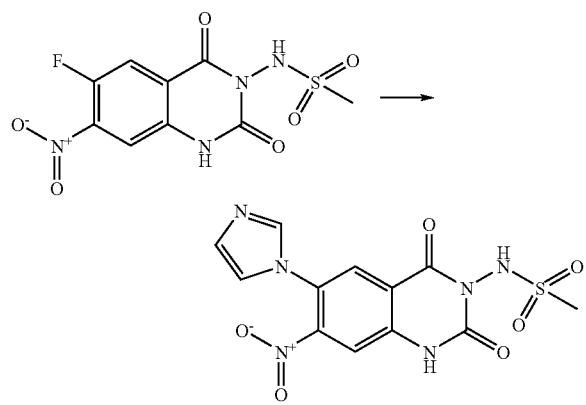

A mixture of 530 mg (1.665 mmol) of N-(6-fluoro-7-nitro-2,4-dioxo-1,4-dihydro-2H-quinazolin-3-yl)-methanesulfonamide, 567 mg (8.325 mmol) of imidazole and 7.7 ml of dry 1,3-dimethyl-2-imidazolidinone is heated to 140° C. (oil bath temperature) for 90 minutes in a closed vial. After cooling, the dark solution is poured on 130 ml of water and the pH adjusted to ~5 by adding 2 M acetic acid. The precipitate formed is filtered and recrystallized four times from DMSO/water, yielding 214 mg of the title compound as a red powder, m.p. >270° C.

Example 2

N-[6-(4-Hydroxymethyl-imidazol-1-yl)-7-nitro-2,4-dioxo-1,4-dihydro-2H-quinazolin-3-yl]-methanesulfonamide

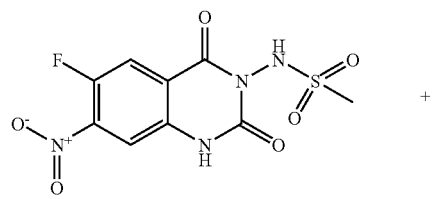 +

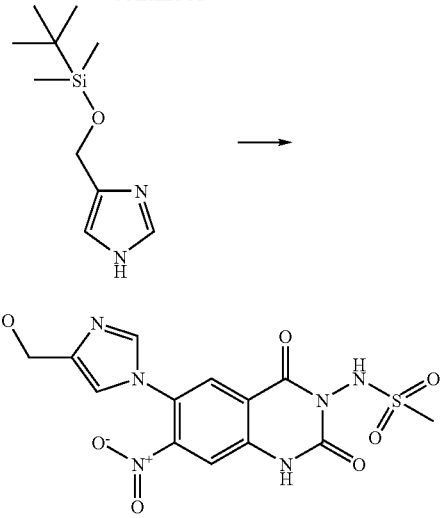

A mixture of 100 mg (0.314 mmol) of N-(6-fluoro-7-nitro-2,4-dioxo-1,4-dihydro-2H-quinazolin-3-yl)-methanesulfonamide, 333 mg (1.57 mmol) of 4-(tert-butyl-dimethyl-silanyloxymethyl)-1H-imidazole and 1 ml of dry 1,3-dimethyl-2-imidazolidinone is heated to 140° C. (oil bath temperature) in a closed vial for 4 hours. After cooling, the orange solution is diluted with ethyl acetate and the organic phase washed with water and brine and dried over $Na_2SO_4$. Evaporation of the solvent gives an oil which is purified by medium pressure chromatography on silica gel with ethyl acetate/acetic acid 98:2 as eluent, yielding 53 mg of N-{6-[4-(tert-butyl-dimethyl-silanyloxymethyl)-imidazol-1-yl]-7-nitro-2,4-dioxo-1,4-dihydro-2H-quinazolin-3-yl}-methanesulfonamide, m.p. >270° C.

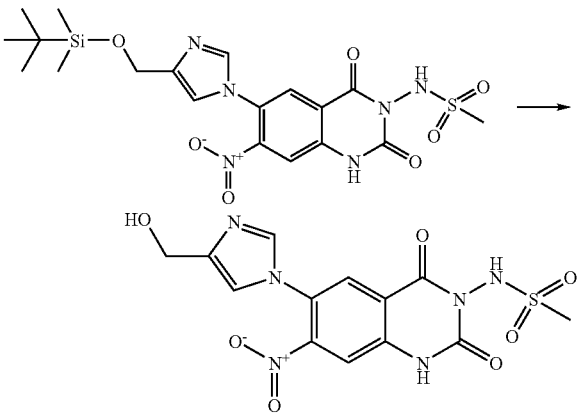

A mixture of 1 g (1.96 mmol) of N-{6-[4-(tert-butyl-dimethyl-silanyloxymethyl)-imidazol-1-yl]-7-nitro-2,4-dioxo-1,4-dihydro-2H-quinazolin-3-yl}-methanesulfonamide, 0.738 g (2.34 mmol) of tetrabutylammonium fluoride trihydrate and 20 ml of tetrahydrofuran is stirred at 50° C. for 18 hours. The reaction mixture is concentrated to dryness and the residue fractionated by medium pressure chromatography on a RP-C18 column (20 μM material) with acetonitril/water 1:1 (containing 0.1% trifluoroacetic acid) as eluent. The residue obtained by evaporation of fractions 2-5 is dissolved in water and the pH adjusted to ~5 with diluted $NH_4OH$ solution. The product precipitates and is collected by filtration. The residue obtained from fractions 6-13 is fractionated by medium pressure chromatography on a RP-C18 column (20 μM material) with acetonitril/water 1:2 as eluent. During concentration of the fractions the product precipitates and is collected by filtration. Crystallization of all combined product fractions from DMSO/water gives 0.328 g of N-[6-(4-hydroxymethyl-imidazol-1-yl)-7-nitro-2,4-dioxo-1,4-dihydro-2H-quinazolin-3-yl]-methanesulfonamide as a yellow powder, m.p. >300° C.

Example 3

N-(6-Morpholin-4-yl-7-nitro-2,4-dioxo-1,4-dihydro-2H-quinazolin-3-yl)-methanesulfonamide

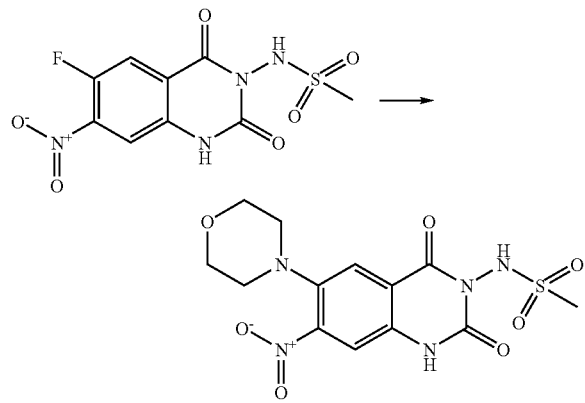

A mixture of 100 mg (0.314 mmol) of N-(6-fluoro-7-nitro-2,4-dioxo-1,4-dihydro-2H-quinazolin-3-yl)-methane-sulfonamide and 0.274 ml (3.14 mmol) of morpholine is heated at 140° C. (oil bath temperature) for 1 hour in a closed vial. After cooling, the residue is dissolved in water, the solution acidified with 2 M acetic acid to pH ~5 and allowed to stand at room temperature. An orange precipitate forms which is filtered and recrystallized from DMSO/water yielding 81 mg of the title compound as an orange powder, m.p. >260° C.

Example 4

N-(6-Dimethylamino-7-nitro-2,4-dioxo-1,4-dihydro-2H-quinazolin-3-yl)-methanesulfonamide

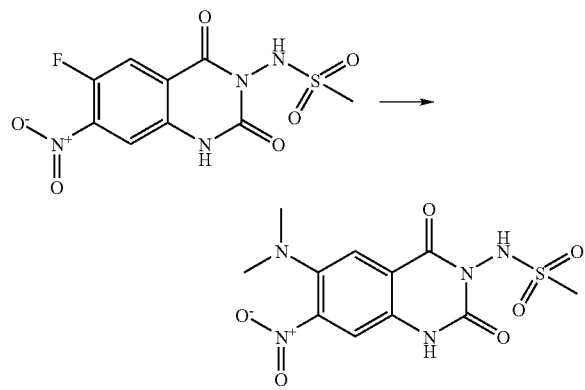

A mixture of 100 mg (0.314 mmol) of N-(6-fluoro-7-nitro-2,4-dioxo-1,4-dihydro-2H-quinazolin-3-yl)-methane-sulfonamide and 0.185 ml (0.925 mmol) of dimethylamine (33% in ethanol) in a closed vial is heated in a microwave reactor at 150° C. for 15 minutes. After cooling, the reaction mixture is concentrated to dryness and the residue crystallized from tetrahydrofuran/water yielding 90 mg of the title compound as an orange powder, m.p. 245-260° C. (decomp.).

Example 5

N-[6-(2-Hydroxy-1-hydroxymethyl-ethylamino)-7-nitro-2,4-dioxo-1,4-dihydro-2H-quinazolin-3-yl]-methanesulfonamide

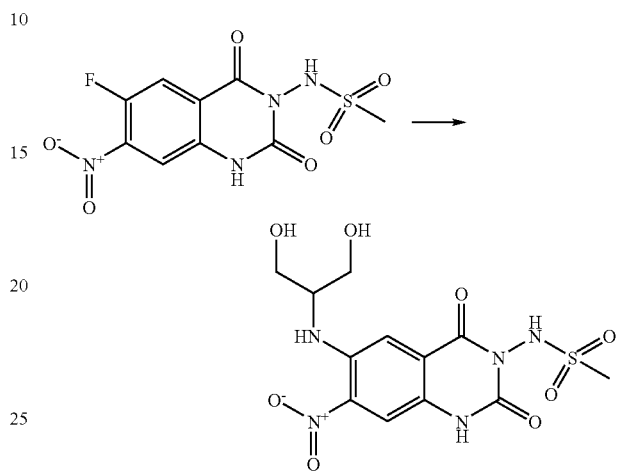

A mixture of 100 mg (0.314 mmol) of N-(6-fluoro-7-nitro-2,4-dioxo-1,4-dihydro-2H-quinazolin-3-yl)-methane-sulfonamide and 142 mg (1.55 mmol) of 2-amino-1,3-propanediol in a closed vial is heated in a microwave reactor at 150° C. for 20 minutes. After cooling, the reaction mixture is concentrated to dryness and the product purified by HPLC-chromatography on a RP-C18 column using a gradient of water/acetonitril/0.1% TFA as eluent. 35 mg of the title compound are obtained as a red powder, m.p. 126-145° C. (decomp.).

In an analogous manner to the previous example, the following compound is prepared:

Example 6

N-[6-(2-Hydroxy-2-thiophen-2-yl-ethylamino)-7-nitro-2,4-dioxo-1,4-dihydro-2H-quinazolin-3-yl]-methanesulfonamide Red powder, m.p. 110° C., decomp.

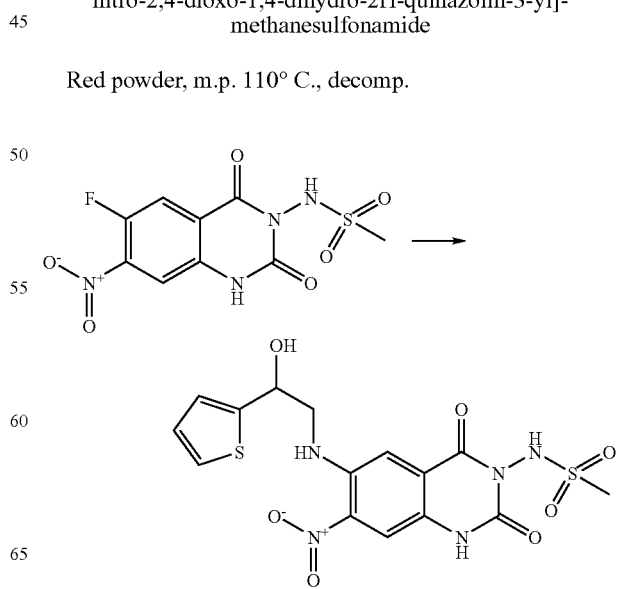

Example 7

N-[7-Nitro-2,4-dioxo-6-(2,2,2-trifluoro-ethylamino)-1,4-dihydro-2H-quinazolin-3-yl]-methanesulfonamide

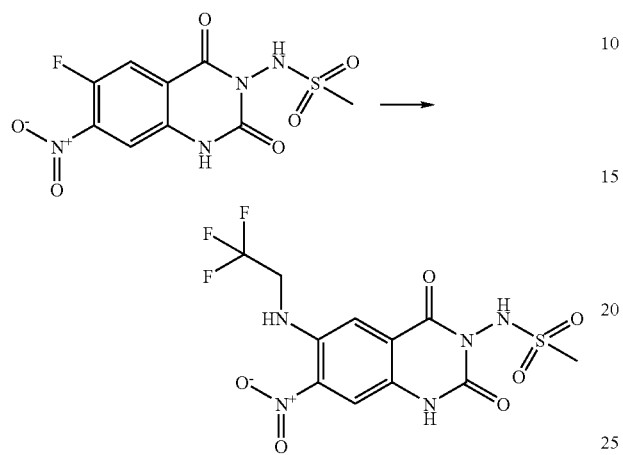

A mixture of 200 mg (0.628 mmol) of N-(6-fluoro-7-nitro-2,4-dioxo-1,4-dihydro-2H-quinazolin-3-yl)-methanesulfonamide and 1.08 ml (13.68 mmol) of 2,2,2-trifluoroethylamine in a closed vial is heated in a microwave reactor at 140° C. for 20 hours. After cooling, the reaction mixture is distributed between ethyl acetate and water, the organic phase dried and concentrated to yield a precipitate which is filtered off and submitted to purification by medium pressure chromatography on a RP-C18 column (20 μM material) with tetrahydrofuran/water 4:3 as eluent, containing 0.1% TFA. During concentration of the fractions the product precipitates and is collected by filtration, giving 63 mg of a red powder, m.p. 250° C. (decomp.).

Example 8

N-(6-Amino-7-nitro-2,4-dioxo-1,4-dihydro-2H-quinazolin-3-yl)-methanesulfonamide

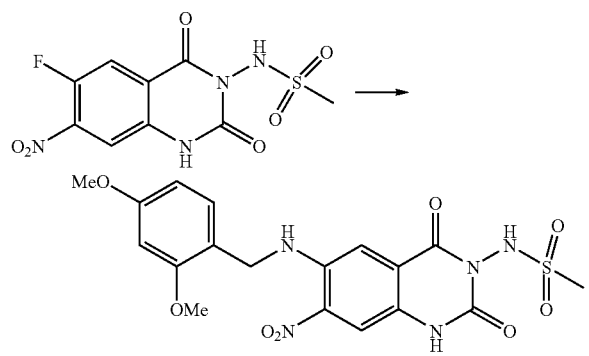

To the yellow solution of N-(6-fluoro-7-nitro-2,4-dioxo-1,4-dihydro-2H-quinazolin-3-yl)-methanesulfonamide (500 mg, 1.57 mmol) in ethanol (0.5 ml) is added 2,4-dimethoxy-benzylamine (4.72 ml, 31.4 mmol) under argon. The solution is heated at 150° in a closed vial in a microwave reactor for 4 minutes. After removal of the solvent and 2,4-dimethoxybenzylamine by high-vacuum rotavapor evaporation the remaining deep purple oil is treated with diethyl ether to obtain a suspension, which is filtered and dried to yield the crude title compound as a deep purple solid, m.p. 232-237° C.

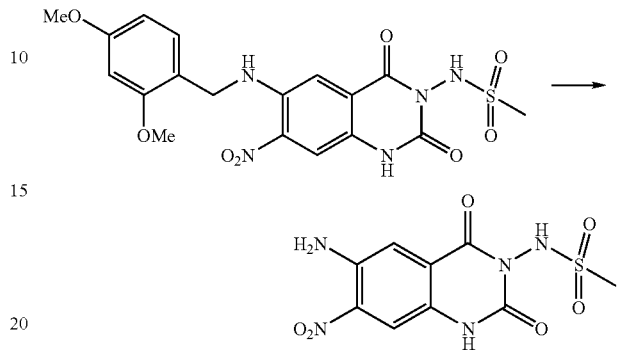

To a solution of N-[6-(2,4-dimethoxy-benzylamino)-7-nitro-2,4-dioxo-1,4-dihydro-2H-quinazolin-3-yl]-methanesulfonamide (725 mg, 1.56 mmol) in dichloromethane (4 ml) is added trifluoroacetic acid (0.5 ml) and the mixture is stirred at room temperature for 30 minutes. Then the solvent is removed by rotavapor evaporation to give an orange solid which is suspended in diethyl ether, filtered and the residue washed 3 times with diethyl ether and two times with ethyl acetate to give the title product as a pure orange solid, m.p. 326-335° C. (decomp.).

Example 9

N-(7-Nitro-2,4-dioxo-6-pyrrol-1-yl-1,4-dihydro-2H-quinazolin-3-yl)-methanesulfonamide

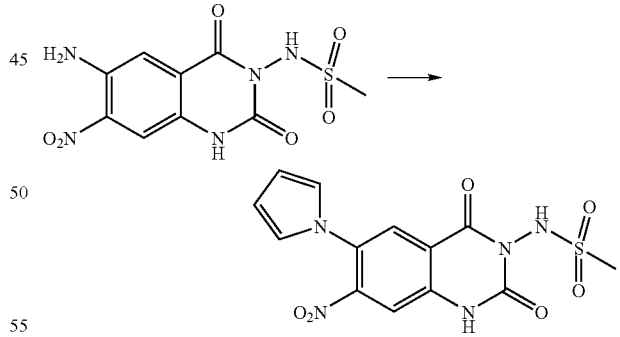

A solution of N-(6-amino-7-nitro-2,4-dioxo-1,4-dihydro-2H-quinazolin-3-yl)-methanesulfonamide (90 mg, 0.285 mmol) and 2,5-dimethoxytetrahydrofuran (0.038 ml, 0.291 mmol) in acetic acid (0.5 ml) is refluxed for 80 minutes. The resulting suspension is filtered and the residue washed with ethyl acetate. The filtrate is concentrated in vacuo to give a brown solid which is suspended in diethyl ether and filtered to give a brown-orange solid as the desired pure product, m.p. 243-250° C.

Example 10

N-[6-(3-Formyl-pyrrol-1-yl)-7-nitro-2,4-dioxo-1,4-dihydro-2H-quinazolin-3-yl]-methanesulfonamide

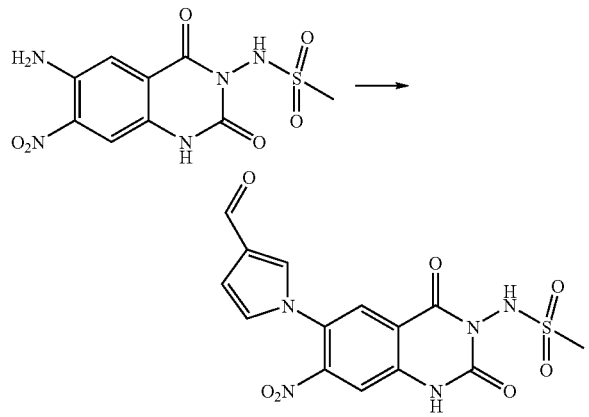

A solution of N-(6-amino-7-nitro-2,4-dioxo-1,4-dihydro-2H-quinazolin-3-yl)-methanesulfonamide (470 mg, 1.49 mmol) and 2,5-dimethoxytetrahydrofuran-3-aldehyde (796 mg, 4.47 mmol) in acetic acid (0.5 ml) is refluxed for five hours. The solvent is removed by rotavapor evaporation to give a brown oil which is dissolved in ethyl acetate and washed three times with water. The organic layer is dried over magnesium sulfate, filtered and the solvent removed by rotavapor evaporation to give the title compound nearly pure as a brown solid, m.p. 230-245° C. (decomp).

Example 11

N-[6-(3-Hydroxymethyl-pyrrol-1-yl)-7-nitro-2,4-dioxo-1,4-dihydro-2H-quinazolin-3-yl]-methanesulfonamide

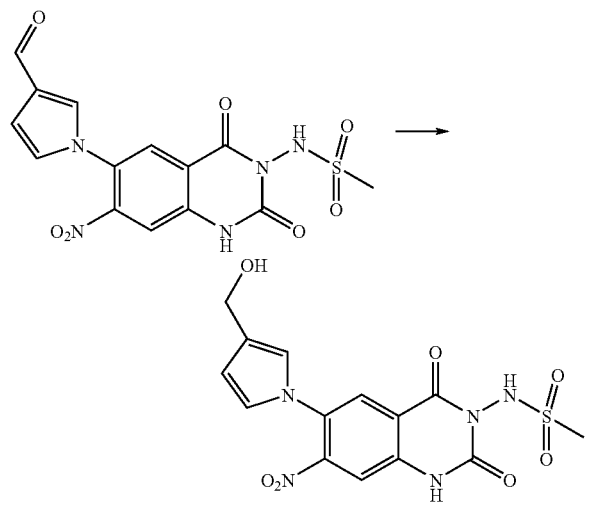

To a solution of N-[6-(3-formyl-pyrrol-1-yl)-7-nitro-2,4-dioxo-1,4-dihydro-2H-quinazolin-3-yl]-methanesulfonamide (580 mg, 1.47 mmol, crude from previous step) in methanol (5 ml) sodium borohydride (112 mg, 2.95 mmol) is added at 0° C. and allowed to stir for 30 minutes. A small quantity of acetic acid is added to destroy excess sodium borohydride. The reaction mixture is diluted with ethyl acetate and washed two times with water and the solvent of the organic layer is removed by rotavapor evaporation to give a red-brown oil which is purified by flash chromatography with DCM/methanol from 98:2 to 95:5 to yield the title compound as an orange solid, m.p. 250-270° C. (decomp.).

Example 12

N-[6-(2-Methoxy-1-methyl-ethylamino)-7-nitro-2,4-dioxo-1,4-dihydro-2H-quinazolin-3-yl]-methanesulfonamide

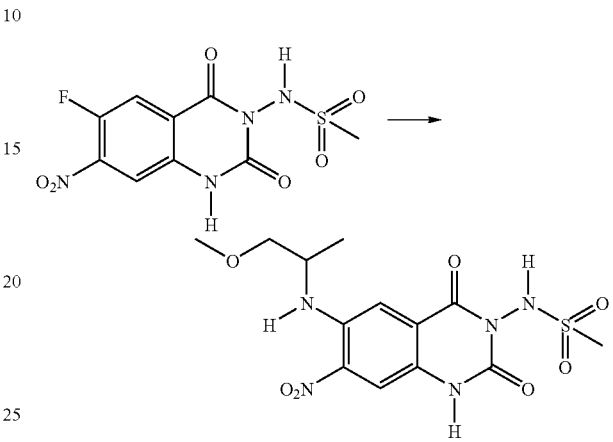

A mixture of 200 mg (0.63 mmol) of N-(6-fluoro-7-nitro-2,4-dioxo-1,4-dihydro-2H-quinazolin-3-yl)-methanesulfonamide, 0.27 ml (2.51 mmol) of 2-methoxy-1-methyl-ethylamine and 3 ml ethanol is heated at 150° C. in a closed vial in a microwave reactor for 15 minutes. After cooling to room temperature, 1M aqueous hydrochloric acid is added until a pH value of 5-6 is reached. The resulting suspension is filtered, the residue washed with water and dried at 60° C. Crystallization from ether-hexane gives 82 mg (34%) of the title compound as red crystals, m.p. 103-111° C.

Example 13

N-[6-(2-Benzyloxy-ethylamino)-7-nitro-2,4-dioxo-1,4-dihydro-2H-quinazolin-3-yl]-methanesulfonamide

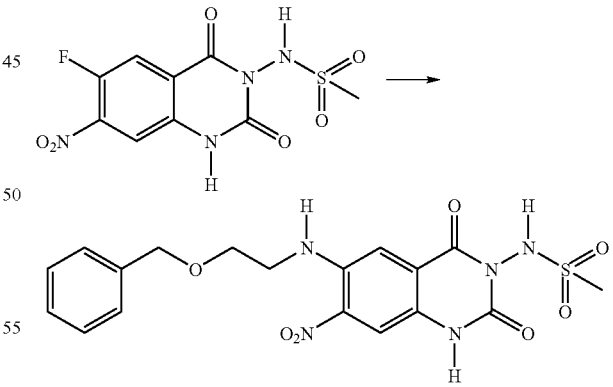

A mixture of 318 mg (1 mmol) of N-(6-fluoro-7-nitro-2,4-dioxo-1,4-dihydro-2H-quinazolin-3-yl)-methanesulfonamide, 605 mg (4.0 mmol) of 2-benzyloxy-ethylamine and 3.2 ml of ethanol is heated at 120° C. in a closed vial in a microwave reactor for 10 minutes. After cooling to room temperature, 1M aqueous hydrochloric acid is added until a pH value of ~3 is reached. The resulting mixture is extracted with ethyl acetate. The organic phase is separated, washed with water and brine, dried over magnesium sulfate and evaporated. Chromatography of the residue on silica with dichloro-methane-methanol (93:7) and crystallization from tetrahydrofuran-hexane gives 261 mg (58%) of the title compound as red crystals, m.p. 204° C. (decomp.).

Example 14

N-(6-Cyclopentylamino-7-nitro-2,4-dioxo-1,4-dihydro-2H-quinazolin-3-yl)-methanesulfonamide

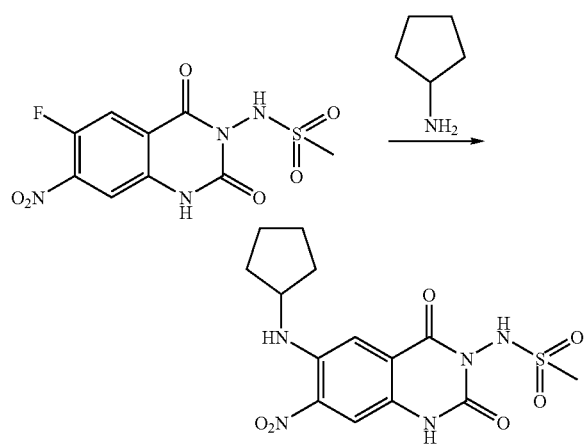

A mixture of 140 mg (0.44 mmol) of N-(6-fluoro-7-nitro-2,4-dioxo-1,4-dihydro-2H-quinazolin-3-yl)-methanesulfonamide, 0.17 ml (1.76 mmol) of cyclopentylamine and 3 ml of ethanol is heated at 150° C. in a closed vial in a microwave reactor for 5 minutes. After cooling to room temperature, water is added and the resulting suspension is filtered. Conc. aqueous hydrochloric acid is added to the filtrate until a pH value of 2-3 is reached and the formed suspension is filtered. The residue is crystallized from ether-hexane to yield 52 mg (31%) of the title compound as red crystals, m.p. 146-155° C.

Example 15

N-(6-Methoxy-7-nitro-2,4-dioxo-1,4-dihydro-2H-quinazolin-3-yl)-methanesulfonamide

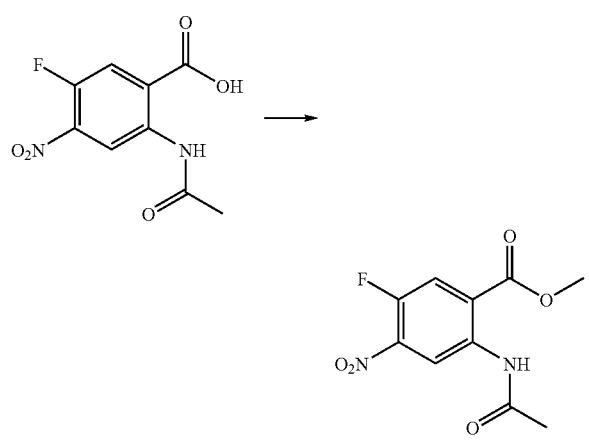

2.06 ml (4.12 mmol) of a 2M solution of diazomethyl-trimethyl-silane in hexane are added with slight cooling at 20° C. to a solution of 1.0 g (4.13 mmol) of 2-acetylamino-5-fluoro-4-nitro-benzoic acid in 15 ml of methanol and 35 ml of benzene. HPLC analysis after 15 minutes shows that there are still about 50% of the starting material present. Additional 2.4 ml (4.8 mmol) of the diazomethyl-trimethyl-silane solution are added. After standing for about 16 hours, no starting material can be detected by HPLC. 0.5 ml of glacial acetic acid are added and the reaction mixture is evaporated to dryness. Toluene is added and the mixture is again evaporated. The resulting residue is dissolved in refluxing ethyl acetate, hexane is added, the formed crystals are filtered, washed with hexane and dried at about 0.01 torr and 50° C. yielding 912 mg (86%) of 2-acetylamino-5-fluoro-4-nitro-benzoic acid methyl ester, m.p. 124-126° C.

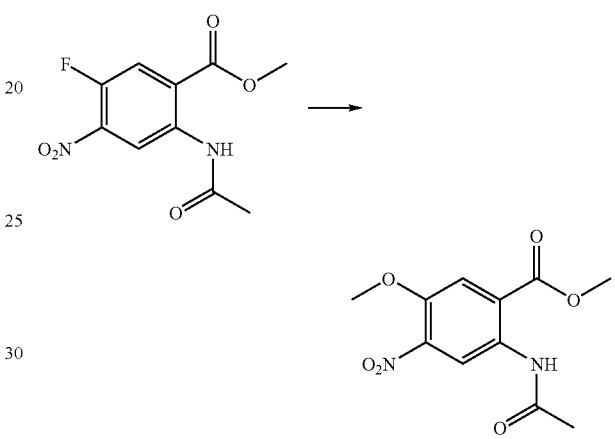

256 mg (1.0 mmol) of 2-acetylamino-5-fluoro-4-nitro-benzoic acid methyl ester are dissolved in 5.1 ml of refluxing methanol abs. and cooled to 23° C. whereby some of the material recrystallizes. 81 mg (1.5 mmol) of sodium methanolate are added and the mixture is stirred under argon at room temperature for 16 hours. Acetic acid is added until a pH value of 5 is reached, the resulting mixture is distributed between ethyl acetate and water, the organic phase is separated, washed with water and brine, dried over sodium sulfate, filtered and evaporated. The residue is chromatographed on 100 g of silica gel (0.04-063 mm) with toluene-ethyl acetate (3:1), fraction size 12 ml. The fractions 37-46 are combined and evaporated, yielding 77 mg (28%) of 2-acetylamino-5-methoxy-4-nitro-benzoic acid methyl ester as yellowish crystals, m.p. 141-143° C.

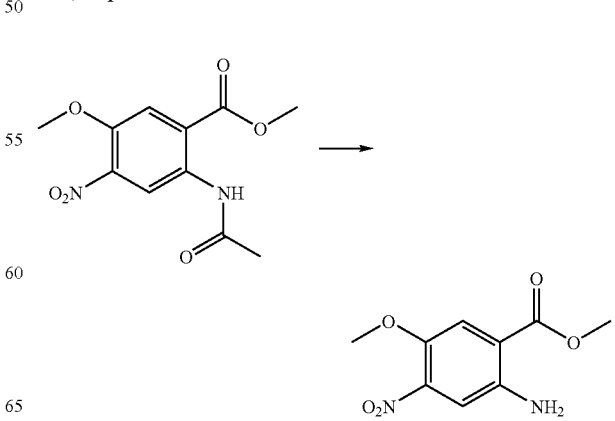

0.12 ml of sulfuric acid 98% are added dropwise at 0° C. (exothermic) to a suspension of 69 mg (0.257 mmol) of 2-acetylamino-5-methoxy-4-nitro-benzoic acid methyl ester, 0.69 ml of methanol and 0.12 ml of water. The mixture is then heated to 70° C. for 30 minutes, cooled to room temperature, poured onto a mixture of ice, water and ethyl acetate and the pH adjusted to 6 with concentrated potassium bicarbonate solution. The organic phase is separated, washed with brine, dried over sodium sulfate, filtered and evaporated, giving 46 mg (79%) of 2-amino-5-methoxy-4-nitro-benzoic acid methyl ester as red-brown crystals, m.p. 127-129° C.

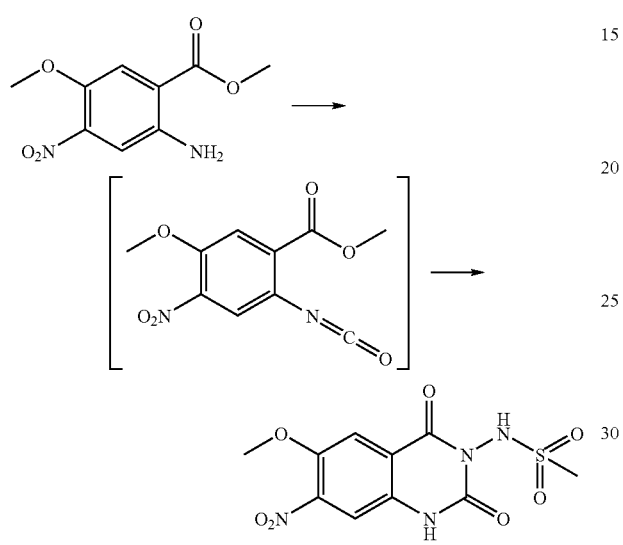

0.5 ml of a solution of phosgene in toluene (20%) are dropped to a suspension of 35 mg (0.155 mmol) of 2-amino-5-methoxy-4-nitro-benzoic acid methyl ester in toluene at −15° C. The mixture is allowed to warm to room temperature during one hour and then heated to reflux. After 45 minutes argon is blown through the refluxing yellow solution for 30 minutes and for 2 hours at room temperature. The reaction mixture is evaporated and the residue dried at room temperature and 9 mbar for 1 hour, leading to 45 mg of crude 2-isocyanato-5-methoxy-4-nitro-benzoic acid methyl ester. 43 mg of this material are suspended in 0.91 ml of tetrahydrofuran abs., 17 mg of methanesulfonyl hydrazide are added and the suspension is stirred at room temperature for one hour. 1.0 ml of tetrahydrofuran abs. and 0.045 ml of Huenig's base are added and stirring is continued at room temperature for 18 hours. The reaction mixture is evaporated, the residue dissolved in a mixture of water and ethyl acetate and the aqueous layer adjusted to pH ~2 by addition of 1M aqueous hydrochloric acid. The organic phase is separated, washed with water and brine, dried over sodium sulfate, filtered and evaporated. The resulting material is crystallized from tetrahydrofuran, 2 ml of toluene and 0.02 ml of Huenig's base are added and the mixture is refluxed for three hours. The reaction mixture is evaporated, 1 ml of water is added and the pH adjusted to 1 by addition of 1 N aqueous hydrochloric acid. The suspension is stirred at room temperature for one hour, then filtered and the residue is washed with water. The remaining crystals are dissolved in refluxing tetrahydrofuran, pentane is added, the formed crystals are filtered and dried in vacuo at 100° C., giving 7 mg (13%) of N-(6-methoxy-7-nitro-2,4-dioxo-1,4-dihydro-2H-quinazolin-3-yl)-methanesulfonamide as light-beige crystals, m.p. >280° C.

Example 16

N-[6-(4-Bromo-imidazol-1-yl)-7-nitro-2,4-dioxo-1,4-dihydro-2H-quinazolin-3-yl]-methanesulfonamide

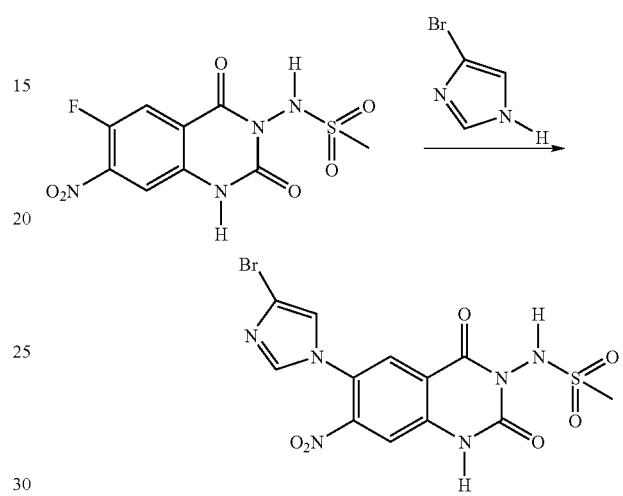

A mixture of 20 mg (0.062 mmol) of N-(6-fluoro-7-nitro-2,4-dioxo-1,4-dihydro-2H-quinazolin-3-yl)-methanesulfonamide, 56 mg (0.372 mmol) of 4-bromo-1H-imidazole and 0.1 ml of DMSO is heated to 120° C. for 16 hours. After cooling to room temperature, the reaction mixture is distributed between ethyl acetate and water, the organic phase is separated, washed with water and brine, dried over sodium sulfate, filtered and evaporated. The residue is chromatographed on silica gel using dichloro-methane-methanol (95:5) and the fractions containing the desired product are combined and evaporated yielding 6 mg (21%) of the title compound. MS (ES−): m/e=445 (M−).

Example 17

N-[7-Nitro-2,4-dioxo-6-(4-phenyl-imidazol-1-yl)-1,4-dihydro-2H-quinazolin-3-yl]-methanesulfonamide

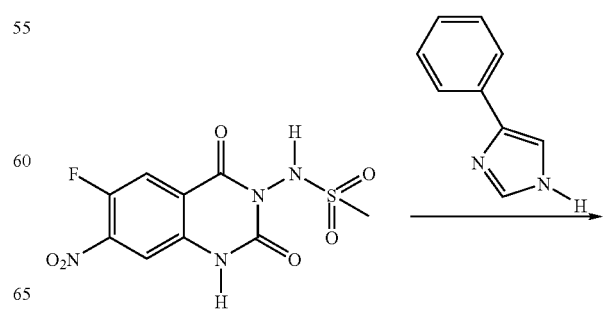

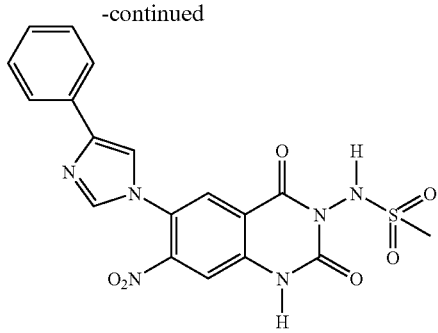

A mixture of 50 mg (0.156 mmol) of N-(6-fluoro-7-nitro-2,4-dioxo-1,4-dihydro-2H-quinazolin-3-yl)-methanesulfonamide, 139 mg (0.936 mmol) of 4-phenyl-1H-imidazole and 0.25 ml of DMSO is heated to 120° C. for 3.5 hours. After cooling to room temperature, the reaction mixture is distributed between ethyl acetate and water, the organic phase is separated, washed with water and brine, dried over sodium sulfate, filtered and evaporated. The residue is chromatographed on silica gel using tetrahydrofuran-hexane (80:20) and the fractions containing the desired product are combined and evaporated giving 53 mg (77%) of the title compound. MS (ES⁻): m/e=441 (M−1⁻).

Example 18

N-{6-[4-(4-Methoxy-phenyl)-imidazol-1-yl]-7-nitro-2,4-dioxo-1,4-dihydro-2H-quinazolin-3-yl}-methanesulfonamide:

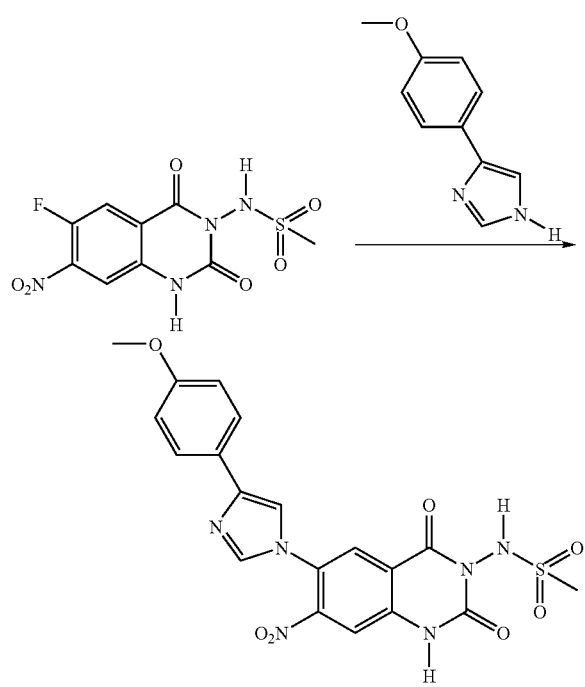

A mixture of 75 mg (0.233 mmol) of N-(6-fluoro-7-nitro-2,4-dioxo-1,4-dihydro-2H-quinazolin-3-yl)-methanesulfonamide, 209 mg (1.165 mmol) of 4-(4-methoxy-phenyl)-1H-imidazole and 0.3 ml of DMSO is heated to 120° C. for 3.5 hours. After cooling to room temperature, the reaction mixture is distributed between ethyl acetate and water, the organic phase is separated, washed with water and brine, dried over sodium sulfate, filtered and evaporated. The residue is chromatographed on silica gel using dichloro-methane-methanol (95:5) and the fractions containing the desired product are combined and evaporated. The residue is crystallized from dichloro-methane, a trace of methanol and isopropyl acetate yielding 56 mg (51%) of the title compound, m.p. 268-271° C.

General Procedure A (GPA):

To a suspension of N-(6-fluoro-7-nitro-2,4-dioxo-1,4-dihydro-2H-quinazolin-3-yl)-methanesulfonamide (30 mg, 0.0943 mmol) in EtOH is added the nucleophile (0.943 mmol, 10 eq.) at room temperature. The reaction mixture turns rapidly yellow-orange and is heated at 150° C. in a microwave reactor for a 6 to 40 minutes timeframe, corresponding to disappearance of the starting material (HPLC monitoring). The solvent is evaporated, the crude material dissolved in DMSO or adsorbed on diatomaceous earth isolute® sorbent HM-N and purified on reverse phase C18 MPLC.

General Procedure B (GPB): To a solution of N-(6-fluoro-7-nitro-2,4-dioxo-1,4-dihydro-2H-quinazolin-3-yl)-methanesulfonamide (30 mg, 0.0943 mmol) in DMSO is added the nucleophile (0.471 mmol, 5 eq.) at room temperature. The reaction mixture is heated at 120° C. under $N_2$ for 16 h. The crude solution is purified on reverse phase C18 MPLC.

HPLC specificity: The retention times ($R_t$) are obtained on a Waters HPLC alliance-HT system with a Macherey-Nagel column CC 70/4.6 Nucleosil 100-3° C.18 applying a gradient water+0.1% TFA/acetonitril+0.1% TFA 5/95 to 95/5 over 8 minutes and 1.4 ml/min. as solvent flow.

Example 19

N-(6-Benzylamino-7-nitro-2,4-dioxo-1,4-dihydro-2H-quinazolin-3-yl)-methanesulfonamide N-(6-Fluoro-7-nitro-2,4-dioxo-1,4-dihydro-2H-quinazolin-3-yl)-methanesulfonamide (20 mg, 0.0628 mmol) is reacted with benzylamine according to the GPA affording 8 mg (31%) of a red powder. $R_t$=3.45 min.

Example 20

N-[6-(4-Fluoro-benzylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 4-fluoro-benzylamine according to the GPA affording 5 mg (12.5%) of a red powder. $R_t$=5.00 min.

Example 21

N-[6-(2-Hydroxy-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-amino-ethanol according to the GPA affording 20 mg (59%) of a red powder. $R_t$=2.86 min.

Example 22

N-[6-(2-Morpholin-4-yl-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (29 mg, 0.0912 mmol) is

Example 23

N-[6-(4-Methoxy-benzylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 4-methoxy-benzylamine according to the GPA affording 24.7 mg (60%) of a red powder. $R_t$=4.97 min.

Example 24

N-{6-[(Benzo[1,3]dioxol-5-ylmethyl)-amino]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (30 mg, 0.0943 mmol) is reacted with benzo[1,3]dioxol-5-yl-methylamine according to the GPA affording 9.1 mg (21.5%) of a red powder. $R_t$=4.86 min.

Example 25

N-[7-Nitro-2,4-dioxo-6-(4-phenyl-piperazin-1-yl)-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 1-phenyl-piperazine according to the GPA affording 28.6 mg (66%) of an orange powder. $R_t$=4.49 min.

Example 26

N-[6-(2-Methyl-imidazol-1-yl)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (25 mg, 0.0786 mmol) is reacted with 2-methyl-1H-imidazole according to the GPA affording 14.5 mg (49%) of a yellowish powder. $R_t$=1.98 min.

Example 27

N-[7-Nitro-2,4-dioxo-6-(4-phenyl-butylamino)-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (20 mg, 0.0628 mmol) is reacted with 4-phenyl-butylamine according to the GPA but purified, due to low solubility, by preparative TLC (eluent: hexane/ethyl acetate/acetic acid, 3/7/0.1) affording 5.4 mg (19%) of a red powder. $R_t$=5.93 min.

Example 28

N-{6-[4-(4-Acetyl-phenyl)-piperazin-1-yl]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (20 mg, 0.0628 mmol) is reacted with 2-morpholin-4-yl-ethylamine according to the GPA affording 21 mg (54%) of a red powder. $R_t$=2.33 min. reacted with 1-(4-piperazin-1-yl-phenyl)-ethanone according to the GPA affording 14 mg (44%) of an orange powder. $R_t$=3.85 min.

Example 29

N-(7-Nitro-2,4-dioxo-6-[1,2,4]triazol-1-yl-1,4-dihydro-2H-quinazolin-3-yl)-methanesulfonamide N-(6-Fluoro-7-nitro-2,4-dioxo-1,4-dihydro-2H-quinazolin-3-yl)-methanesulfonamide (20 mg, 0.0628 mmol) is reacted with 1H-[1,2,4]triazole according to the GPB affording 19 mg (83%) of a yellowish powder. $R_t$=2.87 min.

Example 30

N-[7-Nitro-2,4-dioxo-6-(2-phenoxy-ethylamino)-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (20 mg, 0.0628 mmol) is reacted with 2-phenoxy-ethylamine according to the GPA affording 14 mg (52%) of a red powder. $R_t$=5.25 min.

Example 31

N-[6-(2-Methoxy-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (20 mg, 0.0628 mmol) is reacted with 2-methoxy-ethylamine according to the GPA affording 8.5 mg (36%) of a red powder. $R_t$=3.84 min.

Example 32

N-(7-Nitro-2,4-dioxo-6-pyrazol-1-yl-1,4-dihydro-2H-quinazolin-3-yl)-methanesulfonamide N-(6-Fluoro-7-nitro-2,4-dioxo-1,4-dihydro-2H-quinazolin-3-yl)-methanesulfonamide (30 mg, 0.0943 mmol) is reacted with 1H-pyrazole according to the GPB affording 9.4 mg (27%) of a red powder. $R_t$=3.64 min.

Example 33

N-[6-(4-Methyl-imidazol-1-yl)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (25 mg, 0.0786 mmol) is reacted with 4-methyl-1H-imidazole according to the GPB affording 12.6 mg (43%) of a yellowish powder as a 5 to 1 regioisomer mixture. $R_t$=2.11 min.

Example 34

N-{6-[2-(1H-Imidazol-4-yl)-ethylamino]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (20 mg, 0.0628 mmol) is reacted with 2-(1H-imidazol-4-yl)-ethylamine according to the GPA affording 9.6 mg (37%) of a red powder. $R_t$=2.65 min.

Example 35

N-(6-Cyclopropylamino-7-nitro-2,4-dioxo-1,4-dihydro-2H-quinazolin-3-yl)-methanesulfonamide N-(6-Fluoro-7-nitro-2,4-dioxo-1,4-dihydro-2H-quinazolin-3-yl)-methanesulfonamide (30 mg, 0.0943 mmol) is reacted with cyclopropylamine according to the GPA affording 10 mg (31%) of a red powder. $R_t$=3.15 min.

Example 36

N-[6-(Cyclopropylmethyl-amino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (33 mg, 0.1037 mmol) is reacted with cyclopropyl-methylamine according to the GPA but purified by MPLC (hexane/ethyl acetate/acetic acid, 95/5/01 to 40/60/0.1) affording 11 mg (32%) of a red powder. $R_t$=4.66 min.

Example 37

N-[6-(3-Hydroxy-pyrrolidin-1-yl)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with pyrrolidin-3-ol according to the GPA affording 21 mg (58%) of a red powder. $R_t$=4.22 min.

Example 38

N-[6-(2-Hydroxy-propylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 1-amino-propan-2-ol according to the GPA affording 23.1 mg (65%) of a red powder. $R_t$=3.07 min.

Example 39

N-(6-Isopropylamino-7-nitro-2,4-dioxo-1,4-dihydro-2H-quinazolin-3-yl)-methanesulfonamide N-(6-Fluoro-7-nitro-2,4-dioxo-1,4-dihydro-2H-quinazolin-3-yl)-methanesulfonamide (30 mg, 0.0943 mmol) is reacted with isopropylamine according to the GPA affording 19.6 mg (58%) of a red powder. $R_t$=4.44 min.

Example 40

N-(7-Nitro-2,4-dioxo-6-pyrrolidin-1-yl-1,4-dihydro-2H-quinazolin-3-yl)-methanesulfonamide N-(6-Fluoro-7-nitro-2,4-dioxo-1,4-dihydro-2H-quinazolin-3-yl)-methanesulfonamide (30 mg, 0.0943 mmol) is reacted with pyrrolidine according to the GPA affording 12.2 mg (35%) of an orange-light powder. $R_t$=4.37 min.

Example 41

N-{6-[4-(2-Morpholin-4-yl-2-oxo-ethyl)-imidazol-1-yl]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-(1H-imidazol-4-yl)-1-morpholin-4-yl-ethanone according to the GPB affording 18.1 mg (39%) of a yellow powder. $R_t$=4.37 min

Example 42

N-{6-[(2-Hydroxy-ethyl)-methyl-amino]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-methylamino-ethanol according to the GPA affording 25 mg (71%) of an orange-dark powder. $R_t$=2.98 min.

Example 43

N-[6-(3-Hydroxy-propylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 3-amino-propan-1-ol according to the GPA affording 24.1 mg (68.5%) of a red powder. $R_t$=3.09 min.

Example 44

N-[6-(2-Hydroxy-1-methyl-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-amino-propan-1-ol according to the GPA affording 25 mg (71%) of a red powder. $R_t$=3.21 min.

Example 45

N-[6-(2-Hydroxy-1,1-dimethyl-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-amino-2-methyl-propan-1-ol according to the GPA affording 14.2 mg (39%) of a red powder. $R_t$=3.55 min.

Example 46

N-[6-(4,5-Dimethyl-imidazol-1-yl)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 4,5-dimethyl-1H-imidazole according to the GPB affording 18 mg (48%) of a white powder. $R_t$=2.43 min.

Example 47

N-{6-[Bis-(2-hydroxy-ethyl)-amino]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-(2-hydroxy-ethylamino)-ethanol according to the GPA affording 21 mg (55%) of a red powder. $R_t$=2.36 min.

Example 48

N-Allyl-2-[1-(3-methanesulfonylamino-7-nitro-2,4-dioxo-1,2,3,4-tetrahydro-quinazolin-6-yl)-1H-imidazol-4-yl]-acetamide N-(6-Fluoro-7-nitro-2,4-dioxo-1,4-dihydro-2H-quinazolin-3-yl)-methanesulfonamide (30 mg, 0.0943 mmol) is reacted with N-allyl-2-(1H-imidazol-4-yl)-acetamide according to the GPA affording 28 mg (52%) of a yellowish powder. $R_t$=2.36 min.

Example 49

[2-(3-Methanesulfonylamino-7-nitro-2,4-dioxo-1,2,3,4-tetrahydro-quinazolin-6-ylamino)-ethyl]-carbamic acid tert-butyl ester N-(6-Fluoro-7-nitro-2,4-dioxo-1,4-dihydro-2H-quinazolin-3-yl)-methanesulfonamide (30 mg, 0.0943 mmol) is reacted with (2-amino-ethyl)-carbamic acid tert-butyl ester according to the GPA affording 27 mg (62%) of a red powder. $R_t$=4.43 min.

Example 50

N-[6-(2-Amino-ethylamino)-7-nitro-2,4-dioxo-1,4-dihydro-2H-quinazolin-3-yl]-methanesulfonamide To an ice-cooled solution of [2-(3-Methanesulfonylamino-7-nitro-2,4-dioxo-1,2,3,4-tetrahydro-quinazolin-6-ylamino)-ethyl]-carbamic acid tert-butyl ester (10 mg, 0.022 mmol) in dichloro-methane (0.5 ml) is added trifluoroacetic acid (0.25 ml). The reaction mixture is stirred at 0° C. for 3 h. The mixture is filtered and the resulting red solid dried under vacuum to afford 9 mg (87%) of a red powder. $R_t$=2.13 min.

Example 51

N-[6-(1-Hydroxymethyl-2-methyl-propylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-amino-3-methyl-butan-1-ol according to the GPA affording 17 mg (45%) of a red powder. $R_t$=4.00 min.

Example 52

N-[6-(1-Hydroxymethyl-propylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-amino-butan-1-ol according to the GPA affording 14.5 mg (40%) of a red powder. $R_t$=3.60 min.

Example 53

N-[6-((S)-2-Hydroxy-1-methyl-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with (S)-2-amino-propan-1-ol according to the GPA affording 21.4 mg (61%) of a red powder. $R_t$=3.20 min.

Example 54

N-[6-((R)-2-Hydroxy-1-phenyl-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with (R)-2-amino-2-phenyl-ethanol according to the GPA affording 31.2 mg (75%) of a red powder. $R_t$=4.11 min.

Example 55

N-[6-((S)-3-Hydroxy-pyrrolidin-1-yl)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with (S)-pyrrolidin-3-ol according to the GPA affording 25 mg (69%) of a red powder. $R_t$=3.11 min.

Example 56

N-[6-((R)-3-Hydroxy-pyrrolidin-1-yl)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with (R)-pyrrolidin-3-ol according to the GPA affording 25.6 mg (60%) of a red powder. $R_t$=3.09 min.

Example 57

N-(6-Azetidin-1-yl-7-nitro-2,4-dioxo-1,4-dihydro-2H-quinazolin-3-yl)-methanesulfonamide N-(6-Fluoro-7-nitro-2,4-dioxo-1,4-dihydro-2H-quinazolin-3-yl)-methanesulfonamide (30 mg, 0.0943 mmol) is reacted with azetidine according to the GPA affording 15 mg (45%) of a red powder. $R_t$=3.92 min.

Example 58

N-{6-[(R)-1-(3,4-Dimethoxy-phenyl)-2-hydroxy-ethylamino]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (30 mg, 0.0943 mmol) is reacted with (R)-2-amino-2-(3,4-dimethoxy-phenyl)-ethanol according to the GPA affording 24.8 mg (53%) of a red powder. $R_t$=3.80 min.

Example 59

N-[6-(1-Hydroxymethyl-pentylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-amino-hexan-1-ol according to the GPA affording 24 mg (61%) of a purple powder. $R_t$=4.5 min.

Example 60

N-(7-Nitro-2,4-dioxo-6-[1,2,3]triazol-1-yl-1,4-dihydro-2H-quinazolin-3-yl)-methanesulfonamide N-(6-Fluoro-7-nitro-2,4-dioxo-1,4-dihydro-2H-quinazolin-3-yl)-methanesulfonamide (30 mg, 0.0943 mmol) is reacted with 1H-[1,2,3]triazole according to the GPB affording 8.5 mg (25%) of a white powder. $R_t$=4.5 min.

Example 61

N-{6-[(S)-2-Hydroxy-1-(1H-imidazol-4-ylmethyl)-ethylamino]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (30 mg, 0.0943 mmol) is reacted with (S)-2-amino-3-(1H-imidazol-4-yl)-propan-1-ol according to the GPA affording 24.1 mg (46%) of a red powder. $R_t$=1.73 min.

Example 62

N-[6-((S)-2-Hydroxy-1-phenyl-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with (S)-2-amino-2-phenyl-ethanol according to the GPA affording 25.8 mg (76%) of a red powder. $R_t$=4.10 min.

Example 63

N-[6-((R)-1-Hydroxymethyl-2-phenyl-ethylamino)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with (R)-2-amino-3-phenyl-propan-1-ol according to the GPA affording 22.2 mg (65%) of a purple powder. $R_t$=4.40 min.

Example 64

N-{6-[2-Hydroxy-1-(1H-indol-3-ylmethyl)-ethylamino]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (30 mg, 0.0943 mmol) is reacted with 2-amino-3-(1H-indol-3-yl)-propan-1-ol according to the GPA affording 18.8 mg (33%) of a red powder. $R_t$=4.27 min.

Example 65

N-{6-[(R)-2-Hydroxy-1-(1H-imidazol-4-ylmethyl)-ethylamino]-7-nitro-2,4-dioxo-1,4-dihydro-2H-quinazolin-3-yl}-methanesulfonamide N-(6-Fluoro-7-nitro-2,4-dioxo-1,4-dihydro-2H-quinazolin-3-yl)-methanesulfonamide (30 mg, 0.0943 mmol) is reacted with (R)-2-amino-3-(1H-imidazol-4-yl)-propan-1-ol according to the GPA affording 22.7 mg (43%) of a red powder. $R_t$=1.73 min.

Example 66

N-[6-(4-Cyanomethyl-imidazol-1-yl)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (30 mg, 0.0943 mmol) is reacted with (1H-imidazol-4-yl)-acetonitrile according to the GPB affording 18.5 mg (47%) of a yellow powder. $R_t$=2.56 min.

Example 67

N-[6-(4-Methoxymethyl-imidazol-1-yl)-7-nitro-2,4-dioxo-1,4-dihydro-2H-quinazolin-3-yl]-methanesulfonamide N-(6-Fluoro-7-nitro-2,4-dioxo-1,4-dihydro-2H-quinazolin-3-yl)-methanesulfonamide (50 mg, 0.157 mmol) is reacted with 4-methoxymethyl-1H-imidazole according to the GPB affording 36 mg (44%) of a yellow powder. $R_t$=2.20 min.

Example 68

N-(6-Morpholin-4-yl-2,4-dioxo-7-trifluoromethyl-1,4-dihydro-2H-quinazolin-3-yl)-methanesulfonamide

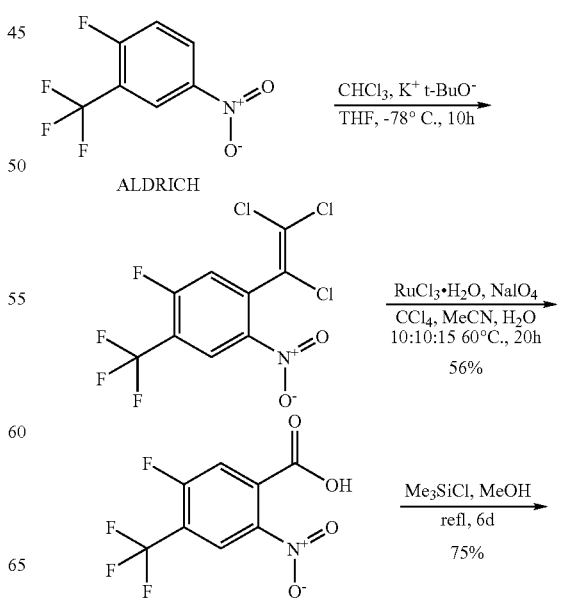

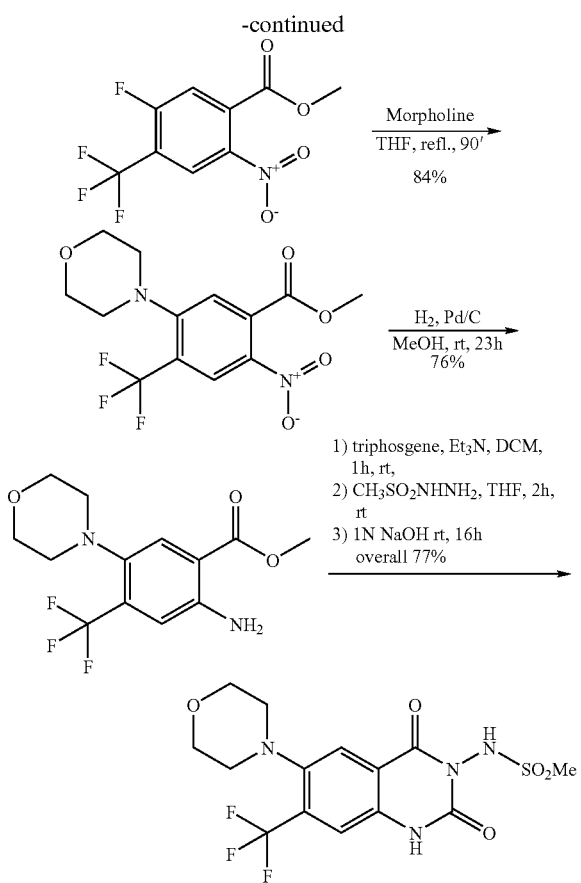

70 mg (0.23 mmole) of 2-amino-5-morpholin-4-yl-4-trifluoromethyl-benzoic acid methyl ester are dissolved in 5 ml of dichloro-methane and treated with 23 mg (0.076 mmole) of triphosgene. 15 minutes later are added 0.025 ml of triethylamine to the suspension. The clear solution is stirred for additional three hours at room temperature, after which a solution of 26 mg (0.23 mmole) methanesulphonyl hydrazide in 2.5 ml of dry tetrahydrofuran is added via a syringe. The resulting suspension is stirred for an additional hour at room temperature, treated with 0.3 ml of a 1M aqeous sodium hydroxide solution and stirred overnight. After evaporation of the solvent using a rotatory evaporator the residue is dissolved in dichloro-methane and purified over preparative thin layer chromatography plates using a solvent mixture of dichloromethane/methanol 9:1 to yield N-(6-morpholin-4-yl-2,4-dioxo-7-trifluoro-methyl-1,4-dihydro-2H-quinazolin-3-yl)-methanesulfonamide of m.p. 255-260° C.

The starting material 2-amino-5-morpholin-4-yl-4-trifluoromethyl-benzoic acid methyl ester is prepared as follows:

A solution of 20 g (0.173 moles) of potassium tertiary butoxide in 300 ml of dry tetrahydrofuran is cooled to −78° C. under a nitrogen atmosphere. A solution of 10 g (46.87 mmole) of 1-fluoro-4-nitro-2-trifluoromethyl-benzene and 8.1 ml (0.1 mole) of chloroform in 100 ml dry tetrahydrofuran is added slowly while keeping the temperature below −75° C. The dark brown solution is treated sequentially with additional 4 ml of chloroform and a solution of 10 g of potassium tertiary butoxide in 100 ml tetrahydrofuran. After 3 hours at −78° C. the solution is stirred until it reached room temperature and is evaporated to dryness. 100 ml of a 1:1 mixture of acetic acid and methanol are added. The residue is dissolved in 500 ml of ethyl acetate and extracted three times with 100 ml of aqueous saturated sodium chloride solution. The organic phase is dried over sodium sulfate, filtered and evaporated. After chromatography on 400 grams of silica gel and elution with dichloro-methane/methanol 9:1 pure 1-fluoro-4-nitro-5-trichlorovinyl-2-trifluoromethyl-benzene is obtained as yellow oil.

To 300 ml of a solvent mixture of tetrachloromethane, acetonitril and water (10:10:15) are added sequentially 8.5 g (25 mmole) of 1-fluoro-4-nitro-5-trichlorovinyl-2-trifluoromethyl-benzene, 1 g (8 mol%) of ruthenium trichloride monohydrate and 23 g (0.1 mole) of sodium periodate. After stirring at 60° C. for 16 hours additional 1 g of ruthenium trichloride monohydrate and 23 g of sodium periodate are added and stirring at 60° C. is continued for 4 hours. The cooled reaction is filtered over Celite and the filtrate evaporated to dryness. 150 ml of a 1M sodium hydroxide solution are added and extracted two times with 150 ml of dichloromethane. The aqueous phase is acidified with concentrated hydrochloric acid and extracted four times with 100 ml dichloro-methane. The combined organic phases are dried over sodium sulfate, filtered and evaporated. The residue is recrystallized from acetone/petrolether to give 5-fluoro-2-nitro-4-trifluoromethyl-benzoic acid of m.p. 142-145° C.

A solution of 6.2 g (24.5 mmole) of 5-fluoro-2-nitro-4-trifluoromethyl-benzoic acid in 250 ml of methanol is treated with 9.28 ml (73.5 mmole) of trimethylchlorosilane and heated to reflux for six days during which every evening additional 9.28 ml of trimethylchlorosilane are added. The cooled solution is evaporated in vacuo and distributed between dichloro-methane and water. The combined organic phases are extracted twice with 50 ml of a 0.5 M sodium hydroxide solution and with 50 ml brine. After drying over sodium sulfate, filtering and evaporation the crystalline residue is recrystallized from acetone/petrolether to give 5-fluoro-2-nitro-4-trifluoromethyl-benzoic acid methyl ester of m.p. 66-68° C.

A solution of 134 mg (0.5 mmole) of 5-fluoro-2-nitro-4-trifluoromethyl-benzoic acid methyl ester in 5 ml of dry tetrahydrofuran is treated with 0.05 ml (0.55 mmole) of morpholine and heated to reflux for 90 minutes. After evaporation of the solvent 5-morpholin-4-yl-2-nitro-4-trifluoromethyl-benzoic acid methyl ester is obtained as a yellow oil.

A solution of 140 mg (0.42 mmole) of 5-morpholin-4-yl-2-nitro-4-trifluoromethyl-benzoic acid methyl ester in 10 ml methanol is treated with 30 mg of 10% palladium on charcoal and hydrogenated at room temperature under a pressure of 5 bar for 23 hours. After filtration of the catalyst and evaporation of the solvent pure 2-amino-5-morpholin-4-yl-4-trifluoromethyl-benzoic acid methyl ester is obtained as a yellow oil.

Example 69

N-(2,4-Dioxo-6-[1,2,4]triazol-4-yl-7-trifluoromethyl-1,4-dihydro-2H-quinazolin-3-yl)-methanesulfonamide

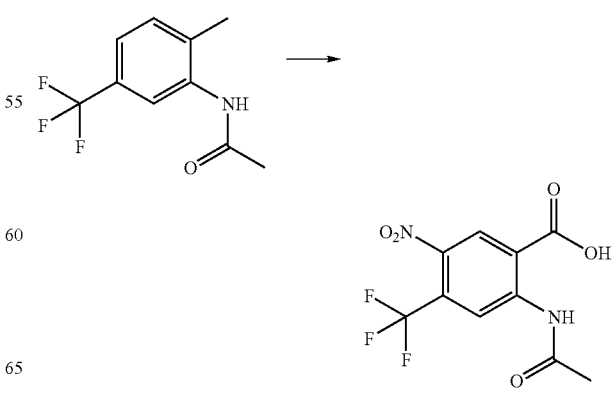

A solution of 65.0 g (300 mmol) of N-(2-methyl-5-trifluoromethyl-phenyl)-acetamide in 520 ml of concentrated H₂SO₄ is treated dropwise with a solution of 152.5 g (1.5 mol) of potassium nitrate in 520 ml of concentrated H₂SO₄ under N₂ and the mixture is kept at room temperature with an ice-bath. The mixture is then stirred for another 2 hours at room temperature and then poured onto ice. The suspension is filtered and the filter cake is dissolved in ethyl acetate, dried over anhydrous Na₂SO₄, filtered and concentrated in vacuo. Crude product is purified by flash chromatography (SiO₂, hexane/ethyl acetate 1:1) to furnish the nitration product as a mixture of regioisomers (62.44 g, 238 mmol). 51.0 g (195 mmol) of this crude product are dissolved in 1000 ml water and heated to 100° C. and treated portionwise with a mixture of 184 g (1167 mmol) of potassium permanganate and 70.4 g (585 mmol) of magnesium sulfate monohydrate. The mixture is kept at 100° C. for another 2 hours and then allowed to cool to room temperature. The mixture is then filtered and the filtrated is extracted with ethyl acetate. The organic phase is dried over anhydrous Na₂SO₄, filtered and concentrated in vacuo to give 19.3 g (27% over 2 steps) of 2-acetylamino-5-nitro-4-trifluoromethyl-benzoic acid as yellow crystals. ¹H-NMR (DMSO-d₆, 400 MHz) 9.13 (s, 1H), 8.67 (s, 1H), 1.98 (s, 3H).

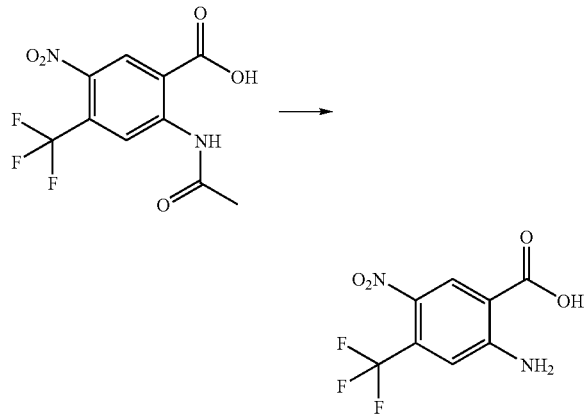

A solution of 49.5 g (169 mmol) of 2-acetylamino-5-nitro-4-trifluoromethyl-benzoic acid in 600 ml of methanol and 100 ml of water is cooled to 0° C. and 71.1 ml (1.33 mol) of concentrated H₂SO₄ are added dropwise. Upon completion of the addition, the mixture is heated to reflux for 1 hour. The mixture is then cooled to 0° C., the pH is adjusted to 10 with a 30% aqueous NaOH-solution and it is stirred for 1 hour. The methanol is distilled off and the remaining aqueous solution is diluted with water and extracted with t-butyl methylether. The aqueous phase is acidified with concentrated HCl-solution and the resulting yellow suspension is filtered and washed with water. The solid is dried in vacuo at 100° C. to give 28.3 g (67%) of 2-amino-5-nitro-4-trifluoromethyl-benzoic acid, m.p. 237° C.

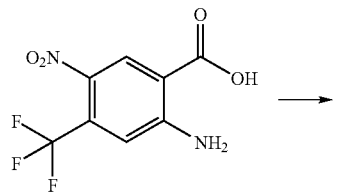

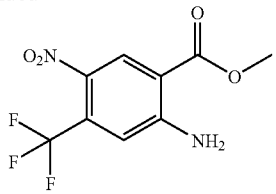

A solution of 28 g (112 mmol) of 2-amino-5-nitro-4-trifluoromethyl-benzoic acid in 550 ml of methanol is cooled to 0° C. under nitrogen and concentrated H₂SO₄ is added dropwise in order to keep the temperature around 20° C. Upon completion of the addition, the mixture is heated to reflux for 24 hours. It is then allowed to cool to room temperature and the mixture is concentrated in vacuo to about 50 ml. This residue is poured onto ice and extracted with ethyl acetate. The organic phase is washed with a saturated aqueous solution of NaHCO₃ and brine, dried over Na₂SO₄, filtered and concentrated in vacuo. The crude product is recrystallized in toluene to give 26.7 g (90%) of 2-amino-5-nitro-4-trifluoromethyl-benzoic acid methyl ester as yellow crystals, m.p. 174-175° C.

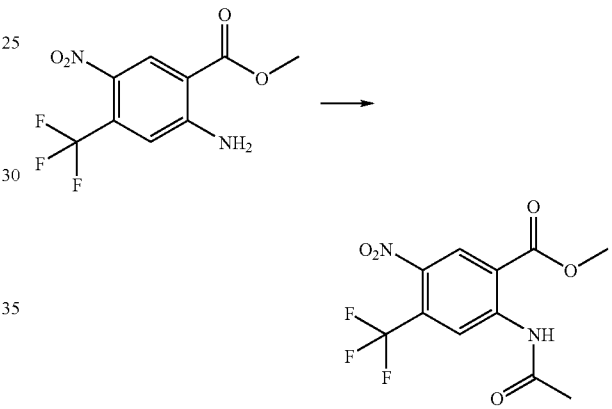

A solution of 2.0 g (7.57 mmol) of 2-amino-5-nitro-4-trifluoromethyl-benzoic acid methyl ester in 20 ml of acetic anhydride is heated to reflux for 4 hours. The mixture is allowed to cool to room temperature and concentrated in vacuo. The residue is taken up in ethyl acetate and washed with water, aqueous saturated NaHCO₃-solution and brine. The organic phase is dried over Na₂SO₄, filtered and concentrated in vacuo. Purification by flash chromatography (SiO₂, hexane/ethyl acetate 3:1) provided 1.79 g (77%) of 2-acetylamino-5-nitro-4-trifluoromethyl-benzoic acid methyl ester as yellow crystals, m.p. 75-80° C.

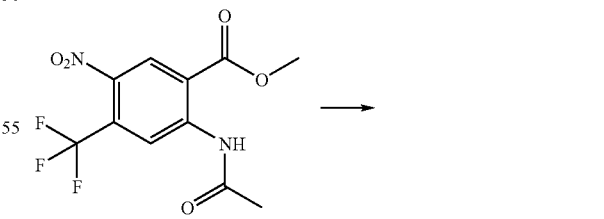

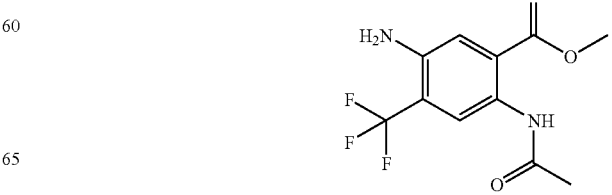

A solution of 1.7 g (5.55 mmol) of 2-acetylamino-5-nitro-4-trifluoromethyl-benzoic acid methyl ester in 29 ml of methanol is treated with 250 mg of Pd/C (10%) and the mixture stirred under 5 bars of hydrogen for 20 minutes. The mixture is filtered and the filtrate concentrated in vacuo to give 1.58 g (quantitative) of 2-acetylamino-5-amino-4-trifluoromethyl-benzoic acid methyl ester as yellow crystals, m.p. 143-152° C.

A solution of 1.3 g (4.14 mmol) of 2-acetylamino-5-[1,2,4]triazol-4-yl-4-trifluoromethyl-benzoic acid in 15 ml of methanol is treated dropwise with 3.1 ml (6.21 mmol) of a 2M solution of trimethylsilyl diazomethane in hexane. The mixture is stirred for 1 hour at room temperature and another 1.5 ml (3.00 mmol) of a solution of trimethylsilyl diazomethane in hexane (2M) is added. After 1 hour, the reaction is quenched by adding glacial acetic acid until no more gas evolution is observed. The mixture is concentrated in vacuo and the residue taken up in ethyl acetate, washed with water, dried over $Na_2SO_4$, filtered and concentrated in vacuo. Purification by flash chromatography ($SiO_2$, gradient 100% ethyl acetate to ethyl acetate/methanol 9:1) afforded 456 mg (34%) of 2-acetylamino-5-[1,2,4]triazol-4-yl-4-trifluoromethyl-benzoic acid methyl ester as yellow crystals, m.p. 180-184° C.

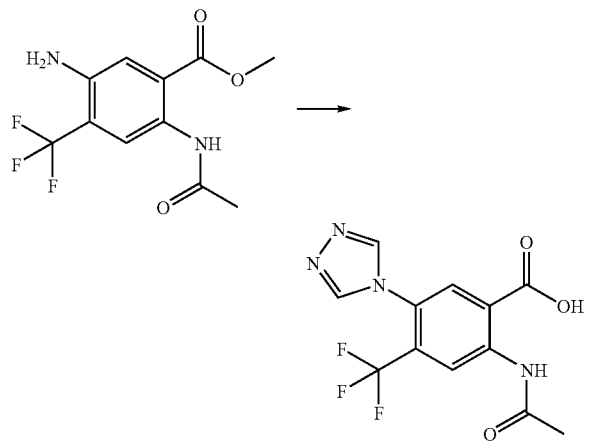

A solution of 1.55 g (5.6 mmol) of 2-acetylamino-5-amino-4-trifluoromethyl-benzoic acid methyl ester, 1.48 g (16.8 mmol) of 1,2-diformylhydrazine, and 5.5 ml (39.2 mmol) of triethylamine in 40 ml of pyridine is treated dropwise with 10.8 ml (85.3 mmol) of trimethylsilyl chloride. The mixture is then heated to 100° C. for 18 hours and allowed to cool to room temperature. It is then treated with another 1.48 g (16.8 mmol) of 1,2-diformylhydrazine, 5.5 ml (39.2 mmol) of triethylamine and 10.8 ml (85.3 mmol) of trimethylsilyl chloride and heated to 100° C. for 24 hours. The mixture is cooled to room temperature, concentrated in vacuo and the residue taken up into water and extracted with ethyl acetate. The aqueous phase is acidified to pH 4-5 with 4M aqueous HCl-solution and saturated with sodium chloride. This aqueous phase is extracted with ethyl acetate and this organic phase is dried over $Na_2SO_4$, filtered and concentrated in vacuo. The crude product is recrystallized in ethyl acetate providing 1.34 g (76%) of 2-acetylamino-5-[1,2,4]triazol-4-yl-4-trifluoromethyl-benzoic acid, MS (ESI): m/e=315 [M+H].

A solution of 450 mg (1.43 mmol) of 2-acetylamino-5-[1,2,4]triazol-4-yl-4-trifluoromethyl-benzoic acid methyl ester in 5 ml methanol and 1 ml water is cooled to 0° C. and treated dropwise with 0.6 ml (11.3 mmol) of concentrated $H_2SO_4$. The mixture is then heated to reflux for 30 minutes and allowed to cool to room temperature. It is poured onto ice and the resulting mixture extracted with ethyl acetate. The organic phase is dried over $Na_2SO_4$, filtered and concentrated in vacuo. The crude product is recrystallized in ethyl acetate/hexane to give 292 mg (71%) of 2-amino-5-[1,2,4]triazol-4-yl-4-trifluoromethyl-benzoic acid methyl ester, m.p. 184-186° C.

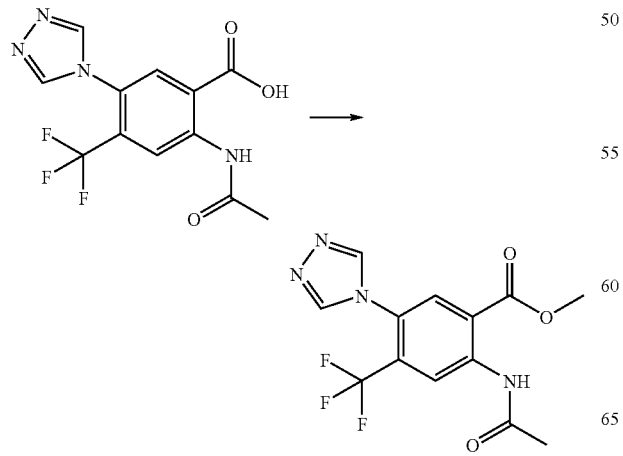

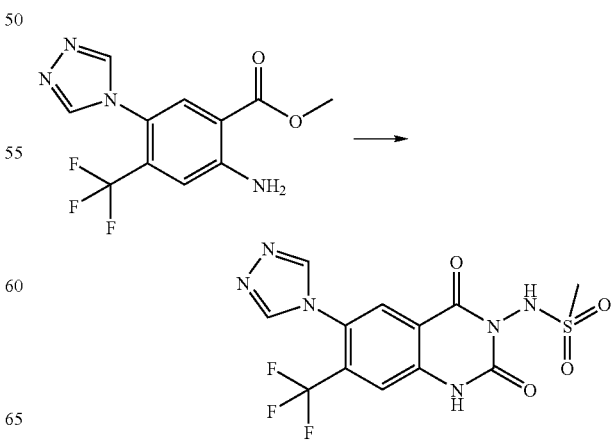

A solution of 270 mg (0.94 mmol) of 2-amino-5-[1,2,4]triazol-4-yl-4-trifluoromethyl-benzoic acid methyl ester in 5 ml of tetrahydrofuran at room temperature under N₂ is treated with 93 mg (0.31 mmol) of triphosgene. The mixture is stirred for 10 minutes and 0.13 ml (0.94 mmol) of triethylamine are added and the stirring is continued for 3 hours. 104 mg (0.94 mmol) of methanesulfonyl hydrazide are then added and the mixture is stirred for 1 hour at room temperature. The mixture is then treated with 2 ml of 1 M aqueous NaOH solution and stirred for additional 2 hours. The pH of the mixture is adjusted to 4-5 with 4 M aqueous HCl solution and the mixture is concentrated in vacuo. The residue is taken up into ethyl acetate and washed with water, dried over Na₂SO₄, filtered and concentrated in vacuo. The crude product is recrystallized in ethyl acetate affording 219 mg (56%) of N-(2,4-dioxo-6-[1,2,4]triazol-4-yl-7-trifluoromethyl-1,4-dihydro-2H-quinazolin-3-yl)-methanesulfonamide as colorless crystals, m.p. 231-237° C.

Example 70

Ethanesulfonic acid (2,4-dioxo-6-[1,2,4]triazol-4-yl-7-trifluoromethyl-1,4-dihydro-2H-quinazolin-3-yl)-amide

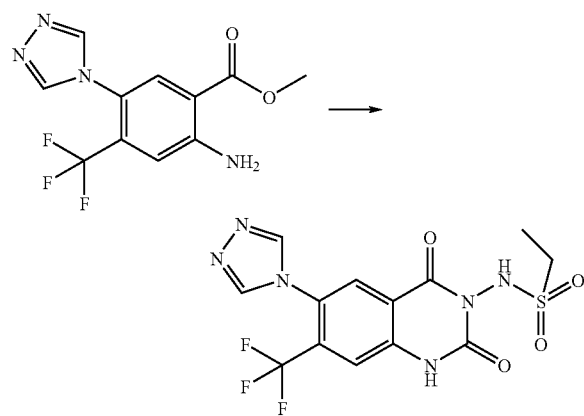

A solution of 650 mg (2.27 mmol) of 2-amino-5-[1,2,4]triazol-4-yl-4-trifluoromethyl-benzoic acid methyl ester in 15 ml of tetrahydrofuran at room temperature under N₂ is treated with 225 mg (0.76 mmol) of triphosgene. The mixture is stirred for 20 minutes and 0.32 ml (2.27 mmol) of triethylamine are added and the stirring continued for 3 hours. 282 mg (2.27 mmol) of ethanesulfonyl hydrazide (prepared in analogy to the method described by J. W. Powell and M. C. Whiting: *The decomposition of sulphonylhydrazone salts—I*, Tetrahedron Vol. 7 (1959) 305)) are added and the mixture stirred for 1 hour at room temperature. The mixture is then treated with 5 ml of 1 M aqueous NaOH solution and stirred for 18 hours. The pH of the mixture is adjusted to 4-5 with 4 M aqueous HCl solution and the mixture is concentrated in vacuo. The crude product is purified by flash chromatography (SiO₂, ethyl acetate/methanol 19:1) furnishing colorless crystals which are recrystallized in ethyl acetate/hexane to afford 462 mg of ethanesulfonic acid (2,4-dioxo-6-[1,2,4]triazol-4-yl-7-trifluoromethyl-1,4-dihydro-2H-quinazolin-3-yl)-amide as colorless crystals, m.p. 185-195° C.

Example 71

1-(3-Methanesulfonylamino-2,4-dioxo-7-trifluoromethyl-1,2,3,4-tetrahydro-quinazolin-6-yl)-1H-[1,2,4]triazole-3-carboxylic acid ethyl ester

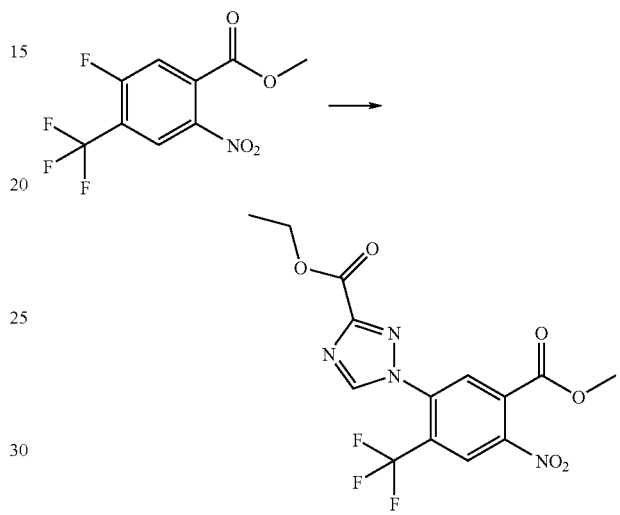

A solution of 613 mg (14.0 mmol) of sodium hydride in 10 ml of 1-methyl-2-pyrrolidinone is cooled to 0-5° C. and treated dropwise with a solution of 1.74 g (12.4 mmol) of 1H-[1,2,4]triazole-3-carboxylic acid ethyl ester in 10 ml of 1-methyl-2-pyrrolidinone over 8 minutes. The mixture is stirred for 1 hour at 0-5° C. and a solution of 3.00 g (11.2 mmol) of 5-fluoro-2-nitro4-trifluoromethyl-benzoic acid methyl ester in 10 ml of 1-methyl-2-pyrrolidinone is added. The mixture is allowed to warm slowly to room temperature and stirred for 18 hours under N₂. It is poured into water and extracted with ethyl acetate. The organic phase is separated and dried over Na₂SO₄, filtered and concentrated in vacuo. The residue is purified by flash chromatography (SiO₂, hexane/ethyl acetate 1:1) and the mixed fractions are recrystallized in toluene to provide overall 3.12 g (71%) of 1-(5-methoxycarbonyl-4-nitro-2-trifluoromethyl-phenyl)-1H-[1,2,4]triazole-3-carboxylic acid ethyl ester, m.p. 190-192° C.

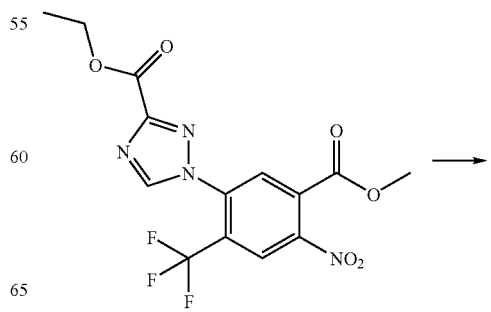

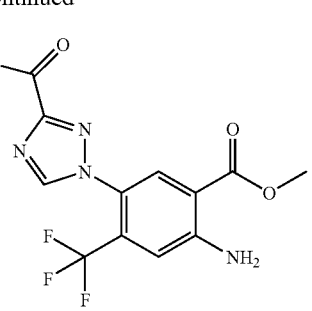

A solution of 3.00 g (7.73 mmol) of 1-(5-methoxycarbonyl-4-nitro-2-trifluoromethyl-phenyl)-1H[1,2,4]triazole-3-carboxylic acid ethyl ester in 75 ml of methanol/tetrahydrofuran (1:1) is treated with 400 mg of Pd/C (10%) and the mixture is stirred under 5 bars of $H_2$ for 30 min. The mixture is then filtered and the filtrate is concentrated in vacuo. The crude product is recrystallized in iso-propanol giving 2.47 g (82%) of 1-(4-amino-5-methoxycarbonyl-2-trifluoromethylphenyl)-1H-[1,2,4]triazole-3-carboxylic acid ethyl ester as white crystals, m.p. 189-190° C.

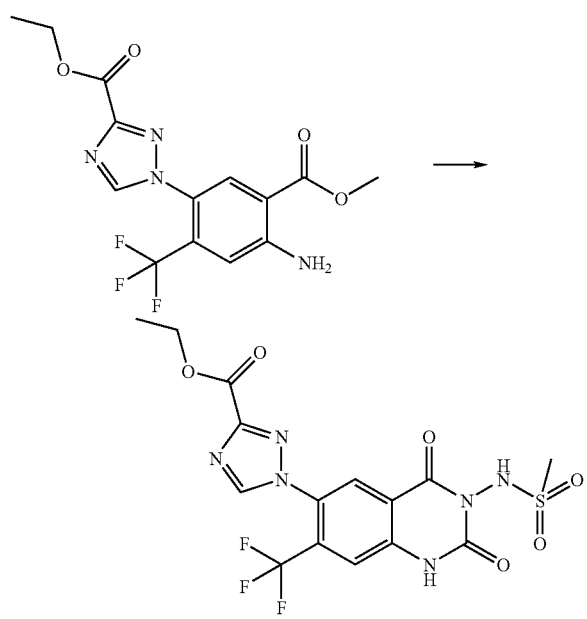

A solution of 1.07 g (3.00 mmol) of 1-(4-amino-5-methoxycarbonyl-2-trifluoromethylphenyl)-1H-[1,2,4]triazole-3-carboxylic acid ethyl ester in 9 ml dichloromethane is treated with 296 mg (1.00 mmol) of triphosgene at room temperature under Ar. The mixture is stirred for 15 minutes and 0.42 ml (3.00 mmol) of triethylamine are added dropwise. The mixture is stirred for 3 hours and a solution of 330 mg (3.00 mmol) of methanesulfonyl hydrazide in 3.3 ml of anhydrous tetrahydrofuran is added. The mixture is stirred for 17 hours at room temperature under Ar. The suspension is filtered, washed with dichloromethane and water and dried in vacuo. These colorless crystals are dissolved in 20 ml anhydrous dioxane and treated with 0.83 ml (4.86 mmol) of ethyldiisopropyl-amine at room temperature under Ar. The mixture is stirred for 17 hours and then concentrated in vacuo. The residue is taken up in ethyl acetate and water and the pH is adjusted to 3-4 with 1M aqueous HCl solution. The organic phase is separated, washed twice with brine, dried over anhydrous $Na_2SO_4$, filtered and concentrated in vacuo. The crude product is recrystallized in tetrahydrofuran/hexane providing 855 mg (62%) of 1-(3-methanesulfonylamino-2,4-dioxo-7-trifluoromethyl-1,2,3,4-tetrahydro-quinazolin-6-yl)-1H-[1,2,4]triazole-3-carboxylic acid ethyl ester as colorless crystals, m.p. 267-270° C.

Example 72

1-(3-Methanesulfonylamino-2,4-dioxo-7-trifluoromethyl-1,2,3,4-tetrahydro-quinazolin-6-yl)-1H-[1,2,4]triazole-3-carboxylic acid methylamide

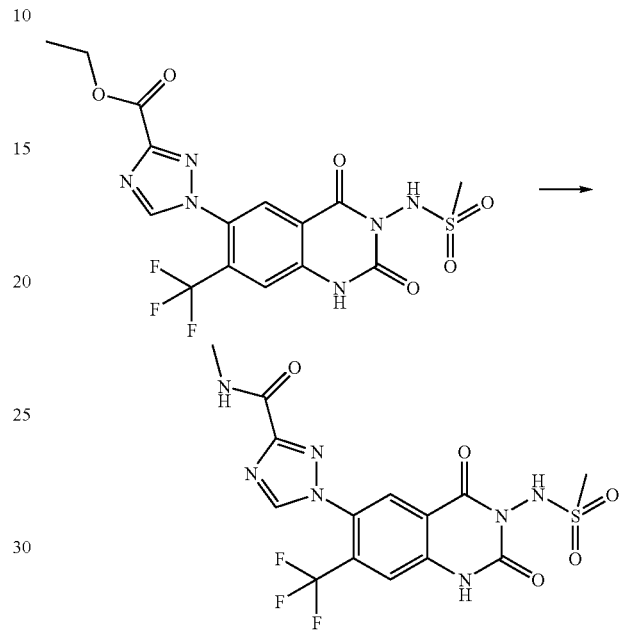

A solution of 150 mg (0.324 mmol) of 1-(3-methanesulfonylamino-2,4-dioxo-7-trifluoromethyl-1,2,3,4-tetrahydroquinazolin-6-yl)-1H-[1,2,4]triazole-3-carboxylic acid ethyl ester in 0.8 ml of methanol is treated with 0.40 ml (3.24 mmol) of a ~8M methylamine solution in ethanol. The mixture is stirred for 22 hours at room temperature and then concentrated in vacuo. The crude product is taken up in water and the pH of the solution is adjusted to 3 with 1 M aqueous HCl solution and the mixture is stirred for 3 hours at 0° C. The crystals are filtered, washed with cold water and dried in vacuo to give 124 mg (86%) of 1-(3-methanesulfonylamino-2,4-dioxo-7-trifluoromethyl-1,2,3,4-tetrahydro-quinazolin-6-yl)-1H-[1,2,4]triazole-3-carboxylic acid methylamide as white crystals, m.p. 257-260° C.

Example 73

N-(6-Imidazol-1-yl-2,4-dioxo-7-trifluoromethyl-1,4-dihydro-2H-quinazolin-3-yl)-methanesulfonamide

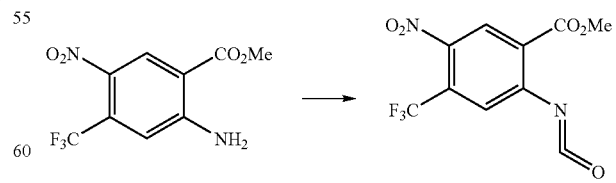

To a suspension of 100 mg (0.379 mmol) of 2-amino-5-nitro-4-trifluoromethyl-benzoic acid methyl ester in 1.5 ml of dry toluene 1.5 ml of a 20% solution of phosgene in toluene are added at −15° C. After warming to room temperature, a stream of phosgene is introduced into the suspension and simultaneously heating is started. At reflux, the stream of phosgene is maintained for one hour, then replaced by a stream of argon for an additional hour. The toluene is distilled off leaving 110 mg (100%) of 2-isocyanato-5-nitro-4-trifluoromethyl-benzoic acid methyl ester as a beige solid. IR (CHCl$_3$): 2260 cm$^{-1}$ (s). $^1$H-NMR (CDCl$_3$, 360 MHz): 4.05 (s, 3H); 7.55 (s, 1H); 8.65 (s, 1H).

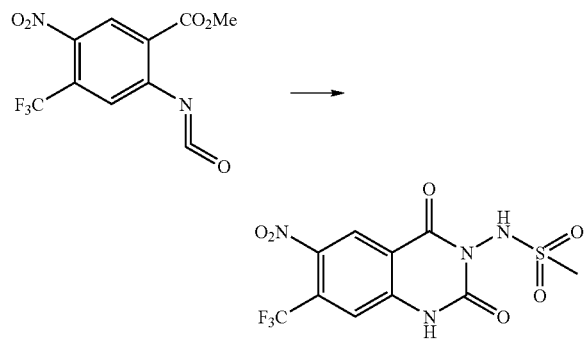

To a solution of 110 mg (0.379 mmol) of 2-isocyanato-5-nitro-4-trifluoromethyl-benzoic acid methyl ester in 1.7 ml of dry tetrahydrofuran 41.7 mg (0.379 mmol) of methanesulfonyl hydrazide in 0.6 ml of dry tetrahydrofuran are added at room temperature. The solution turns into a white suspension that is stirred for one hour, then 0.379 ml of 1 M NaOH solution are added and stirring of the clear solution is continued for 4 hours. After addition of 0.472 ml of 2 M HCl solution and evaporation of the tetrahydrofuran the precipitate is filtered and dried at 50° C./0.1 mm yielding 114 mg (81%) of N-(6-nitro-2,4-dioxo-7-trifluoromethyl-1,4-dihydro-2H-quinazolin-3-yl)-methanesulfonamide as a slightly yellow powder, m.p. 220-232° C. (decomp.). $^1$H-NMR (DMSO-d$_6$, 400 MHz): 3.15 (s, 3H); 7.66 (s, 1H); 8.62 (s, 1H); 10.50 (s, 1H); 12.41 (s, 1H).

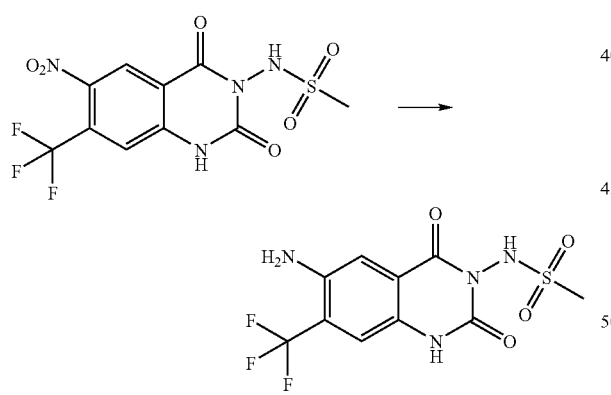

A solution of 109 mg of N-(6-nitro-2,4-dioxo-7-trifluoromethyl-1,4-dihydro-2H-quinazolin-3-yl)-methanesulfonamide in 3 ml of ethanol and 3 ml of acetic acid is hydrogenated in the presence of 30 mg of 10% palladium on carbon. After disappearance of the starting material followed by TLC the reaction mixture is diluted with ethanol and acetic acid and slightly warmed up. The catalyst is filtered off and the filtrate concentrated to dryness. Trituration of the residue with ethyl acetate gives 61 mg (61%) of N-(6-amino-2,4-dioxo-7-trifluoromethyl-1,4-dihydro-2H-quinazolin-3-yl)-methanesulfonamide as a yellow powder, m.p. 240° C. (decomp.). $^1$H-NMR (DMSO-d$_6$, 400 MHz): 3.12 (s, 3H); 5.66 (s, 2H); 7.24 (s, 1H); 7.46 (s, 1H); 10.3 (br s, 1H); 11.4 (br s, 1H).

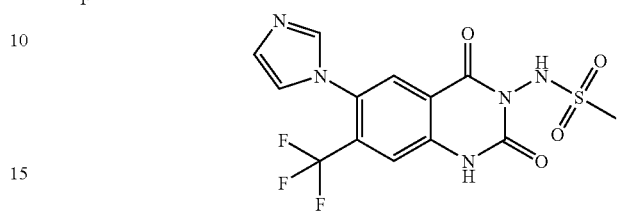

A mixture of 500 mg (1.478 mmol) of N-(6-amino-2,4-dioxo-7-trifluoromethyl-1,4-dihydro-2H-quinazolin-3-yl)-methanesulfonamide, 0.111 ml (1.478 mmol) of formaldehyde solution (37% in water), 0.170 ml (1.478 mmol) of glyoxal solution (40% in water) and 114 mg (1.478 mmol) of ammonium acetate in 3.7 ml of acetic acid is heated for 26 hours in an oil bath of 70° C. After 2 hours, 7 hours and 24 hours half an equivalent (0.739 mmol) of formaldehyde solution, glyoxal solution and ammonium acetate is added. The reaction mixture is concentrated to dryness and the residue fractionated by medium pressure chromatography on a RP-18 column (20 μm particle size) with tetrahydrofuran/water 3:4. After removal of the tetrahydrofuran at the rotavap the fractions are lyophilized, the foams collected and crystallized from ethanol/water 3:1, yielding 217 mg of N-(6-imidazol-1-yl-2,4-dioxo-7-trifluoromethyl-1,4-dihydro-2H-quinazolin-3-yl)-methanesulfonamide as slightly yellow powder, m.p. 285-301° C. (decomp.).

Example 74

N-(2,4-Dioxo-6-thiomorpholin-4-yl-7-trifluoromethyl-1,4-dihydro-2H-quinazolin-3-yl)-methanesulfonamide

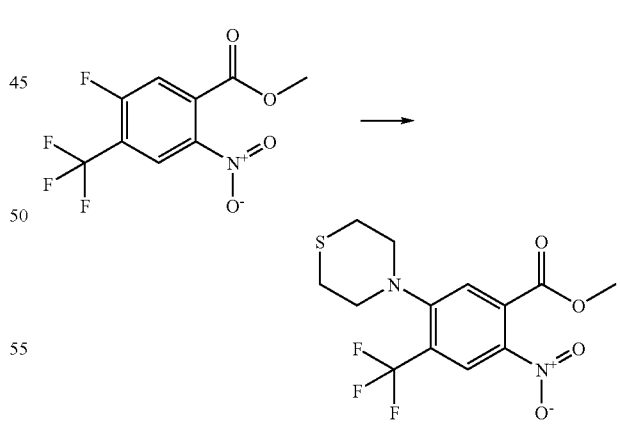

A solution of 240 mg (0.90 mmol) of 5-fluoro-2-nitro-4-trifluoromethyl-benzoic acid methyl ester and 0.189 ml (2.00 mmol) of thiomorpholine in 2.5 ml of tetrahydrofuran is heated at reflux for 2 hours. After evaporation of the tetrahydrofuran the residue is distributed between water and ethyl acetate, the organic phase separated and washed with water and brine, dried over Na$_2$SO$_4$ and concentrated yielding 310 mg of 2-nitro-5-thiomorpholin-4-yl-4-trifluoromethyl-benzoic acid methyl ester as brown powder, m.p. 68-82° C.

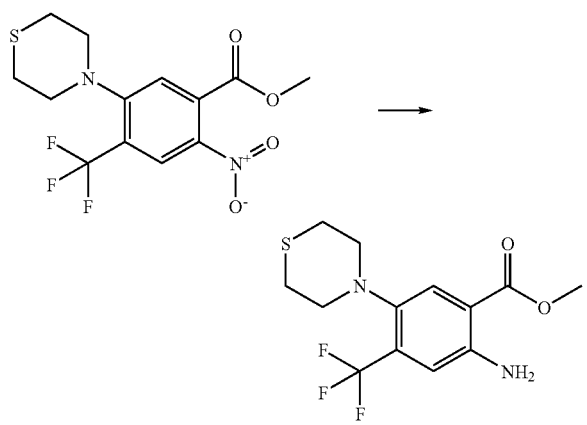

300 mg of 2-nitro-5-thiomorpholin-4-yl-4-trifluoromethyl-benzoic acid methyl ester in 10 ml of dry ethanol are hydrogenated in presence of 60 mg of Raney nickel, After filtration of the catalyst the solution is evaporated to dryness yielding 233 mg of 2-amino-5-thiomorpholin-4-yl-4-trifluoromethyl-benzoic acid methyl ester as yellow powder, m.p. 85-117° C. (decomp.).

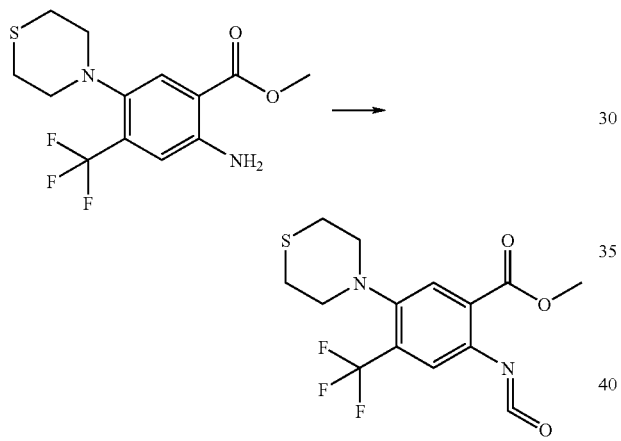

To a suspension of 100 mg (0.312 mmol) of 2-amino-5-thiomorpholin-4-yl-4-trifluoromethyl-benzoic acid methyl ester in 2 ml of dry toluene 1.5 ml of a 20% solution of phosgene in toluene are added at 0° C. After warming to room temperature, a stream of phosgene is introduced into the suspension and simultaneously heating is started. At reflux, the stream of phosgene is maintained for two hours, then replaced by a stream of argon for an additional hour. The toluene is distilled off leaving 126 mg (>100%) of 2-isocyanato-5-thiomorpholin-4-yl-4-trifluoromethyl-benzoic acid methyl ester as a brown solid, sufficiently pure for the next step. $^1$H-NMR (CDCl$_3$, 360 MHz): 2.75-2.80 (m, 2H); 3.15-3.20 (m, 2H); 4.00 (s, 3H); 7.40 (s, 1H); 7.95 (s, 1H).

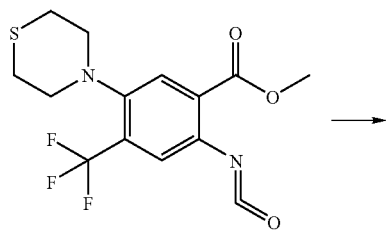

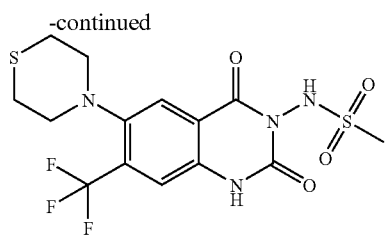

To a solution of 120 mg (0.310 mmol) of 2-isocyanato-5-thiomorpholin-4-yl-4-trifluoromethyl-benzoic acid methyl ester in 1.5 ml of dry tetrahydrofuran 37.5 mg (0.341 mmol) of methanesulfonyl hydrazide in 0.5 ml of dry tetrahydrofuran are added at room temperature. After stirring for 2.5 hours 0.340 ml of 1 M NaOH solution are added and stirring is continued for 1.5 hours, followed by addition of 0.412 ml of 2 M HCl solution. The tetrahydrofuran is evaporated and the aqueous phase is extracted three times with ethyl acetate. The combined organic phases are washed with brine, dried over Na$_2$SO$_4$ and concentrated to dryness. The residue is purified by medium pressure chromatography on silica (20 μm particle size) with ethyl acetate/cyclohexane 2:1, yielding N-(2,4-dioxo-6-thiomorpholin-4-yl-7-trifluoromethyl-1,4-dihydro-2H-quinazolin-3-yl)-methanesulfonamide as a slightly yellow powder, m.p. 245-260° C. (decomp.).

By the same sequence of reactions as in the previous example, starting from 5-fluoro-2-nitro-4-trifluoromethyl-benzoic acid methyl ester and the appropriate amine, the following compounds are prepared:

Example 75

N-(6-[1,4]Oxazepan-4-yl-2,4-dioxo-7-trifluoromethyl-1,4-dihydro-2H-quinazolin-3-yl)-methanesulfonamide Slightly yellow powder, m.p. 198-203° C.

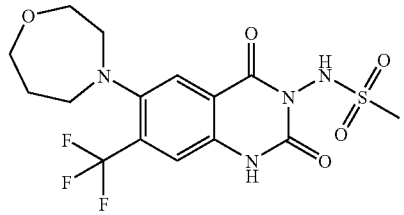

Example 76

N-[6-(4,4-Difluoro-piperidin-1-yl)-2,4-dioxo-7-trifluoromethyl-1,4-dihydro-2H-quinazolin-3-yl]-methanesulfonamide Yellow powder, m.p. 249-261° C. (decomp.)

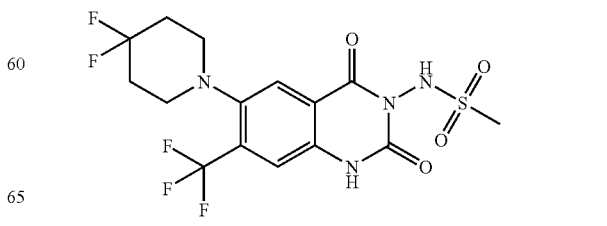

Example 77

N-[6-(1,4-Dioxa-8-aza-spiro[4.5]dec-8-yl)-2,4-dioxo-7-trifluoromethyl-1,4-dihydro-2H-quinazolin-3-yl]-methanesulfonamide Yellow powder, m.p. 253-262° C.

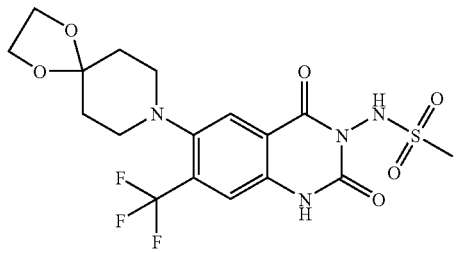

Example 78

N-[2,4-Dioxo-6-(4-oxo-piperidin-1-yl)-7-trifluoromethyl-1,4-dihydro-2H-quinazolin-3-yl]-methanesulfonamide

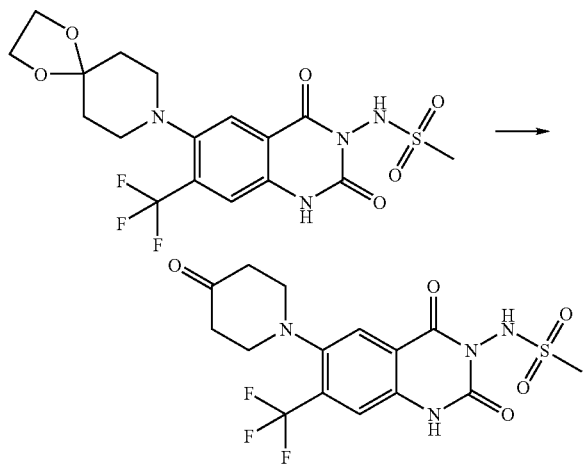

500 mg of N-[6-(1,4-dioxa-8-aza-spiro[4.5]dec-8-yl)-2,4-dioxo-7-trifluoromethyl-1,4-dihydro-2H-quinazolin-3-yl]-methanesulfonamide are treated with 3.4 ml of 6 M HCl solution in 15 ml of dioxane for 26 hours at room temperature. After dilution with water the aqueous phase is extracted with ethyl acetate, the organic phase separated, washed with brine, dried over Na$_2$SO$_4$ and concentrated to dryness leaving 490 mg of a yellow powder. From this powder 280 mg are fractionated by medium pressure chromatography on a RP-18 column (20 μm particle size) with acetonitril/water 1:2. The fractions containing the product are combined and extracted with ethyl acetate, the organic phase dried over Na$_2$SO$_4$ and concentrated yielding 180 mg of N-[2,4-dioxo-6-(4-oxo-piperidin-1-yl)-7-trifluoromethyl-1,4-dihydro-2H-quinazolin-3-yl]-methanesulfonamide as a slightly yellow powder, m.p. 238-242° C.

Example 79

N-(6-Azetidin-1-yl-2,4-dioxo-7-trifluoromethyl-1,4-dihydro-2H-quinazolin-3-yl)-methanesulfonamide

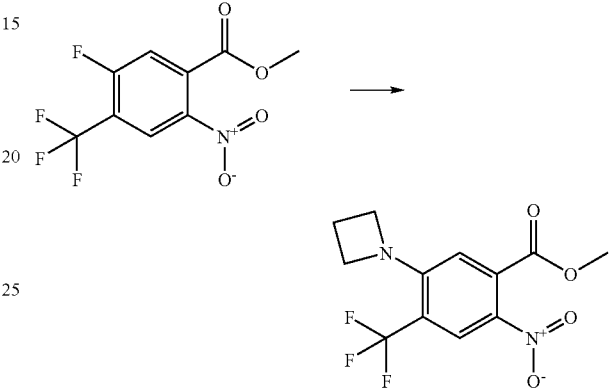

A solution of 1.07 g (4.0 mmol) of 5-fluoro-2-nitro-4-trifluoromethyl-benzoic acid methyl ester and 0.461 ml (6.8 mmol) of azetidine in 10 ml of tetrahydrofuran is heated at reflux for 90 minutes. After evaporation of the tetrahydrofuran the residue is distributed between water and ethyl acetate, the organic phase separated and washed with water and brine, dried over Na$_2$SO$_4$ and concentrated yielding 1.19 g of 5-azetidin-1-yl-2-nitro-4-trifluoromethyl-benzoic acid methyl ester as yellow powder, m.p. 127-136° C.

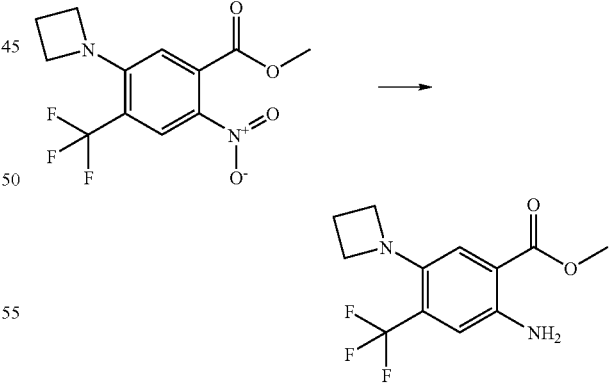

1.10 g of 5-azetidin-1-yl-2-nitro-4-trifluoromethyl-benzoic acid methyl ester in 12 ml of tetrahydrofuran are hydrogenated in presence of 200 mg of palladium on carbon. After filtration of the catalyst the solution is evaporated to dryness yielding 0.99 g of 2-amino-5-azetidin-1-yl-4-trifluoromethyl-benzoic acid methyl ester as yellow powder, m.p. 80-86° C.

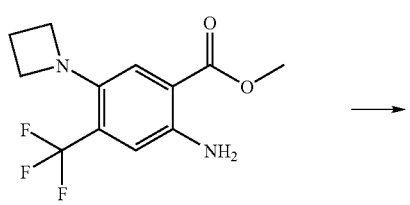

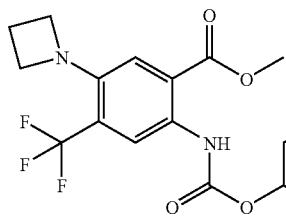

A mixture of 129 mg (0.470 mmol) of 2-amino-5-azetidin-1-yl-4-trifluoromethyl-benzoic acid methyl ester, 0.082 ml (0.470 mmol) of ethyl-diisopropyl-amine, 0.066 ml (0.470 mmol) of 4-chloroformylchloroformate and 4 ml of dioxane is stirred for 45 minutes and subsequently concentrated to dryness. The residue is distributed between water and ethyl acetate, the organic phase separated and washed with water and brine, dried over Na$_2$SO$_4$ and concentrated to leave a viscous mass which is submitted to medium pressure chromatography on silica with ethyl acetate/cyclohexane 1:4. From the first fraction, after evaporation, 123 mg of 5-azetidin-1-yl-2-(4-chloro-phenoxycarbonylamino)-4-trifluoromethyl-benzoic acid methyl ester are obtained as yellow foam. $^1$H-NMR (DMSO-d$_6$+D$_2$O): 7.20 d, J=10 Hz, 2H; 7.20 s, 1H; 7.15 s, 1H; 6.75 d, J=10 Hz, 2H; 3.85 s, 3H; 3.75 t, J=7 Hz, 4H; 2.15 pent, J=7 Hz, 2H.

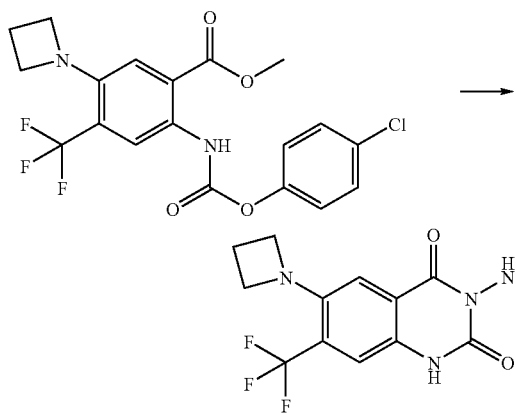

A solution of 115 mg (0.268 mmol) of 5-azetidin-1-yl-2-(4-chloro-phenoxycarbonylamino)-4-trifluoromethyl-benzoic acid methyl ester, 30 mg (0.268 mmol) of methanesulfonyl hydrazide, 0.070 ml (0.402 mmol) of ethy-Idiisopropyl-amine and 3 ml of dioxane is stirred for 24 hours at 70° C. After evaporation to dryness the residue is fractionated by medium pressure chromatography on a RP-18 column (20 µm particle size) with acetonitril/water 3:4. The fractions containing the product are combined and extracted with ethyl acetate, the organic phase dried over Na$_2$SO$_4$ and concentrated leaving an amorphous powder which is crystallized from acetonitril/water to give 47 mg of N-(6-azetidin-1-yl-2,4-dioxo-7-trifluoromethyl-1,4-dihydro-2H-quinazolin-3-yl)-methanesulfonamide as a yellow powder, m.p. 266-283° C.

Example 80

N-[2,4-Dioxo-6-(pyridin-3-yloxy)-7-trifluoromethyl-1,4-dihydro-2H-quinazolin-3-yl]-methanesulfonamide

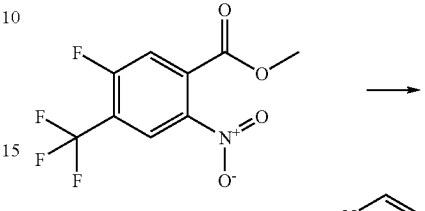

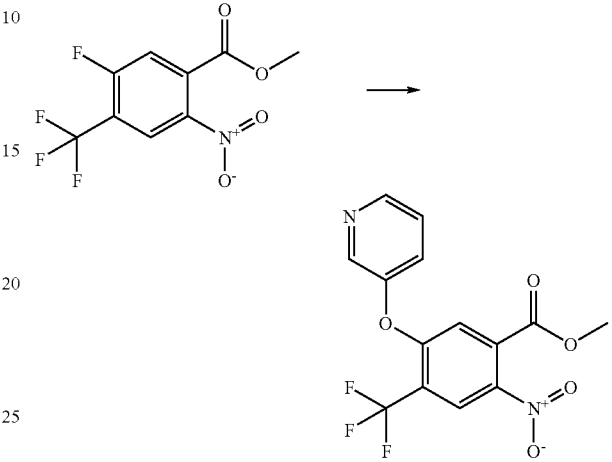

To a suspension of 198 mg (4.53 mmol) of sodium hydride (65% in oil, washed with pentane) in 2.5 ml of dry tetrahydrofuran a solution of 356 mg (3.74 mmol) of 3-hydroxypyridine in 5 ml of tetrahydrofuran is dropped and the mixture stirred for 1 hour at room temperature. After cooling to 0° C. 1.0 g (3.74 mmol) of 5-fluoro-2-nitro-4-trifluoromethyl-benzoic acid methyl ester dissolved in 10 ml of tetrahydrofuran is added and stirring continued for 7 hours. The reaction mixture is diluted with water and extracted with ethyl acetate. The organic phase is washed with brine, dried over Na$_2$SO$_4$ and evaporated to give an oil which is fractionated by medium pressure chromatography on silica with ethyl acetate/cyclohexane 1:1. The fractions containing the product are combined and evaporated yielding 977 mg of 2-nitro-5-(pyridin-3-yloxy)-4-trifluoromethyl-benzoic acid methyl ester as white powder, m.p. 98-100° C.

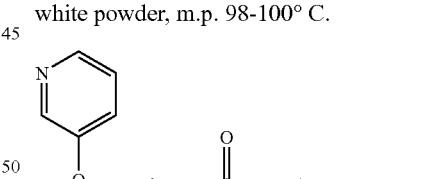

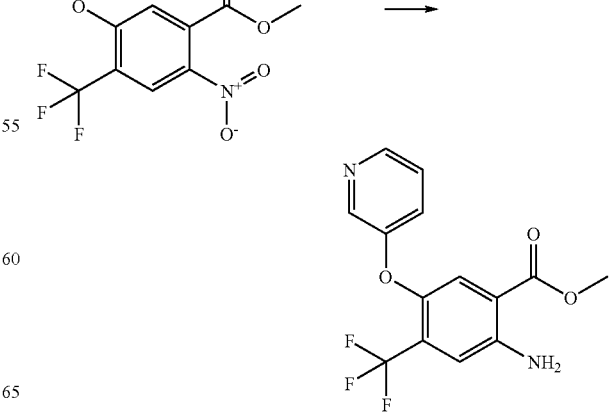

919 mg of 2-nitro-5-(pyridin-3-yloxy)-4-trifluoromethyl-benzoic acid methyl ester in 20 ml of tetrahydrofuran are hydrogenated in presence of 227 mg of palladium on carbon. After filtration of the catalyst the solution is evaporated to dryness and the residue purified by medium pressure chromatography on silica with ethyl acetate/cyclohexane 1:2 yielding 611 mg of 2-amino-5-(pyridin-3-yloxy)-4-trifluoromethyl-benzoic acid methyl ester as yellow powder, m.p. 132-134° C.

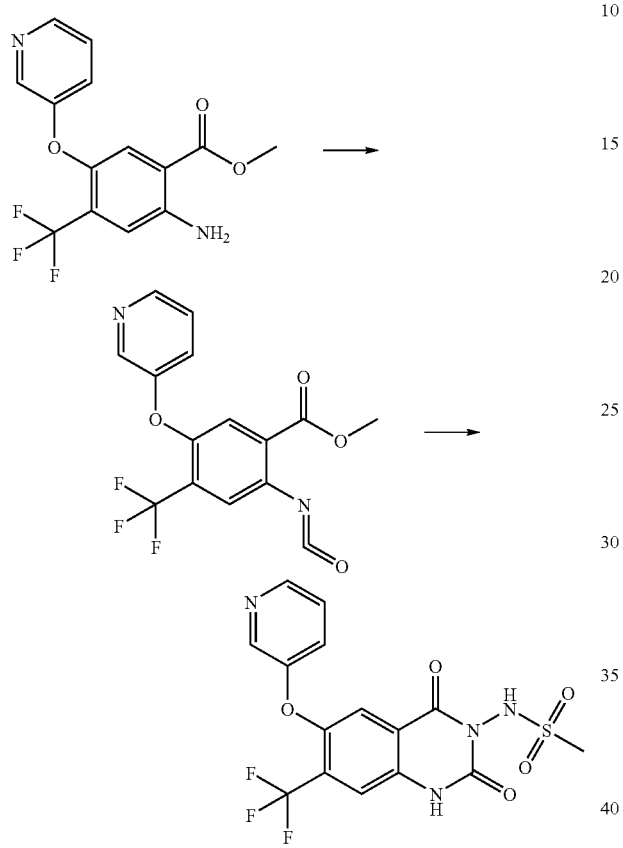

300 mg of 2-amino-5-(pyridin-3-yloxy)-4-trifluoromethyl-benzoic acid methyl ester are treated with phosgene according to the procedure described in example 74, yielding 291 mg of 2-isocyanato-5-(pyridin-3-yloxy)-4-trifluoromethyl-benzoic acid methyl ester as a brownish oil. $^1$H-NMR (CDCl$_3$): 8.50 br s, 1H; 8.40 s, 1H; 7.60 s, 1H; 7.50 s, 3H; 3.95 s, 3H.

288 mg of this oil are cyclized with methanesulfonyl hydrazide according to the procedure described in example 74, yielding 211 mg of N-[2,4-dioxo-6-(pyridin-3-yloxy)-7-trifluoromethyl-1,4-dihydro-2H-quinazolin-3-yl]-methanesulfonamide as white powder, m.p. 194-196° C. (acetonitril).

Example 81

N-(6-Dimethylamino-2,4-dioxo-7-trifluoromethyl-1,4-dihydro-2H-quinazolin-3-yl)-methanesulfonamide

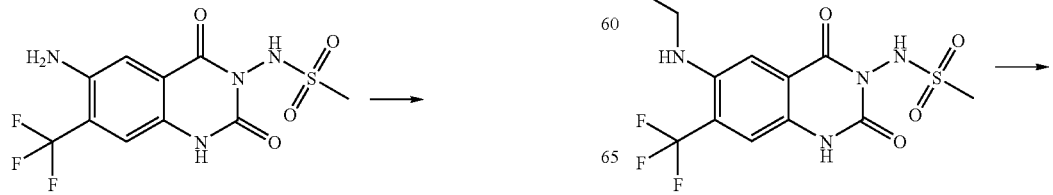

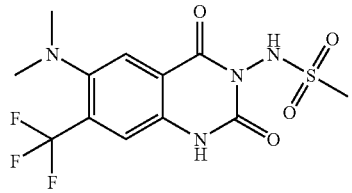

A mixture of 370 mg (1.094 mmol) of N-(6-amino-2,4-dioxo-7-trifluoromethyl-1,4-dihydro-2H-quinazolin-3-yl)-methanesulfonamide, 0.083 ml (1.02 mmol) of formaldehyde solution (37% in water), 0.0033 ml of acetic acid, 21 ml of tetrahydrofuran and 21 ml of water is hydrogenated in presence of 100 mg of palladium on carbon for 10 days. After day 1, 3, 4, 5 and 6 another portion of formaldehyde (0.083 ml) and acetic acid (0.0033 ml) is added. After filtration of the reaction mixture the tetrahydrofuran is evaporated and the remaining aqueous phase extracted with ethyl acetate. The organic phase is washed with brine, dried over Na$_2$SO$_4$ and concentrated to dryness leaving a yellow powder that is fractionated by medium pressure chromatography on a RP-18 column (20 μm particle size) with acetonitril/water 3:4. The fractions containing the product are combined and extracted with ethyl acetate, the organic phase dried over Na$_2$SO$_4$ and concentrated yielding 277 mg of N-(6-dimethylamino-2,4-dioxo-7-trifluoromethyl-1,4-dihydro-2H-quinazolin-3-yl)-methanesulfonamide as yellow powder, m.p. 254-272° C.

In an analogous manner to the previous example the following compound is prepared:

Example 82

N-[6-(2-Hydroxy-ethylamino)-2,4-dioxo-7-trifluoromethyl-1,4-dihydro-2H-quinazolin-3-yl]-methanesulfonamide Yellow powder, m.p. 240-246° C.

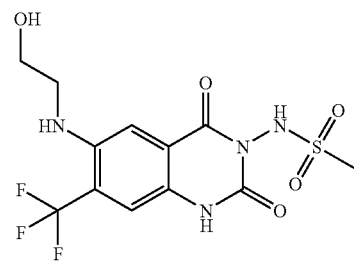

Example 83

N-{6-[(2-Hydroxy-ethyl)-methyl-amino]-2,4-dioxo-7-trifluoromethyl-1,4-dihydro-2H-quinazolin-3-yl}-methanesulfonamide

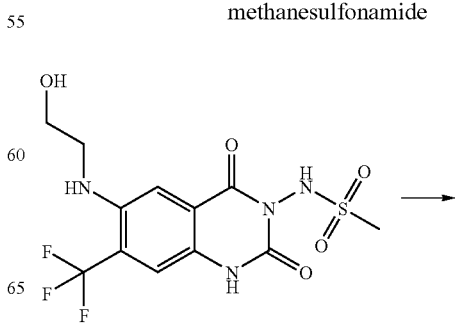

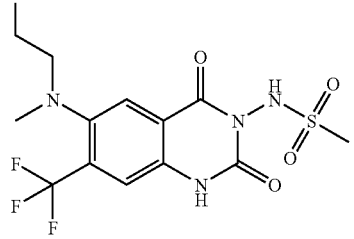

A mixture of 370 mg (0.968 mmol) of N-[6-(2-hydroxy-ethylamino)-2,4-dioxo-7-trifluoromethyl-1,4-dihydro-2H-quinazolin-3-yl]-methanesulfonamide, 0.074 ml (0.912 mmol) of formaldehyde solution (37% in water), 4 ml of acetic acid, 15 ml of tetrahydrofuran and 15 ml of water is hydrogenated in presence of 115 mg of palladium on carbon for 3 days. After day 1 and 2 another portion of formaldehyde (0.074 ml) is added. After filtration of the reaction mixture the tetrahydrofuran is evaporated and the remaining aqueous phase extracted with ethyl acetate. The organic phase is washed with brine, dried over $Na_2SO_4$ and concentrated to dryness leaving a brown oil that is fractionated by medium pressure chromatography on a RP-18 column (20 μm particle size) with acetonitril/water 1:2. The fractions containing the product are combined and extracted with ethyl acetate, the organic phase dried over $Na_2SO_4$ and concentrated yielding 165 mg of N-{6-[(2-hydroxy-ethyl)-methyl-amino]-2,4-dioxo-7-trifluoromethyl-1,4-dihydro-2H-quinazolin-3-yl}-methanesulfonamide as yellow powder, m.p. 220-224° C.

Example 84

N-{6-[4-(4-Methoxy-phenyl)-imidazol-1-yl]-2,4-dioxo-7-trifluoromethyl-1,4-dihydro-2H-quinazolin-3-yl}-methanesulfonamide

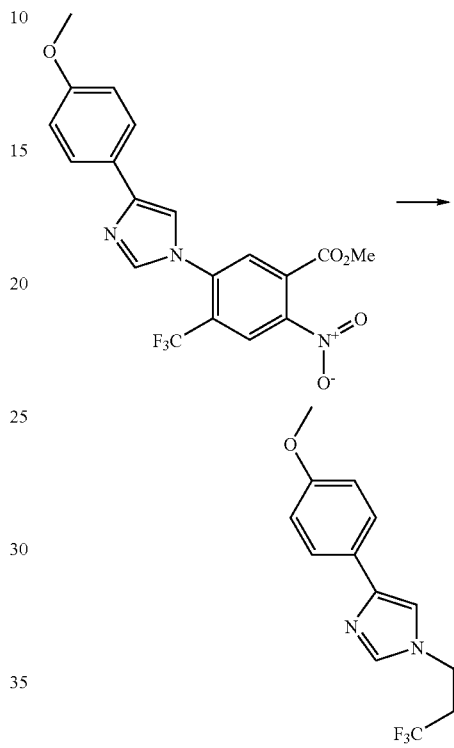

A mixture of 1.200 g (4.49 mmol) of 5-fluoro-2-nitro-4-trifluoromethyl-benzoic acid methyl ester and 0.861 g (4.94 mmol) of 4-(4-methoxy-phenyl)-1H-imidazole in 15 ml of tetrahydrofuran are refluxed for 5 hours. After cooling, the reaction mixture is distributed between ethyl acetate and water, the organic phase separated and washed with brine, dried over $Na_2SO_4$ and concentrated to dryness. The residue is purified by flash chromatography on silica (20 μm particle size) with ethyl acetate/hexane 2:3, yielding 1.511 g of 5-[4-(4-methoxy-phenyl)-imidazol-1-yl]-2-nitro-4-trifluoromethyl-benzoic acid methyl ester as a yellow powder. $^1$H-NMR (DMSO-$d_6$, 400 MHz): 3.80 s, 3H; 3.95 s, 3H; 7.00 d, J=10.4 Hz, 2H; 7.78 d, J=10.4 Hz, 2H; 7.95 s, 1H; 8.00 s, 1H; 8.28 s, 1H; 8.72 s, 1H.

1.470 g of 5-[4-(4-methoxy-phenyl)-imidazol-1-yl]-2-nitro-4-trifluoromethyl-benzoic acid methyl ester in 25 ml of tetrahydrofuran are hydrogenated in presence of 200 mg of palladium on carbon. After filtration of the catalyst the solution is evaporated to dryness and the residue purified by flash chromatography on silica (40-63 μm particle size) with dichloromethane/methanol 98:2, yielding 1.270 g of 2-amino-5-[4-(4-methoxy-phenyl)-imidazol-1-yl]-4-trifluoromethyl-benzoic acid methyl ester as a beige solid. $^1$H-NMR (DMSO-$d_6$, 400 MHz): 3.80 s, 3H; 3.95 s, 3H; 6.95 d, J=10.4 Hz, 2H; 7.30 s, 2H; 7.40 s, 1H; 7.70 s, 1H; 7.75 s, 1H; 7.78 d, J=10.4 Hz, 2H; 7.80 s, 1H.

-continued

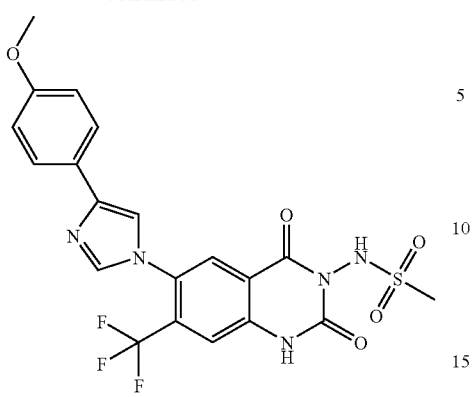

A mixture of 0.923 g (2.31 mmol) of 2-amino-5-[4-(4-methoxy-phenyl)-imidazol-1-yl]-4-trifluoromethyl-benzoic acid methyl ester and 0.976 ml (6.93 mmol) of triethylamine is treated with 1.04 g (3.47 mmol) of triphosgene and stirred at room temperature for 90 min. A solution of 0.520 g (4.62 mmol) of methanesulfonyl hydrazide in 20 ml of dioxane is added and stirring continued at 80° C. After 2 and 3 hours two additional portions of 400 mg and 200 mg, respectively, of methanesulfonyl hydrazide in dioxane are added. After 4 hours the reaction mixture is concentrated, diluted with a mixture of 80 ml of dioxane/water 1:1 and treated with 4.5 ml of 1 M NaOH solution at room temperature for 1 hour. The pH of the reaction mixture is adjusted to 5.5 with acetic acid, the mixture concentrated and the residue taken up into ethyl acetate. The organic phase is washed with water and brine, dried over Na₂SO₄ and evaporated to dryness. The residue is purified by flash chromatography on silica (40-63 μm particle size) with dichloromethane/methanol 95:5, and the obtained product recrystallized from methanol/dichloromethane and from methanol/dichloromethane/diisopropyl ether, yielding 0.725 g of N-{6-[4-(4-methoxy-phenyl)-imidazol-1-yl]-2,4-dioxo-7-trifluoromethyl-1,4-dihydro-2H-quinazolin-3-yl}-methanesulfonamide as a white powder, m.p.=293-294° C.

Example 85

N-{6-[4-(4-Methoxymethyl-phenyl)-imidazol-1-yl]-2,4-dioxo-7-trifluoromethyl-1,4-dihydro-2H-quinazolin-3-yl}-methanesulfonamide

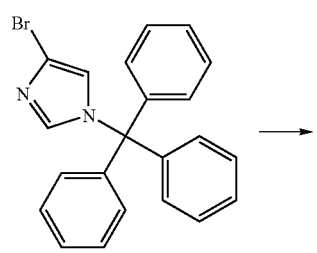

-continued

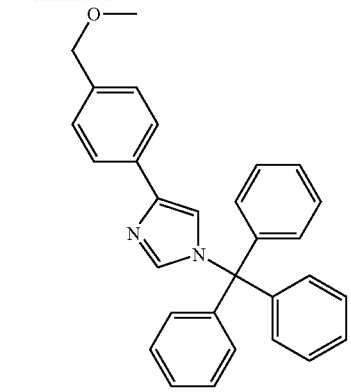

To a suspension of 3.00 g (7.71 mmol) of 4-bromo-1-trityl-1H-imidazole in 30 ml of dioxane 1.58 g (9.23 mmol) of 4-methoxymethyl boronic acid, 3.47 g (10.5 mmol) of cesium carbonate and 0.121 g (0.131 mmol) of tris-(dibenzylidene-aceton)dipalladium are added, followed by 0.315 ml (0.308 ml) of a solution of 5 g of tri-t-buylphosphine in 25 ml of dioxane. The mixture is heated at 80° C. and stirred for 6.5 hours. After cooling to room temperature the suspension is diluted with dichloromethane and filtered, the filter cake washed with ethyl acetate and the filtrate concentrated to dryness. The residue is purified by flash chromatography on silica (40-63 μm particle size) with hexane/ethyl acetate 7:3, yielding 2.805 g of 4-(4-methoxymethyl-phenyl)-1-trityl-1H-imidazole, Rt=4.659 min by HPLC on a nucleosil C18HD column with acetonitril+0.05% TFA/water+0.05% TFA, 20/80 to 100/0 over 6 min, 1.0 ml/min solvent flow. MS (API-ES, pos. scan): e/m=431 (M+1).

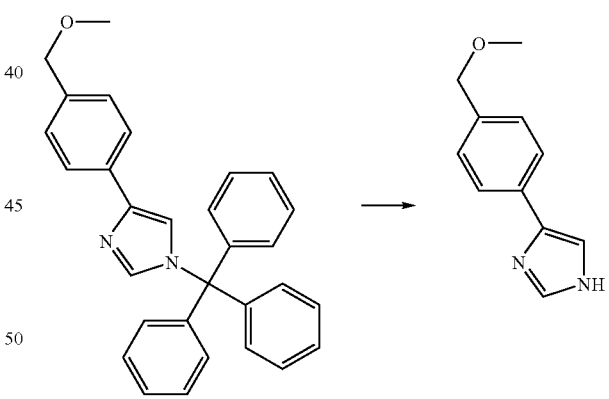

A mixture of 2.800 g of 4-(4-methoxymethyl-phenyl)-1-trityl-1H-imidazole in 50 ml of TFA is stirred at room temperature for 3 hours. The reaction mixture is concentrated, taken up into ethyl acetate and the organic phase washed with sat. NaHCO₃-solution and brine and dried over Na₂SO₄. Evaporation of the solvent gives a residue which is purified by flash chromatography on silica (40-63 μm particle size) with dichloromethane/methanol 93:7, yielding 1.169 g of 4-(4-methoxymethyl-phenyl)-1H-imidazole as a beige powder. Rt=2.906 min by HPLC on a nucleosil C18HD column with acetonitril+0.05% TFA/water+0.05% TFA, 20/80 to 100/0 over 6 min, 1.0 ml/min solvent flow. MS (API-ES, pos. scan): e/m=189 (M+1).

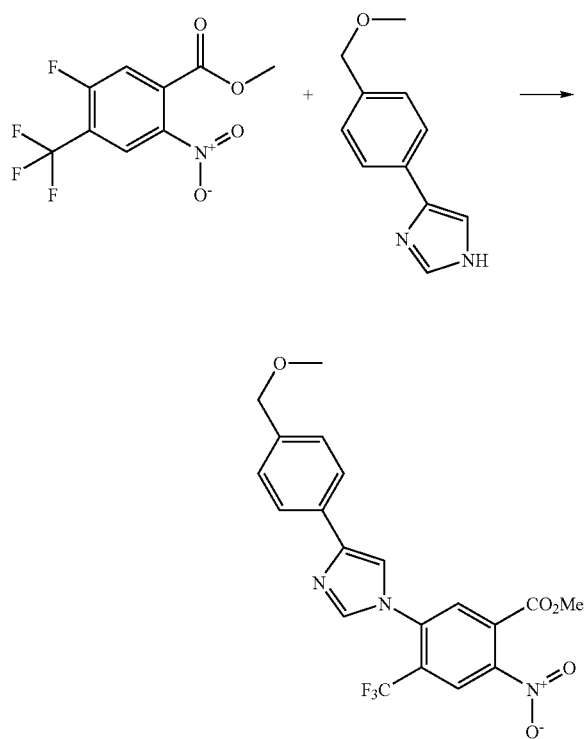

A mixture of 1.00 g (3.74 mmol) of 5-fluoro-2-nitro-4-trifluoromethyl-benzoic acid methyl ester and 0.775 g (4.12 mmol) of 4-(4-methoxymethyl-phenyl)-1H-imidazole in 10 ml of tetrahydrofuran are refluxed for 2 hours. After cooling, the reaction mixture is distributed between ethyl acetate and water, the organic phase separated and washed with brine, dried over Na$_2$SO$_4$ and concentrated to dryness. The residue is purified by flash chromatography on silica (40-63 μm particle size) with ethyl acetate/hexane 2:3, yielding 1.55 g of 5-[4-(4-methoxymethyl-phenyl)-imidazol-1-yl]-2-nitro-4-trifluoromethyl-benzoic acid methyl ester acid as a yellow powder, m.p.=135-137° C. $^1$H-NMR (DMSO-d$_6$, 400 MHz): 3.30 s, 3H; 3.95 s, 3H; 4.42 s, 3H; 7.35 d, J 10.4 Hz, 2H; 7.82 d, J=10.4 Hz, 2H; 8.02 s, 1H; 8.05 s, 1H; 8.30 s, 1H; 8.72 s, 1H.

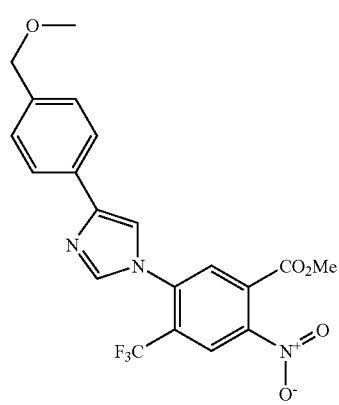

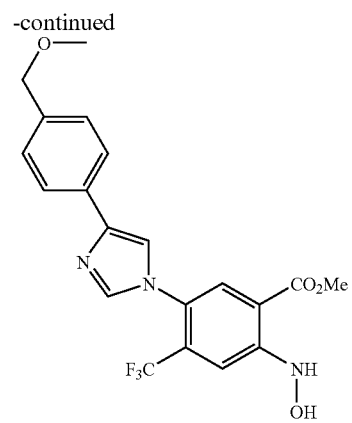

1.00 g of 5-[4-(4-methoxymethyl-phenyl)-imidazol-1-yl]-2-nitro-4-trifluoromethyl-benzoic acid methyl ester in 20 ml of tetrahydrofuran is hydrogenated in presence of 200 mg of platinum on carbon. After filtration of the catalyst the solution is evaporated to dryness yielding 0.661 g of 2-hydroxyamino-5-[4-(4-methoxymethyl-phenyl)-imidazol-1-yl]-4-trifluoromethyl-benzoic acid methyl ester as a yellow solid. $^1$H-NMR (DMSO-d$_6$, 400 MHz): 3.30 s, 3H; 3.82 s, 3H; 4.40 s, 2H; 7.35 d, J=10.4 Hz, 2H; 7.62 s, 1H; 7.80 d, J=10.4 Hz, 2H; 7.85-7.90 m, 3H.

MS (API-ES, pos. scan): e/m=422 (M+1).

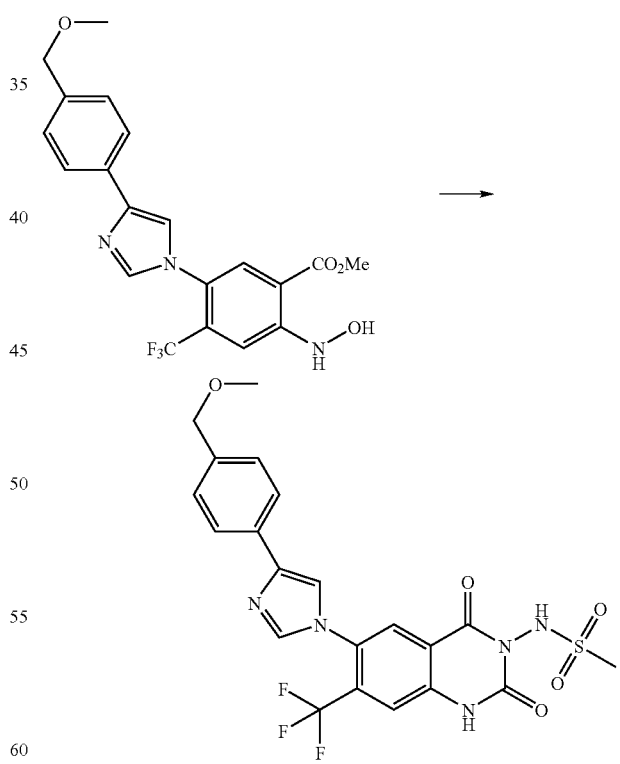

A mixture of 0.519 g (1.23 mmol) of 2-hydroxyamino-5-[4-(4-methoxymethyl-phenyl)-imidazol-1-yl]-4-trifluoromethyl-benzoic acid methyl ester and 0.530 ml (3.76 mmol) of triethylamine is treated with 0.564 g (1.88 mmol) of triphosgene and stirred at room temperature for 105 min. A solution of 0.282 g (2.51 mmol) of methanesulfonyl hydrazide in 20 ml of dioxane is added and stirring continued at 80° C. for 1 hour. The reaction mixture is cooled to room temperature, diluted with 25 ml of water and treated with 2.5 ml of 1M NaOH solution for 30 min. After acidification with 1 M acetic acid to pH 5.5, the mixture is concentrated, the residue taken up into ethyl acetate and the organic phase washed with water and brine, dried over $Na_2SO_4$. and concentrated to dryness. The residue is purified by flash chromatography on silica (40-63 μm particle size) with dichloromethane/methanol 95:5 yielding 0.196 g of N-{6-[4-(4-methoxymethyl-phenyl)-imidazol-1-yl]-2,4-dioxo-7-trifluoromethyl-1,4-dihydro-2H-quinazolin-3-yl}-methanesulfonamide as beige powder, m.p. 252-257° C.

Example 86

N-[2,4-Dioxo-6-(2-oxo-2H-pyridin-1-yl)-7-trifluoromethyl-1,4-dihydro-2H-quinazolin-3-yl]-methanesulfonamide HPLC analyses are performed using a system comprising Gilson 331 pumps coupled to a Gilson UV/VIS 152 detector and a Finnigan AQA spectrometer (ESI), a 50 μL loop injection valve and a Waters XTerra MS C18 3.5 μm 4.6×50 mm column running a gradient from 5% to 90% acetonitrile containing 0.05% TFA. Retention times ($R_t$) are recorded for all new compounds.

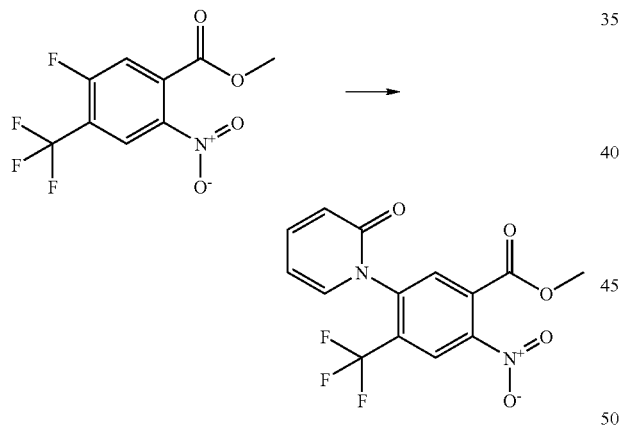

To a suspension of NaH (315 mg, 1.4 eq) in 50 ml of tetrahydrofuran, a solution of 2-hydroxypyridine (801 mg, 1.5 eq) in 5 ml of tetrahydrofuran is added drop-wise. The mixture is stirred at room temperature for 30 min before addition of 5-fluoro-2-nitro-4-trifluoromethyl-benzoic acid methyl ester (1.5 g, 5.61 mmol) in 10 ml of tetrahydrofuran. The resulting mixture is stirred at room temperature for 16 hours. The solvent is removed in vacuo and the crude oil is solubilised in ethyl acetate. The organic phase is washed with sat $NaHCO_3$ solution, dried over sodium sulfate and concentrated in vacuo to afford a crude yellow oil. The crude product is purified by flash-chromatography (ethyl acetate/hexane (0:100 to 100:0)) to obtain 2-nitro-5-(2-oxo-2H-pyridin-1-yl)-4-trifluoromethyl-benzoic acid methyl ester as a yellow solid (1.3 g, 68% yield) (ES-MS: m/z 328 [M+H+$CH_3CN$]$^+$, $R_t$ 4.67 min.).

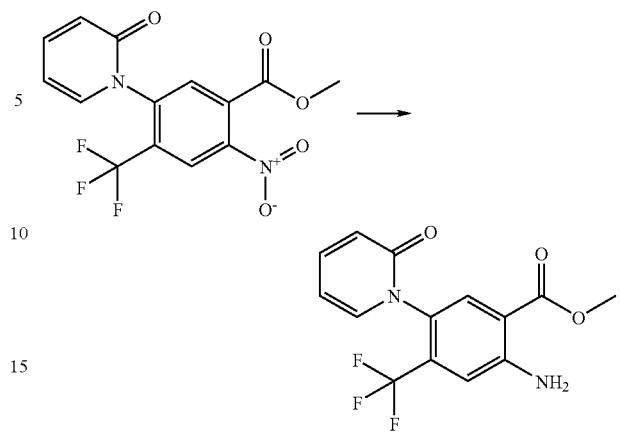

2-Nitro-5-(2-oxo-2H-pyridin-1-yl)-4-trifluoromethyl-benzoic acid methyl ester (1.3 g, 3.8 mmol) is hydrogenated over Raney Nickel (400 mg) under 3 bar of $H_2$ for 6 hours. The mixture is then filtered through a pad of celite and washed with methanol and dioxane. The solvent is removed in vacuo to afford after high-vacuum drying 2-amino-5-(2-oxo-2H-pyridin-1-yl)-4-trifluoromethyl-benzoic acid methyl ester as a white solid (1.2 g, 100%) (ES-MS: m/z 313 [M+H]$^+$, $R_t$ 4.45 min.).

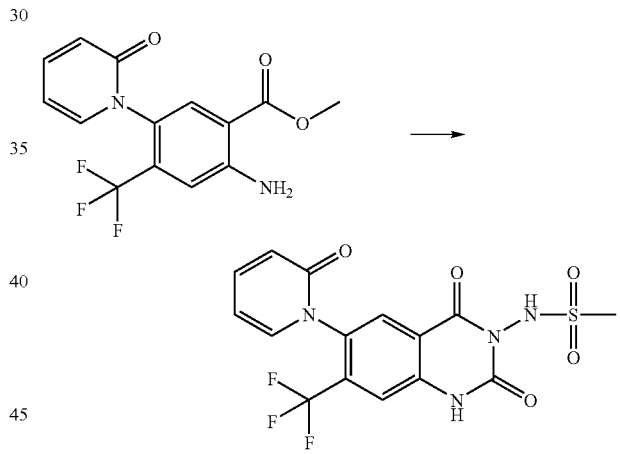

To a solution of 2-amino-5-(2-oxo-2H-pyridin-1-yl)-4-trifluoromethyl-benzoic acid methyl ester (500 mg, 1.6 mmol) in 20 ml of dioxane, 4-chlorophenyl chloroformate (0.273 ml, 1.25 eq) is added. The resulting mixture is stirred at 100° C. for 1 hour. The solvent is then removed in vacuo. The crude oil is dissolved in 20 ml of dioxane and ethyl-diisopropyl-amine (0.550 ml, 2 eq) and methanesulphonyl hydrazide (177 mg, 1 eq) are added. The resulting mixture is stirred at 100° C. for 2 hours. Solvent is removed in vacuo to dryness and the resulting crude is solubilised into 10 ml of dichloromethane and the solution is left at room temperature for 24 hours. The resulting precipitate is filtered off, washed with dichloromethane and high-vacuum dried to afford N-[2,4-dioxo-6-(2-oxo-2H-pyridin-1 -yl)-7-trifluoromethyl-1,4-dihydro-2H-quinazolin-3-yl]-methanesulfonamide as a white solid (100 mg, 15% yield) (ES-MS: m/z 458.3 [M+H+$CH_3CN$]$^{+, R}$, $t_r$ 3.73 min.). $^1$H-NMR (DMSO-$d_6$, 400 MHz) 8.02 (s, 1H), 7.66(s, 1H), 7.49-7.50 (m, 2H), 6.46 (d, 1H, J=7.8 Hz), 6.31 (t, 1H, J=7.8 Hz), 3.15 (s, 3H).

Example 87

N-(3-Methanesulfonylamino-2,4-dioxo-7-trifluoromethyl-1,2,3,4-tetrahydro-quinazolin-6-yl)-N-methyl-acetamide HPLC analyses are performed using a system comprising Gilson 331 pumps coupled to a Gilson UV/VIS 152 detector and a Finnigan AQA spectrometer (ESI), a 50 μL loop injection valve and a Waters XTerra MS C18 3.5 μm 4.6×50 mm column running a gradient from 5% to 90% acetonitrile containing 0.05% TFA. Retention times ($R_t$) are recorded for all new compounds.

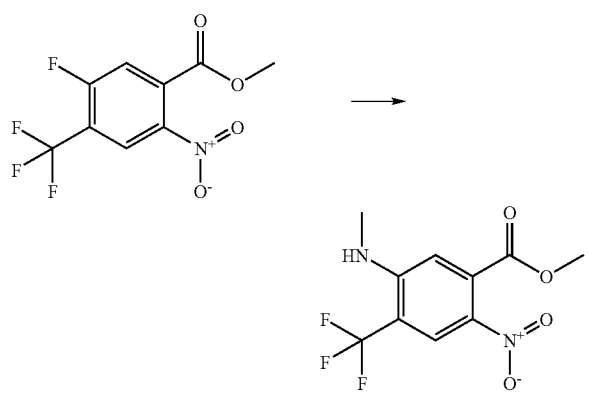

5-Fluoro-2-nitro-4-trifluoromethyl-benzoic acid methyl ester (300 mg, 1.12 mmoles) is dissolved in dioxane and after addition of methylamine (0.490 ml, 3.5 eq.) the yellow mixture is stirred at room temperature for 2 days. The mixture is evaporated to dryness. Dichloromethane is added and the suspension is filtrated. Evaporation of the filtrate yielded 2-nitro-5-methylamino-4-trifluoromethyl-benzoic acid methyl ester as a yellow solid (291.3 mg, 95.4% yield). The product is used in the next step without further purification.

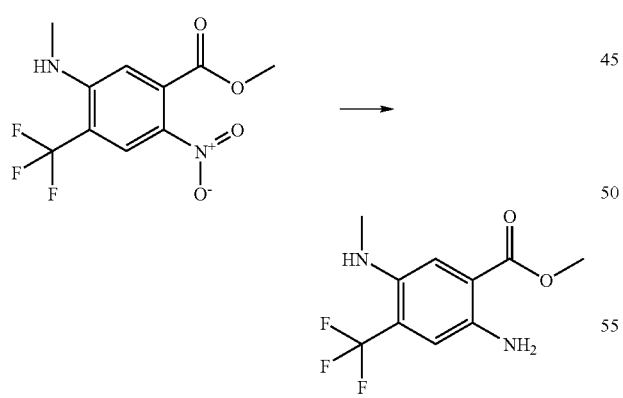

2-Nitro-5-methylamino-4-trifluoromethyl-benzoic acid methyl ester is dissolved in methanol/tetrahydrofuran and after addition of 10% Pd-C, the mixture is stirred for 45 min. at room temperature under hydrogen. The mixture is filtrated over celite and evaporated under reduced pressure to give 2-amino-5-methylamino-4-trifluoromethyl-benzoic acid methyl ester as an orange oil (240 mg, 103% yield). The product is used in the next step without further purification.

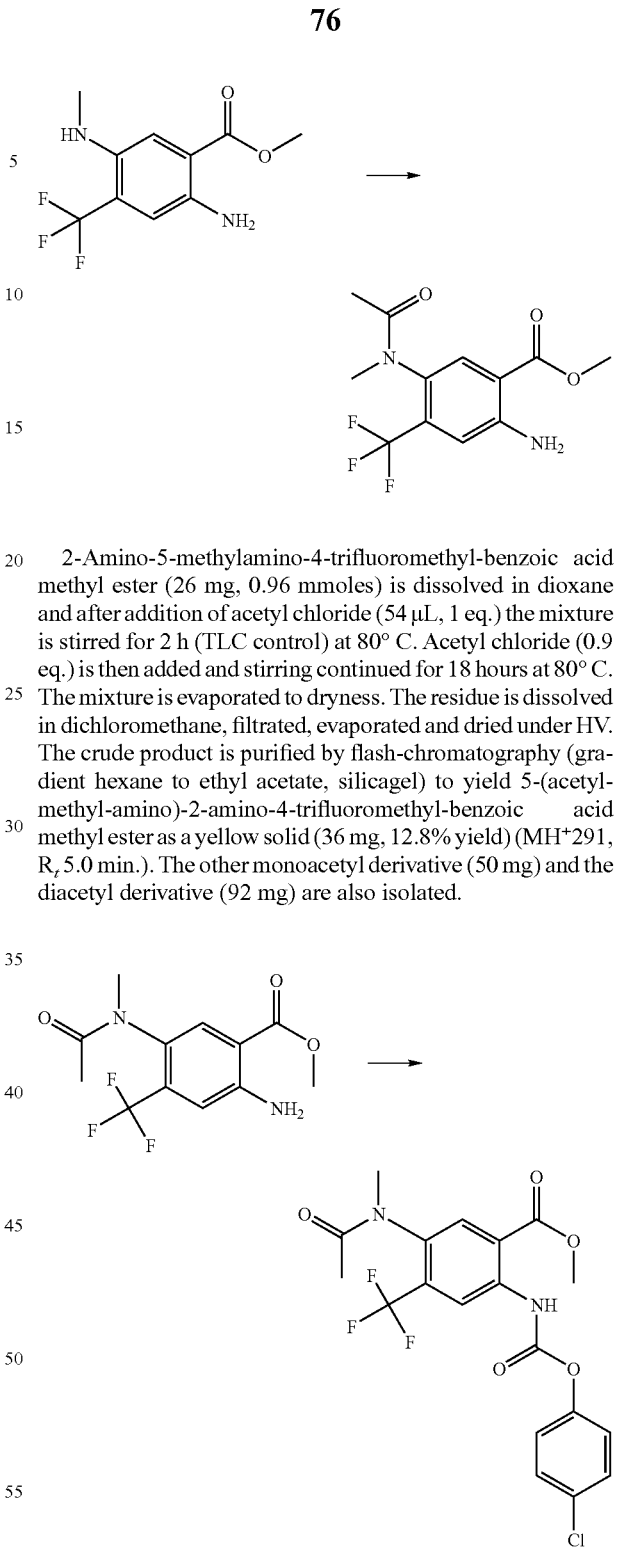

2-Amino-5-methylamino-4-trifluoromethyl-benzoic acid methyl ester (26 mg, 0.96 mmoles) is dissolved in dioxane and after addition of acetyl chloride (54 μL, 1 eq.) the mixture is stirred for 2 h (TLC control) at 80° C. Acetyl chloride (0.9 eq.) is then added and stirring continued for 18 hours at 80° C. The mixture is evaporated to dryness. The residue is dissolved in dichloromethane, filtrated, evaporated and dried under HV. The crude product is purified by flash-chromatography (gradient hexane to ethyl acetate, silicagel) to yield 5-(acetyl-methyl-amino)-2-amino-4-trifluoromethyl-benzoic acid methyl ester as a yellow solid (36 mg, 12.8% yield) ($MH^+$ 291, $R_t$ 5.0 min.). The other monoacetyl derivative (50 mg) and the diacetyl derivative (92 mg) are also isolated.

4-chlorophenyl chloroformate (26 mg, 1.1 eq.) is slowly added to a solution of 5-(acetyl-methyl-amino)-2-amino-4-trifluoromethyl-benzoic acid methyl ester (36 mg, 0.12 mmoles) in dioxane (0.2 ml). The solution is stirred at 80° C. for 2 hours. The solution is evaporated to yield 5-(acetyl-methyl-amino)-2-(4-chloro-phenoxycarbonylamino)-4-trifluoromethyl-benzoic acid methyl ester after repeated trituration with hexane. Used tel quel for the next step.

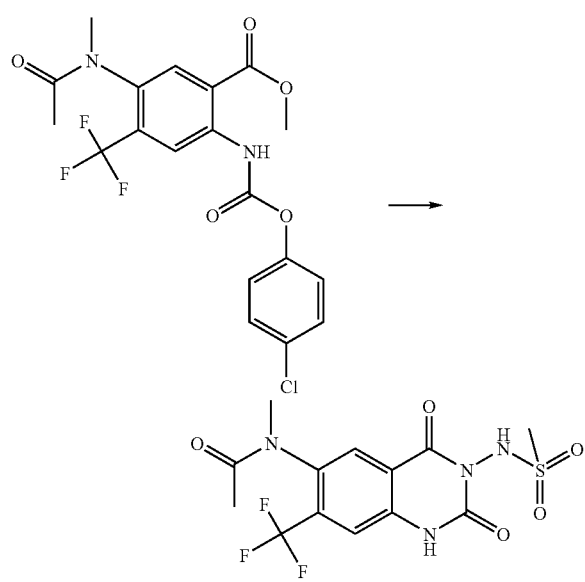

Methanesulfonyl hydrazide (15 mg, 1.1 eq.) and ethyl-diisopropyl-amine (0.042 ml, 2 eq.) are added to a solution of 5-(acetyl-methyl-amino)-2-(4-chloro-phenoxycarbonylamino)-4-trifluoromethyl-benzoic acid methyl ester (55 mg, 0.12 mmoles) in dioxane (0.5 ml). The mixture is stirred for 18 hours (TLC control) at 85° C. The mixture becomes turbid white/yellow. Then the mixture is evaporated to dryness. The residue is dissolved in dichloromethane, the solid is filtrated and dried under HV (32.8 mg, 67.3% yield) (MH$^+$395, R$_t$ 3.58 min.).

Example 88

1-(3-methanesulfonylamino-2,4-dioxo-7-trifluoromethyl-1,2,3,4-tetrahydro-quinazolin-6-yl)-1H-imidazole-4-carboxylic acid methyl ester

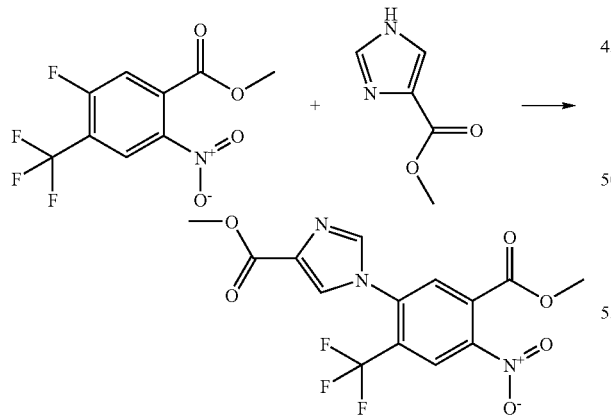

A solution of 5-fluoro-2-nitro-4-trifluoromethyl-benzoic acid methyl ester (1 g, 3.74 mmol) and 1H-imidazole-4-carboxylic acid methyl ester (0.53 g, 4.12 mmol) in 10 ml of tetrahydrofuran and 2 ml of DMSO is heated to reflux for 90 hours. The solution is allowed to cool to room temperature and evaporated. The residue is crystallized from dichloromethane and hexane to give 1.12 g (3 mmol, 80%) of 1-(5-methoxycarbonyl-4-nitro-2-trifluoromethyl-phenyl)-1H-imidazole-4-carboxylic acid methyl ester, m.p. 136-138° C., ES-MS: m/z 374 [M+H]$^+$.

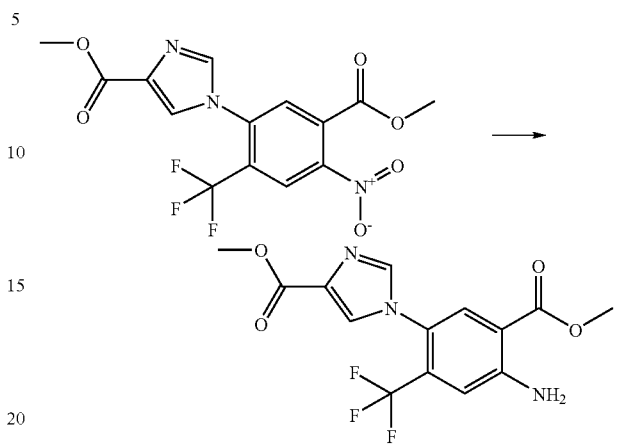

A solution of 1.1 g (2.95 mmoles) of 1-(5-methoxycarbonyl-4-nitro-2-trifluoromethyl-phenyl)-1H-imidazole-4-carboxylic acid methyl ester in 400 ml methanol is treated with 163 mg of 10% palladium on charcoal and hydrogenated at room temperature under a pressure of 5 bar for 18 hours. After filtration of the catalyst and evaporation of the solvent the residue is chromatographed on silica gel using dichlormethane and rising quantities of up to 15% of methanol. Recrystallization of the residue from dichloromethane and hexane gives 932 mg (2.715 mmol, 92%) of 1-(4-amino-5-methoxycarbonyl-2-trifluoromethyl-phenyl)-1H-imidazole-4-carboxylic acid methyl ester, m.p. 206-208° C., ES-MS: m/z 344 [M+H]$^+$.

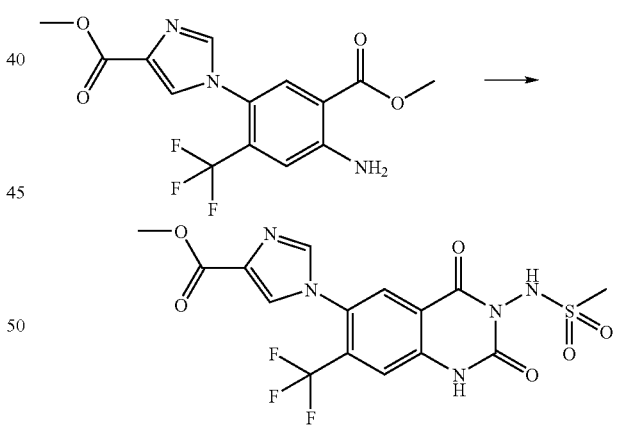

A solution of 1-(4-amino-5-methoxycarbonyl-2-trifluoromethyl-phenyl)-1H-imidazole-4-carboxylic acid methyl ester (932 mg, 2.715 mmol) in dioxane (500 ml) is treated with triphosgene (814 mg, 2.715 mmol) and the mixture is stirred at 80° C. for 3 hours. Methanesulfonylhydrazide (302 mg, 2.715 mmol) is added and stirring continued for 30 minutes. After cooling to room temperature and concentration to a volume of 50 ml 3.0 ml of a 1 M sodium hydroxide solution are added and the mixture is stirred over night at room temperature. The mixture is concentrated in vacuo and the residue chromatographed on silica gel using a gradient of dichloromethane and methanol to give after recrystallization from dichloromethane/hexane 1.035 g (2.31 mmol, 85%) of 1-(3-methanesulfonylamino-2,4-dioxo-7-trifluoromethyl-1,2,3,4-tetrahydro-quinazolin-6-yl)-1H-imidazole-4-carboxylic acid methyl ester, m.p. 287 -288° C., ES-MS: m/z 448 [M+H]⁺.

Example 89

1-(3-Methanesulfonylamino-2,4-dioxo-7-trifluoromethyl-1,2,3,4-tetrahydro-quinazolin-6-yl)-1H-imidazole-4-carboxylic acid

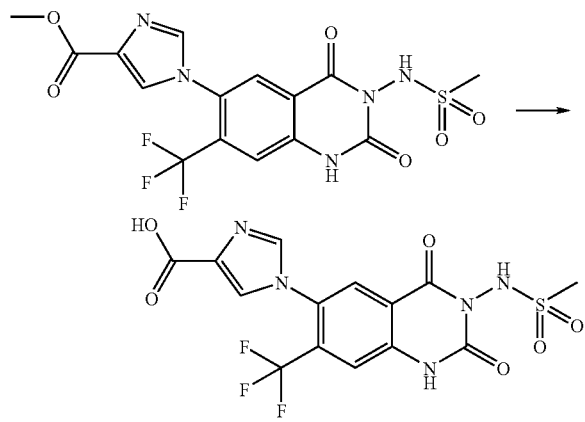

To a solution of 1-(3-methanesulfonylamino-2,4-dioxo-7-trifluoromethyl-1,2,3,4-tetrahydro-quinazolin-6-yl)-1H-imidazole-4-carboxylic acid methyl ester (150 mg, 0.335 mmol) in 10 ml dimethylformamide are added 1.7 ml of 1 M aqueous sodium hydroxide solution and stirred at room temperature for one hour and at 50° C. for two hours. After cooling to room temperature the solvent is evaporated in vacuo, the residue taken up in water, acidified with 5 ml of 1 M hydrochloric acid and extracted three times with 15 ml each of dichloromethane. The organic layer is dried over sodium sulfate, filtered and evaporated to give 126 mg (0.29 mmol, 87%) of amorphous 1-(3-methanesulfonylamino-2,4-dioxo-7-trifluoromethyl-1,2,3,4-tetrahydro-quinazolin-6-yl)-1H-imidazole-4-carboxylic acid, ES-MS: m/z 434 [M+H]⁺.

Example 90

1-(3-Methanesulfonylamino-2,4-dioxo-7-trifluoromethyl-1,2,3,4-tetrahydro-quinazolin-6-yl)-1H-imidazole-4-carboxylic acid dimethylamide

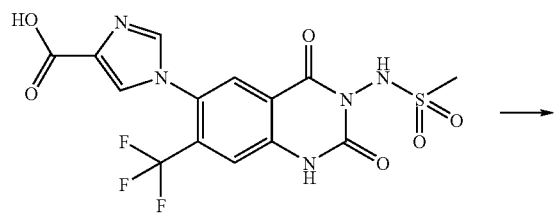

-continued

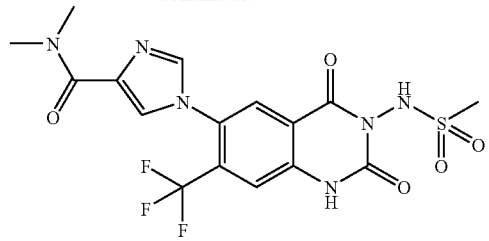

A solution of 1-(3-methanesulfonylamino-2,4-dioxo-7-trifluoromethyl-1,2,3,4-tetrahydro-quinazolin-6-yl)-1H-imidazole-4-carboxylic acid (120 mg, 0.277 mmol) in 10 ml of dimethylformamide is treated with dimethylamine hydrochloride (46 mg, 0.554 mmol), N-3-dimethylaminopropyl-N'-ethyl-carbodiimide hydrochloride (60 mg, 0.305 mmol), N-hydroxybenzotriazole (11 mg, 0.08 mmol) and triethylamine (0.1 ml, 0.72 mmol). The solution is heated to 100° C. for 1 hour, cooled to room temperature, evaporated in vacuo and the residue chromatographed over silica gel to give 22 mg (0.048 mmoles, 17%) of 1-(3-methanesulfonylamino-2,4-dioxo-7-trifluoromethyl-1,2,3,4-tetrahydro-quinazolin-6-yl)-1H-imidazole-4-carboxylic acid dimethylamide, m.p. 284-286° C., ES-MS: m/z 461 [M+H]⁺.

Example 91

1-(3-Methanesulfonylamino-2,4-dioxo-7-trifluoromethyl-1,2,3,4-tetrahydro-quinazolin-6-yl)-1H-imidazole-4-carboxylic acid methylamide

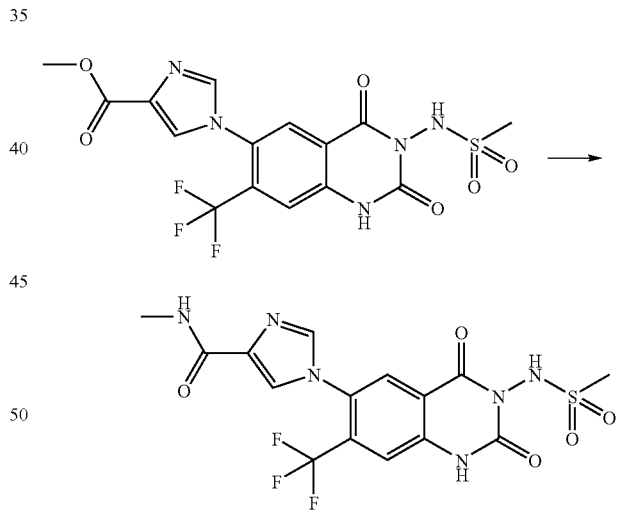

A solution of 1-(3-methanesulfonylamino-2,4-dioxo-7-trifluoromethyl-1,2,3,4-tetrahydro -quinazolin-6-yl)-1H-imidazole-4-carboxylic acid methyl ester (800 mg, 1.79 mmol) and N-methylformamide (0.357 ml, 6 mmol) in 5 ml of dimethylformamide is heated to 120° C. and sodium methylate (100 mg, 1.79 mmol) is added under stirring. After two hours at 120° C. another 100 mg of sodium methylate is added and stirring at 120° C. continued for additional two hours. After cooling to room temperature the solution is evaporated in vacuo and the residue chromatographed to give 560 mg (1.25 mmol, 70%) of 1-(3-methanesulfonylamino-2,4-dioxo-7-trifluoromethyl-1,2,3,4-tetrahydro-quinazolin-6-yl)-1H-imidazole-4-carboxylic acid methylamide, m.p. 292 -295° C., ES-MS: m/z447 [M+H]⁺.

Example 92

1-(3-Methanesulfonylamino-2,4-dioxo-7-trifluoromethyl-1,2,3,4-tetrahydro-quinazolin-6-yl)-1H-imidazole-4-carboxylic acid amide

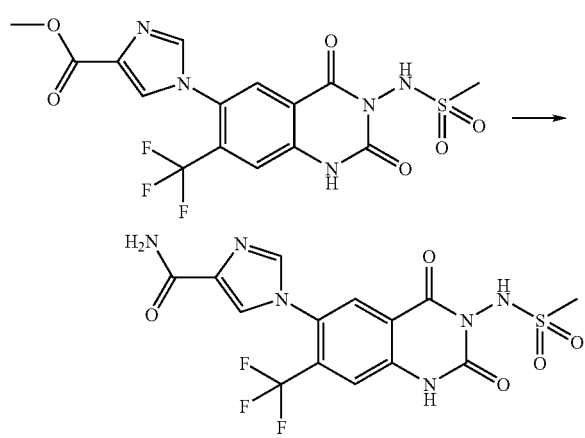

A solution of 1-(3-methanesulfonylamino-2,4-dioxo-7-trifluoromethyl-1,2,3,4-tetrahydro-quinazolin-6-yl)-1H-imidazole-4-carboxylic acid methyl ester (50 mg, 0.112 mmol) and formamide (0.15 ml, 0.374 mmol) in 5 ml of dimethylformamide is heated to 120° C. and sodium methylate (6 mg, 0.112 mmol) is added under stirring. After two hours at 120° C. the solution is cooled to room temperature, evaporated in vacuo and the residue chromatographed to give 30 mg (0.069 mmol, 62%) of amorphous 1-(3-methanesulfonylamino-2,4-dioxo-7-trifluoromethyl-1,2,3,4-tetrahydro-quinazolin-6-yl)-1H-imidazole-4-carboxylic acid amide, ES-MS: m/z 433 [M+H]⁺.

Example 93

N-[6-(4-Hydroxymethyl-imidazol-1-yl)-2,4-dioxo-7-trifluoromethyl-1,4-dihydro-2H-quinazolin-3-yl]-methanesulfonamide

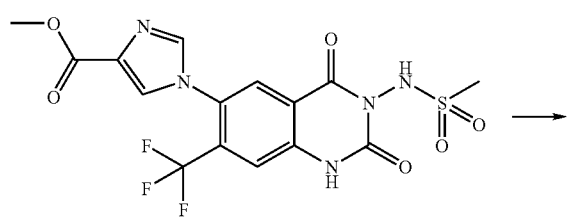

-continued

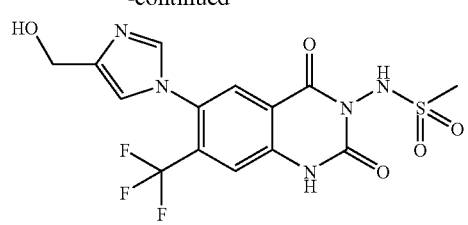

A solution of 1-(3-methanesulfonylamino-2,4-dioxo-7-trifluoromethyl-1,2,3,4-tetrahydro-quinazolin-6-yl)-1H-imidazole-4-carboxylic acid methyl ester (300 mg, 0.67 mmol) in 5 ml of a 1:1 mixture of dioxane and water is treated with sodium borohydride (40 mg, 1 mmol) and stirred overnight. After evaporation in vacuo the residue is purified by preparative HPLC to give 20 mg (0.048 mmol, 7%) of N-[16-(4-hydroxymethyl-imidazol-1-yl)-2,4-dioxo-7-trifluoromethyl-1,4-dihydro-2H-quinazolin-3-yl]-methanesulfonamide, m.p. 225-230° C., ES-MS: m/z420 [M+H]⁺.

Example 94

N-[6-(4-Cyano-imidol-1-yl)-2,4-dioxo-7-trifluoromethyl-1,4-dihydro-2H-quinazolin-3-yl]-methanesulfonamide

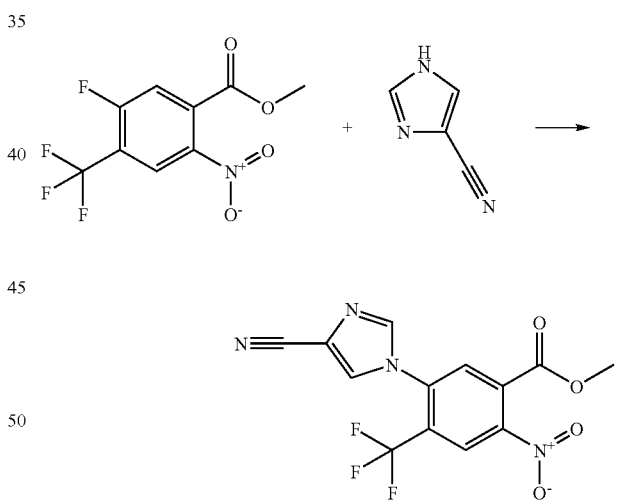

A solution of 5-fluoro-2-nitro-4-trifluoromethyl-benzoic acid methyl ester (3.2 g, 11.98 mmol), 1H-imidazole-4-carbonitrile (2.017 g, 14.37 mmol) and ethyl-diisopropyl-amine (8.4 ml, 47.9 mmol) in 10 ml of dioxane is heated to reflux for 24 hours. The solution is allowed to cool to room temperature and evaporated. The residue is chromatographed on silica gel using gradients of dichloromethane and methanol to give 0.36 g (1.05 mmol, 8.8%) of amorphous 5-(4-cyano-imidazol-1-yl)-2-nitro-4-trifluoromethyl-benzoic acid methyl ester, ES-MS: m/z 341 [M+H]⁺.

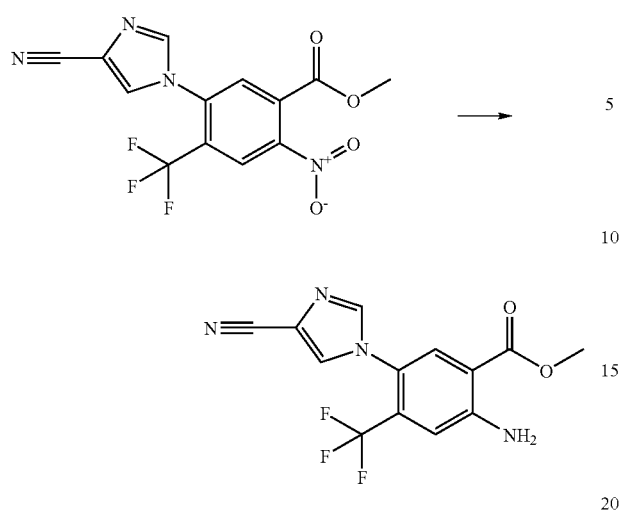

A solution of 350 mg (1.03 mmoles) of 5-(4-cyano-imidazol-1-yl)-2-nitro-4-trifluoromethyl-benzoic acid methyl ester in 100 ml methanol is treated with 22 mg of 10% palladium on charcoal and hydrogenated at room temperature under a pressure of 1 bar for 16 hours. After filtration of the catalyst and evaporation of the solvent the residue is chromatographed on silica gel using dichloromethane and rising quantities of up to 15% of methanol to give 35 mg (0.113 mmol, 11%) of amorphous 2-amino-5-(4-cyano-imidazol-1-yl)-4-trifluoromethyl-benzoic acid methyl ester, ES-MS: m/z 311 [M+H]$^+$.

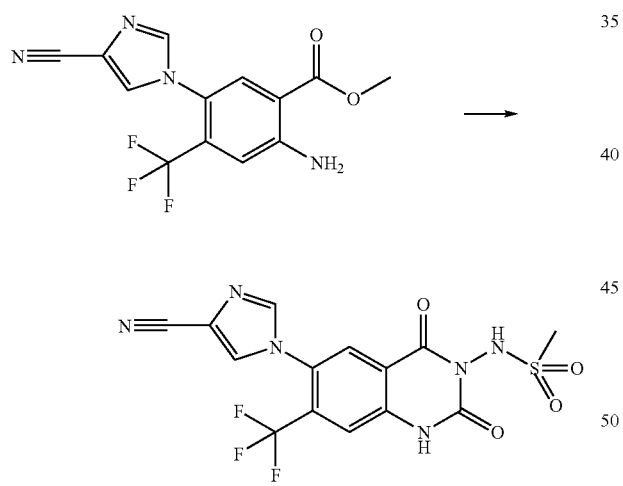

A solution of 2-amino-5-(4-cyano-imidazol-1-yl)-4-trifluoromethyl-benzoic acid methyl ester (35 mg, 0.113 mmol) in dioxane (25 ml) is treated with ethyl-diisopropyl-amine (0.5 ml, 2.86 mmol) and with triphosgene (34 mg, 0.113 mmol) and the mixture is stirred at 80° C. for 1 hour. Methanesulfonylhydrazide (13 mg, 0.113 mmol) is added and stirring is continued for 1 hour. After cooling to room temperature the solution is concentrated in vacuo and the residue chromatographed on silica gel to give 20 mg (0.048 mmol, 42%) of N-[6-(4-cyano-imidazol-1-yl)-2,4-dioxo-7-trifluoromethyl-1,4-dihydro-2H-quinazolin-3-yl]-methanesulfonamide, m.p. 143-145° C., ES-MS: m/z 415 [M+H]$^+$.

Example 95

N-[6-(4-Bromo-imidazol-1-yl)-2,4-dioxo-7-trifluoromethyl-1,4-dihydro-2H-quinazolin-3-yl]-methanesulfonamide

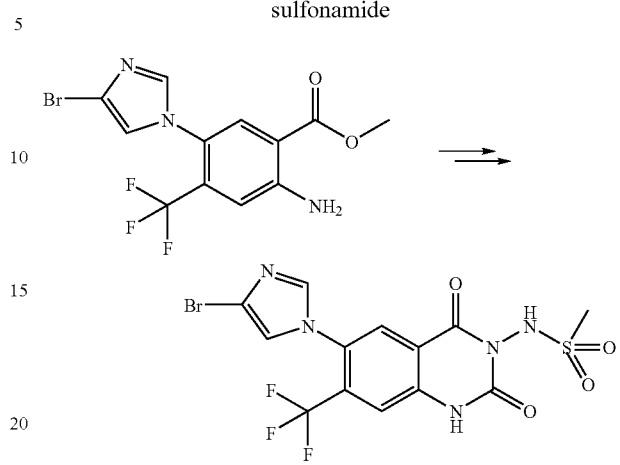

In a similar way as in the previous example a solution of 5-fluoro-2-nitro-4-trifluoromethyl-benzoic acid methyl ester (1 g, 3.73 mmol), 4-bromo-imidazole (0.68 g, 4.5 mmol) and N-ethyl-diisopropyl-amine (2.62 ml, 14.9 mmol) in 10 ml of dioxane is heated to reflux for 16 hours. After a similar workup procedure 1.4 g (3.55 mmol, 95%) of 5-(4-bromo-imidazol-1-yl)-2-nitro-4-trifluoromethyl-benzoic acid methyl ester are obtained, m.p. 90° C., ES-MS: m/z 395 [M+H]$^+$.

In a similar way a solution of 5-(4-bromo-imidazol-1-yl)-2-nitro-4-trifluoromethyl-benzoic acid methyl ester (300 mg, 0.8 mmol) in 50 ml methanol is hydrogenated over 43 mg of 10% palladium on charcoal to obtain after the usual workup procedure 160 mg (0.466 mmol, 58%) of 2-amino-5-(4-bromo-imidazol-1-yl)-4-trifluoromethyl-benzoic acid methyl ester, m.p. 163-165° C., ES-MS: m/z 365 [M+H]$^+$.

In a similar way a solution of 2-amino-5-(4-bromo-imidazol-1-yl)-4-trifluoromethyl-benzoic acid methyl ester (160 mg, 0.439 mmol) and ethyl-diisopropyl-amine (0.52 ml, 3 mmol) in 100 ml dioxane are treated first with triphosgene (132 mg, 0.439 mmol) and subsequently with methanesulfonylhydrazide (49 mg, 0.439 mmol) to give after the usual workup 95 mg (0.2 mmol, 46%) of N-[6-(4-bromo-imidazol-1-yl)-2,4-dioxo-7-trifluoromethyl-1,4-dihydro-2H-quinazolin-3-yl]-methanesulfonamide, m.p. 229-233° C., ES-MS: m/z 469 [M+H]$^+$.

Example 96

N-[6-(4-Trifluoromethyl-imidazol-1-yl)-2,4-dioxo-7-trifluoromethyl-1,4-dihydro-2H-quinazolin-3-yl]-methanesulfonamide

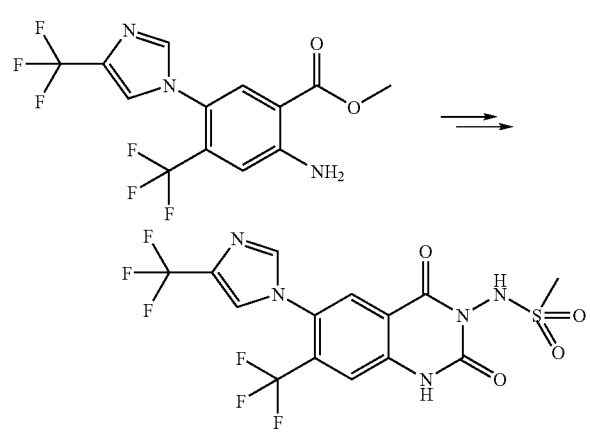

In a similar way a solution of 5-fluoro-2-nitro-4-trifluoromethyl-benzoic acid methyl ester (1.5 g, 5.62 mmol), 4-trifluoromethyl-imidazole (0.945, 6.74 mmol) and ethyl-diisopropyl-amine (3.94 ml, 22.5 mmol) in 10 ml of dioxane is heated to reflux for 48 hours. After a similar workup procedure 1.4 g (3.65 mmol, 65%) of amorphous 5-(4-trifluoromethyl-imidazol-1-yl)-2-nitro-4-trifluoromethyl-benzoic acid methyl ester are obtained, ES-MS: m/z 384 [M+H]$^+$.

In a similar way a solution of 5-(4-trifluoromethyl-imidazol-1-yl)-2-nitro-4-trifluoromethyl-benzoic acid methyl ester (1.0 g, 2.6 mmol) in 100 ml methanol is hydrogenated over 55 mg of 10% palladium on charcoal to obtain after the usual workup procedure 840 mg (2.38 mmol, 91%) of amorphous 2-amino-5-(4-trifluoromethyl-imidazol-1-yl)-4-trifluoromethyl-benzoic acid methyl ester, ES-MS: m/z 354 [M+H]$^+$.

In a similar way a solution of 2-amino-5-(4-trifluoromethyl-imidazol-1-yl)-4-trifluoromethyl-benzoic acid methyl ester (840 mg, 2.38 mmol) and ethyl-diisopropyl-amine (4 ml, mmol) in 100 ml dioxane are treated first with triphosgene (706 mg, 2.38 mmol) and subsequently with methanesulfonylhydrazide (262 mg, 2.38 mmol) to give after the usual workup 470 mg (1.03 mmol, 43%) of N-[6-(4-trifluoromethyl-imidazol-1-yl)-2,4-dioxo-7-trifluoromethyl-1,4-dihydro-2H-quinazolin-3-yl]-methanesulfonamide, m.p. 144-147° C., ES-MS: m/z 458 [M+H]$^+$.

Example 97

N-(2,4-Dioxo-6-pyrrol-1-yl-7-trifluoromethyl-1,4-dihydro-2H-quinazolin-3-yl)-methanesulfonamide

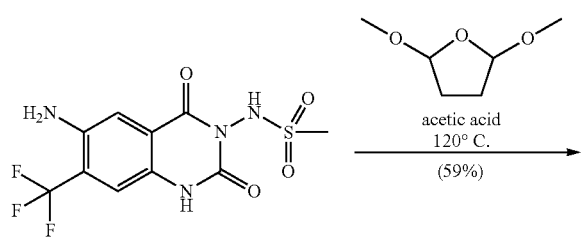

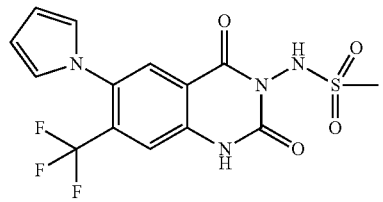

The solution of 80 mg (0.236 mmol) ) N-(6-amino-2,4-dioxo-7-trifluoromethyl-1,4-dihydro-2H-quinazolin-3-yl)-methanesulfonamide and 0.092 ml (0.709 mmol) 2,5-dimethoxy-tetrahydrofuran in 1.5 ml acetic acid is refluxed for 2 hours. After rotavapor evaporation of the solvent the residue is purified by reversed phase chromatography (C18) with an acetonitril-water gradient and the product is lyophilized to give 54 mg (59%) of N-(2,4-dioxo-6-pyrrol-1-yl-7-trifluoromethyl-1,4-dihydro-2H-quinazolin-3-yl)-methanesulfonamide as a brown solid. MS (ES$^+$): m/e=389 (M+H$^+$).

Example 98

N-[6-(3-Formyl-pyrrol-1-yl)-2,4-dioxo-7-trifluoromethyl-1,4-dihydro-2H-quinazolin-3-yl]-methanesulfonamide

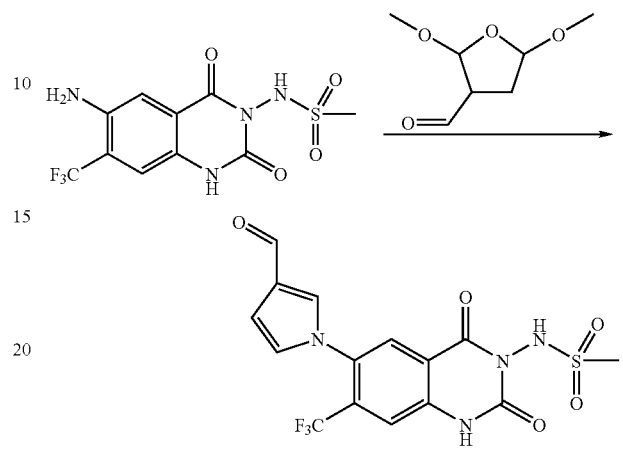

To a solution of 100 mg (0.296 mmol) of N-(6-amino-2,4-dioxo-7-trifluoromethyl-1,4-dihydro-2H-quinazolin-3-yl)-methanesulfonamide in 2 ml acetic acid is added a solution of 2,5-dimethoxy-tetrahydrofuran-3-carbaldehyde in 1 ml acetic acid and the mixture is refluxed for 3 hours. The solvent is removed by rotavapor evaporation and the brown oil is purified by reversed phase chromatography (C18) with an acetonitril-water gradient to give 80 mg (65%) of N-[6-(3-formyl-pyrrol-1-yl)-2,4-dioxo-7-trifluoromethyl-1,4-dihydro-2H-quinazolin-3-yl]-methanesulfonamide as a black solid. MS (ES$^+$): m/e=417 (M+H$^+$).

Example 99

N-[6-(2-Hydroxy-1-phenyl-ethylamino)-2,4-dioxo-7-trifluoromethyl-1,4-dihydro-2H-quinazolin-3-yl]-methanesulfonamide

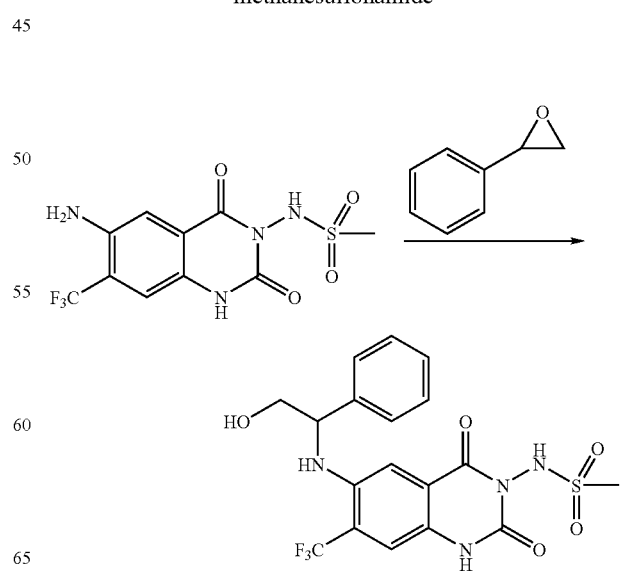

To a solution of 0.101 ml (0.887 mmol) of styrene oxide in 1 ml acetonitril 242 mg (1.77 mmol) zinc chloride are added and the mixture is stirred for 15 minutes. To the resulting white suspension 50 mg (0.148 mmol) of N-(6-amino-2,4-dioxo-7-trifluoromethyl-1,4-dihydro-2H-quinazolin-3-yl)-methanesulfonamide are added and the mixture is stirred at 70° C. for 90 minutes. Another 0.017 ml (0.147 mmol) of styrene oxide are added and the mixture is stirred for another 30 minutes at 70° C. The solvent is evaporated by rotavapor evaporation. The residue is dissolved in ethyl acetate and washed with an aqueous solution of potassium carbonate (1M) and with an aqueous solution of citric acid (10%). The crude product is purified by reversed phase (C18) chromatography using an acetonitril-water gradient. Upon lyophilisation 12 mg (18%) of N-[6-(2-hydroxy-1-phenyl-ethylamino)-2,4-dioxo-7-trifluoromethyl-1,4-dihydro-2H-quinazolin-3-yl]-methanesulfonamide are obtained as a yellowish solid. MS (ES$^+$): m/e =459 (M+H$^+$).

Example 100

1-(3-Benzenesulfonylamino-2,4-dioxo-7-trifluoromethyl-1,2,3,4-tetrahydro-quinazolin-6-yl)-1H-imidazole-4-carboxylic acid

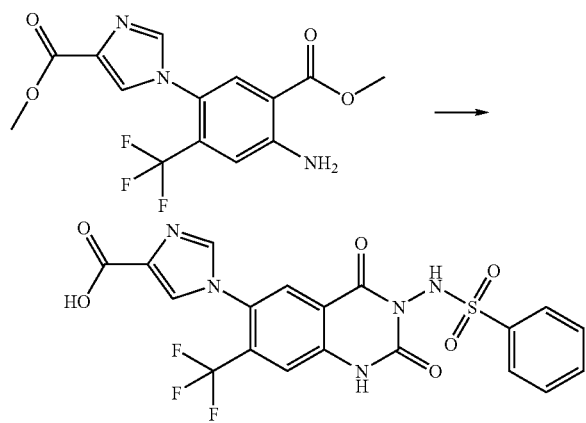

200 mg (0.58 mmole) of 1-(4-amino-5-methoxycarbonyl-2-trifluoromethyl-phenyl)-1H-imidazole-4-carboxylic acid methyl ester are suspended in 3 ml tetrahydrofuran and 209 mg (0.71 mmol) of triphosgene are added. 10 minutes later are added 0.112 ml of di-isopropyl-ethylamine to the suspension. The clear solution is stirred for additional two hours at room temperature and half of the solvent is evaporated. Subsequently a solution of 121 mg (0.705 mmol) benzenesulphonyl hydrazide in dry tetrahydrofuran is added via a syringe. The resulting suspension is stirred for 20 min at 60° C., then treated with 2 ml of a 1 M aqeous sodium hydroxide solution and stirred for 6 hours at room temperature to complete saponification of the ester. After evaporation of the solvents the residue is dissolved in ethyl acetate, the extraction solvent is dried, filtered and evaporated to yield 1-(3-benzenesulfonylamino-2,4-dioxo-7-trifluoromethyl-1,2,3,4-tetrahydro-quinazolin-6-yl)-1H-imidazole-4-carboxylic acid. $^1$H-NMR; DMSO-d$_6$ (400 MHz, ppm): 8.15 (s, 1H, imidazole); 8.10 (s, 1H, imidazole); 7.99 (s, 1H, aromatic); 7.71 (s, 1H, aromatic); LC-MS: 494 [M–H]$^-$; Agilent LC/MSD 1100 Series; LC-MS method: Column: SunFireC18, 4.6*50 mm, 3.5 µm; negative MS; water/acetonitril 95:5 to 5:95 in 5 min, flow: 1.5 ml/min.

The starting material 1-(4-amino-5-methoxycarbonyl-2-trifluoromethyl-phenyl)-1H-imidazole-4-carboxylic acid methyl ester is prepared as follows:

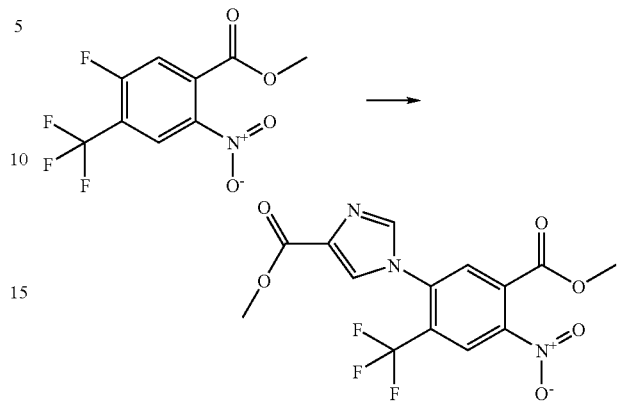

To a solution of 8.00 g (29.95 mmol) of 5-fluoro-2-nitro-4-trifluoromethyl-benzoic acid methyl ester in 40 ml dry tetrahydrofuran, 5.40 g (42.00 mmol) of 1H-imidazole-4-carboxylic acid methyl ester are added. The reaction mixture is stirred at 70° C. for 48 hours (after 16 hours addition of 0.3 equivalents of 1H-imidazole-4-carboxylic acid methyl ester). Subsequently the solvent is evaporated and the light brown residue is extracted with dichloromethane. The combined organic extracts are dried, the solvent evaporated to give light purple crystals. The crude product is purified by flash-master chromatography (dichloromethane/methanol 100-90/0-10 gradient) to yield 1-(5-methoxycarbonyl-4-nitro-2-trifluoromethyl-phenyl)-1H-imidazole-4-carboxylic acid methyl ester. $^1$H-NMR; DMSO-d$_6$ (400 MHz, ppm): 8.71 (s, 1H, aromatic); 8.31 (s, 1H, aromatic); 8.27 (s, 1H, imdazole); 8.09 (s, 1H, imdazole); 3.92 (s, 3H Ar-COOCH3); 3.80 (s, 3H, COOCH3); LC-MS: 374 [M+H]+; Agilent LC/MSD 1100 Series; LC-MS method: Column: SunFireC18, 4.6*50 mm, 3.5 µm; positive MS; water/acetonitril 95:5 to 5:95 in 5 min, flow: 1.5 ml/min.

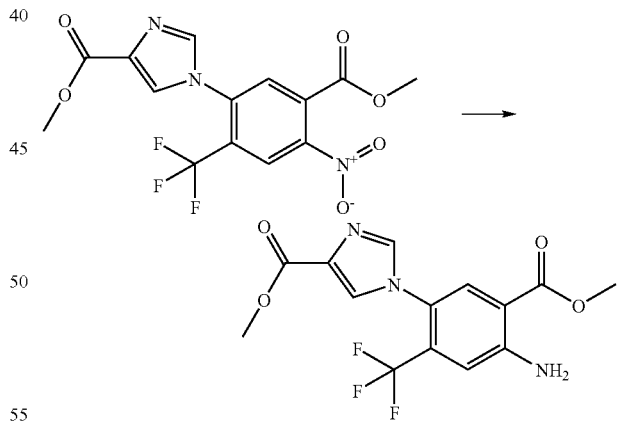

A solution of 4.4 g (11.79 mmol) of 1-(5-methoxycarbonyl-4-nitro-2-trifluoromethyl-phenyl)-1H-imidazole-4-carboxylic acid methyl ester in 400 ml methanol is treated with 400 mg of 10% palladium on charcoal and hydrogenated at room temperature under a pressure of 60 psi for 2 hours. After filtration of the catalyst through hyflo and evaporation of the solvent pure 1-(4-amino-5-methoxycarbonyl-2-trifluoromethyl-phenyl)-1H-imidazole-4-carboxylic acid methyl ester is obtained as a white solid. $^1$H-NMR; DMSO-d$_6$ (400 MHz, ppm): 8.03 (s, 1H, aromatic); 7.87 (s, 1H, aromatic); 7.78 (s, 1H, imdazole); 7.35 (s, 1H, imdazole); 3.82 (s, 3H, Ar-COOCH3); 3.77 (s, 3H, COOCH3); LC-MS: 344

Example 101

(3-Methanesulfonylamino-2,4-dioxo-7-trifluoromethyl-1,2,3,4-tetrahydro-quinazolin-6-yl)carbamic acid methyl ester

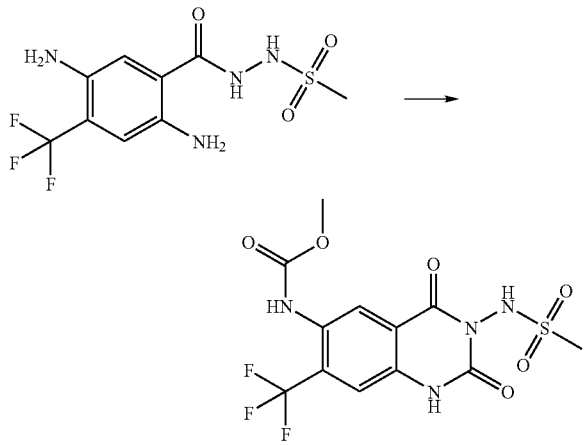

To the solution of 40 mg (0.12 mmol) of N-(2,5-diamino-4-trifluoromethyl-benzoyl)-methanesulfonhydrazide in 1 ml tetrahydrofuran and 0.04 ml ethyl-diisopropyl-amine, 0.11 ml (0.20 mmol) of phosgene solution in toluene (0.94 g/ml) are added. The reaction is stirred at 110° C. in the microwave reactor for 10 min. The mixture is cooled to room temperature and poured into methanol, the solvents are evaporated to give a yellow solid. The crude product is extracted with ethyl acetate and water. The organic fractions are combined, dried and evaporated to yield (3-methanesulfonylamino-2,4-dioxo-7-trifluoromethyl-1,2,3,4-tetrahydro-quinazolin-6-yl)carbamic acid methyl ester: m.p. 232.4-240.2° C. $^1$H-NMR; DMSO-$d_6$ (400 MHz, ppm): 7.95 (s, 1H , aromatic); 7.51 (s, 1H, aromatic); 3.64 (s, 3H, COOCH3); 3.15 (s, 3H, SO2CH3). LC-MS: 397 [M+H]+; Agilent LC/MSD 1100 Series; LC-MS method: Column: SunFireC18, 4.6*50 mm, 3.5 µm; positive MS; water/acetonitril 95:5 to 5:95 in 5 min, flow: 1.5 ml/min.

The starting material N-(2,5-diamino-4-trifluoromethyl-benzoyl)-methanesulfonhydrazide is prepared as follows:

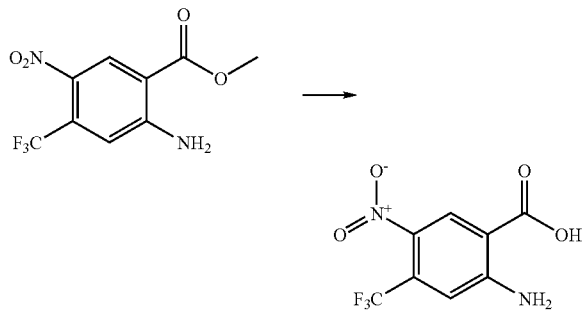

To a solution of 490 mg (1.85 mmol) of 2-amino-5-nitro-4-trifluoromethyl-benzoic acid methyl ester in 5 ml methanol, 4.7 ml (9.27 mmol) of 2 M sodium hydroxide solution is added. The yellow solution is stirred at 60° C. for 12 hours. Subsequently hydrochloric acid (1M) is added to adjust to pH=2. The solvent volume is reduced by evaporation and is extracted with ethyl acetate. The organic layers are combined, dried and the solvent is evaporated to yield 2-amino-5-nitro-4-trifluoromethyl-benzoic acid. $^1$H-NMR; DMSO-$d_6$ (400 MHz, ppm): 8.58 (s, 1H, aromatic); 8.10 (s(broad), 2H, NH2); 7.35 (s, 1H, aromatic).; LC-MS: 249 [M-H]- ; Agilent LC/MSD 1100 Series; LC-MS method: Column: SunFireC18, 4.6*50 mm, 3.5 µm; negative MS; water/acetonitril 95:5 to 5:95 in 5 min, flow: 1.5 ml/min.

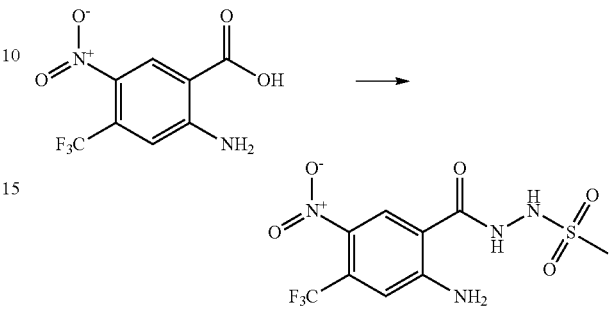

To a solution of 400 mg (1.60 mmol) of 2-amino-5-nitro-4-trifluoromethyl-benzoic acid in 1 ml dimethylformamide, 363 mg (1.76 mmol) of N,N'-dicyclohexylcarbodiimide and 0.21 ml (1.92 mmol) of N-methyl morpholine are added and the solution is allowed to stir at room temperature for 10 min. Subsequently 73 mg (0.48 mmol) of 1-hydroxybenzotriazole monohydrate and 705 mg (6.40 mmol) of methanesulphonyl hydrazide are added and the reaction mixture is stirred at 40° C. for 12 hours. The solvents are evaporated and the yellow residue is extracted with ethyl acetate and 1 M hydrochloric acid solution. The organic fractions are combined, dried, evaporated and purified by flash-master chromatography (0-40% gradient of cyclohexane/ethyl acetate) to yield N-(2-amino-5-nitro4-trifluoromethyl-benzoyl)-methanesulfonhydrazide: m.p. 221.2-226.8° C.; $_1$H-NMR; DMSO-$d_6$ (400 MHz, ppm): 8.54 (s, 1H, aromatic); 7.89 (s(broad), 2H, NH2); 7.33 (s, 1H, aromatic); 3.02 (s, 3H, SO2-CH3). LC-MS: 341 [M–H]⁻; Agilent LC/MSD 1100 Series; LC-MS method: Column: SunFireC18, 4.6*50 mm, 3.5 µm; negative MS; water/acetonitril 95:5 to 5:95 in 5 min, flow: 1.5 ml/min.

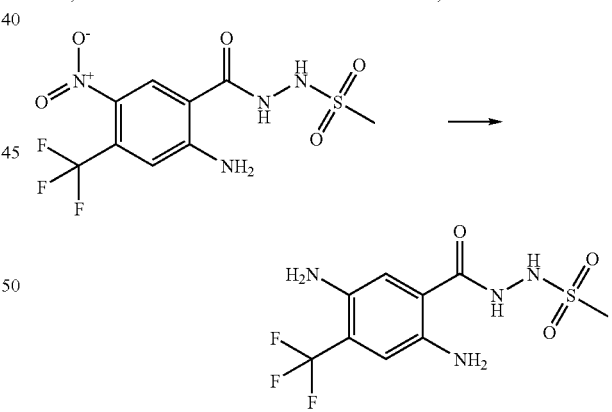

To a solution of 80 mg (0.23 mmol) of N-(2-amino-5-nitro-4-trifluoromethyl-benzoyl)-methanesulfonhydrazide in 1.5 ml of conc. hydrochloric acid, 270 mg (1.17 mmol) of tin(II) chloride dihydrate is added and the mixture is stirred at room temperature for 20 min. The mixture is neutralized at 0° C. with an aqueous solution of ammonia. The product is extracted with ethyl acetate. The combined organic fractions are dried, evaporated and purified by flash-master chromatography (0-70% gradient cyclohexane/ethyl acetate) to yield N-(2,5-diamino-4-trifluoromethyl-benzoyl)-methanesulfonhydrazide as hydrochloride salt. M.p. 220.8 -225.5° C.; $^1$H-NMR; DMSO-$d_6$ (400 MHz, ppm): 6.98 (s, 1H, aromatic); 6.88 (s, 1H, aromatic); 2.98 (s, 3H, S02-CH3). LC-MS: 313 [M+H]+; Agilent LCIMSD 1100 Series; LC-MS method: Column: SunFireC 18, 4.6*50 mm, 3.5 µm; positive MS; water/acetonitril 95:5 to 5:95 in 5 min, flow: 1.5 ml/min.

Example 102

N-[6-(2-Methyl-pyrrol -1-yl)-2,4-dioxo-7-trifluoromethyl-1,4-dihydro-2H-quinazolin-3-yl]-methanesulfonamide

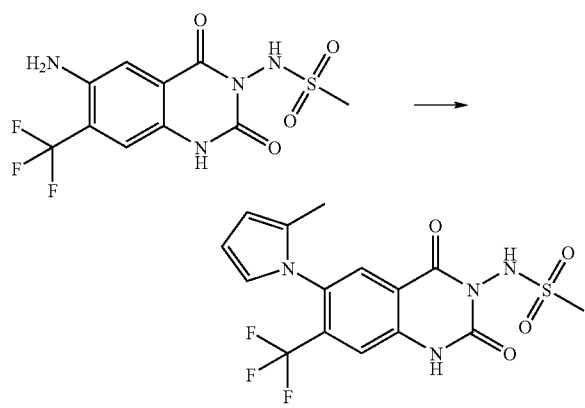

To a solution of 200 mg (0.59 mmol) of N-(6-amino-2,4-dioxo-7-trifluoromethyl-1,4-dihydro-2H-quinazolin-3-yl)-methanesulfonamide in 10 ml of acetic acid, 87 mg (0.60 mmol) of 2-methyl-2,5-dimethoxy-tetrahydrofuran is added and the reaction mixture is stirred at reflux for 5 hours. Subsequently the solvent is evaporated and the residue is dried for 1 day at 60° C. and high vacuum to yield N-[6-(2-methyl-pyrrol-1-yl)-2,4-dioxo-7-trifluoromethyl-1,4-dihydro-2H-quinazolin-3-yl]-methanesulfonamide. $^1$H-NMR; DMSO-$d_6$ (400 MHz, ppm): 7.69 (s, 1H, aromatic); 7.54 (s, 1H , aromatic); 6.6 (s, 1H, N-CH=CH in pyrrol); 5.97 (t, 1H, CH=CH=CH in pyrrol); 5.83 (m, 1H, CH=CH-C(CH3)-N in pyrrol); 3.05 (s, 3H, SO2-CH3); 1.82 (s, 3H, pyrrol-1-CH3). LC-MS: 403 [M+H]+; Agilent LC/MSD 1100 Series; LC-MS method: Column: SunFireC18, 4.6*50 mm, 3.5 µm; positive MS; water/acetonitril 95:5 to 5:95 in 5 min, flow: 1.5 ml/min.

Example 103

1-(3-Benzenesulfonylamino-2,4-dioxo-7-trifluoromethyl-1,2,3,4-tetrahydro-quinazolin-6-yl)-1H-imidazole-4-carboxylic acid methyl ester

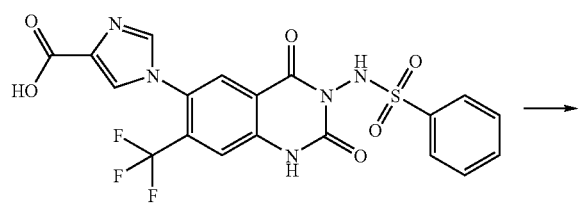

-continued

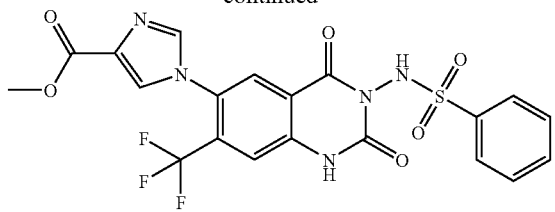

A solution of 20 mg (0.04 mmol) of 1-(3-benzenesulfonylamino-2,4-dioxo-7-trifluoromethyl-1,2,3,4-tetrahydro-quinazolin-6-yl)-1H-imidazole-4-carboxylic acid in 50 ml of a 6 M solution of hydrochloric acid in methanol is stirred at 70° C. for two days. Every half day another 50 ml of a 6 M solution of hydrochloric acid in methanol is added. Subsequently the solvent and hydrochloric acid are evaporated to yield 1-(3-benzenesulfonylamino-2,4-dioxo-7-trifluoromethyl-1,2,3,4-tetrahydro-quinazolin-6-yl)-1H-imidazole-4-carboxylic acid methyl ester: $^1$H-NMR; DMSO-$d_6$ (400 MHz, ppm): 8.16 (s, 1H, imidazole); 8.10 (s, 1H, aromatic); 7.98 (s, 1H, imidazole); 7.70 (s, 1H, aromatic); 3.79 (s, 3H, COOCH3). LC-MS: 510 [M+H]+; Agilent LC/MSD 1100 Series, LC-MS method: Column: SunFireC8, 4.6*50 mm, 3.5 µm; positive MS; water/acetonitril 95:5 to 5:95 in 5 min, flow: 1.5 ml/min.

Example 104

Acetic acid 1-(3-methanesulfonylamino-2,4-dioxo-7-trifluoromethyl-1,2,3,4-tetrahydro-quinazolin-6-yi)-1H-pyrrol-3-ylmethyl ester

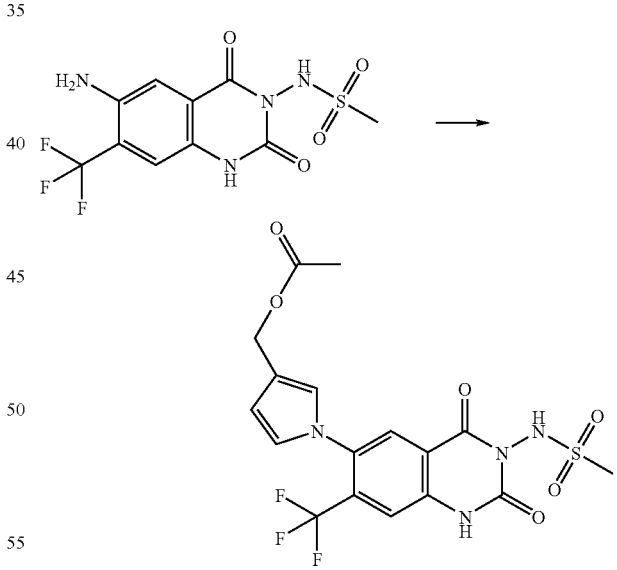

To a solution of 130 mg (0.39 mmol) of N-(6-amino-2,4-dioxo-7-trifluoromethyl-1,4-dihydro-2H-quinazolin-3-yl)-methanesulfonamide in 5 ml of acetic acid a solution of 95 mg (0.39 mmol) of 2-(2,5-dimethoxy-tetrahydro-furan-3-yl-methoxy)-tetrahydro-pyran (prepared according to Frydman, Benjamin; Ojea, Maria I. 1,4-*Diaminobutanes from furans: a new synthetic approach to substituted putrescines*. Tetrahedron Letters (1998), 39(27), 4765-4768) is added and the reaction mixture is stirred at reflux for 3 hours. The solvent is evaporated at HV overnight to yield acetic acid 1-(3-methanesulfonylamino-2,4-dioxo-7-trifluoromethyl-1,2,3,4-tetrahydro-quinazolin-6-yl)-1H-pyrrol-3-ylmethyl ester. $^{1}$H-NMR ; DMSO-$d_6$ (400 MHz, ppm): 7.85 (s, 1H , aromatic); 7.62 (s, 1H , aromatic); 7.03 (s, 1H, N-CH=C(CH2) in pyrrol); 6.91 (m, 1H, N-CH=CH in pyrrol); 6.27 (m, 1H, CH=CH-C(CH2)-N in pyrrol); 4.96 (s, 2H, CH2-OCOCH3); 3.16 (s, 3H, SO2-CH3); 2.03 (s, 3H, CH2-OCOCH3); LC-MS: 459 [M-H]-; Agilent LC/MSD 1100 Series, LC-MS method: Column: SunFireC18, 4.6*50 mm, 3.5 μm; negative MS; water/acetonitril 95:5 to 5:95 in 5 min, flow: 1.5 ml/min.

Example 105

N-[6-(3-Hydroxymethyl-pyrrol-1-yl)-2,4-dioxo-7-trifluoromethyl-1,4-dihydro-2H-quinazolin-3-yl]-methanesulfonamide

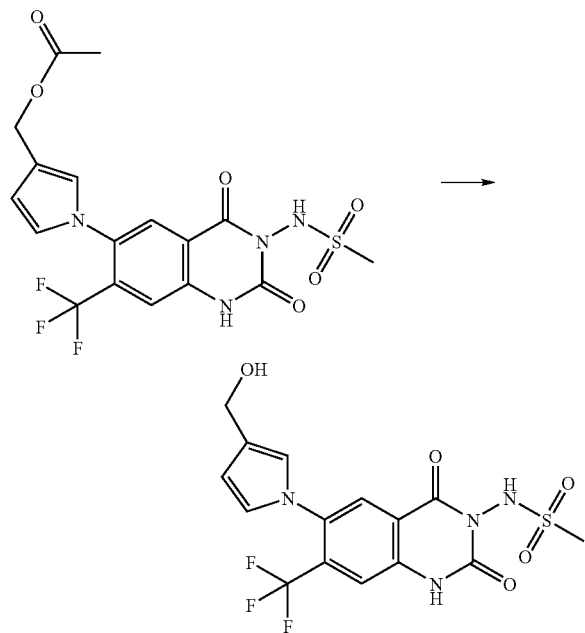

To a solution of 100 mg (0.22 mmol) of acetic acid 1-(3-methanesulfonylamino-2,4-dioxo-7 -trifluoromethyl-1,2,3, 4-tetrahydro-quinazolin-6-yl)-1H-pyrrol-3-ylmethyl ester in 0.5 ml of methanol are added 36.4 mg (0.26 mmol) of potassium carbonate and the reaction mixture is stirred at 55° C. for 8 hours. The mixture is cooled to room temperature and stirred for another 12 hours. Subsequently a pH 7 phosphate buffer solution for neutralization is added to the reaction mixture and the solvents are evaporated carefully (risk of degradation). The crude residue is purified by preparative thin layer chromatography (dichloromethane/methanol, 8/2) to yield N-[6-(3-hydroxymethyl-pyrrol-1-yl)-2,4-dioxo-7-trifluoromethyl-1,4-dihydro-2H-quinazolin-3-yl]-methanesulfonamide: $^{1}$H-NMR; DMSO-$d_6$ (400 MHz, ppm): 7.82 (s, 1H , aromatic); 7.64 (s, 1H , aromatic); 6.86 (m, 1H, N-CH=CH in pyrrol); 6.84 (s, 1H, N-CH=C(CH2) in pyrrol); 6.21 (m, 1H, CH=CH-C(CH2)-N in pyrrol); 4.37 (d, 2H, CH2-OH); 3.16 (s, 3H, S02-CH3); LC-MS: 417 [M-H]-; Agilent LC/MSD 1100 Series, LC-MS method: Column: SunFireC18, 4.6*50 mm, 3.5 μm; negative MS; water/acetonitril 95:5 to 5:95 in 5 min, flow: 1.5 ml/min.

Example 106

N-[6-(4-Methyl-2-oxo-2,3-dihydro-pyrrol-1-yl)-2,4-dioxo-7-trifluoromethyl-1,4-dihydro-2H-quinazolin-3-yl]-methanesulfonamide To a solution of 60 mg (0.18 mmol) of N-(6-amino-2,4-dioxo-7-trifluoromethyl-1,4-dihydro-2H-quinazolin-3-yl)-methanesulfonamide in 5 ml of acetic acid are added 26 mg (0.18 mmol) of 2,5-dimethoxy-3-methyl-tetrahydro-furan (prepared according to: Markwell, Roger Edward; Hadley, Michael Stewart; Blaney, Frank Edward. Azabicycloalkane derivatives and medicaments containing them. Eur. Pat. Appl. (1983) EP 95262 A1). The reaction mixture is stirred at reflux for 10 hours. Subsequently the solvents are evaporated and the crude product is purified by flash-master chromatography (cyclohexane/ethyl acetate, from 100/0 to 20/80) to yield N-[6-(4-methyl-2-oxo-2,3-dihydro-pyrrol-1-yl)-2,4-dioxo-7-trifluoromethyl-1,4-dihydro-2H-quinazolin-3-yl] methanesulfonamide. $^{1}$H-NMR ; DMSO-$d_6$ (400 MHz, ppm):; 8.06 (s, 1H, aromatic); 7.60 (s, 1H , aromatic); 7.13 (m, 1H, N-CH=C(CH3)); 4.24 CO—CH2-C(s, 2CO—CH2-C (CH3)); 3.16 (s, 3H, S02-CH3); 1.84 (d, 3H, CH3) [M–H]-; Agilent LC/MSD 1100 Series, LC-MS method: Column: SunFireC18, 4.6*50 mm, 3.5 μm; negative MS; water/acetonitril 95:5 to 5:95 in 5 min, flow: 1.5 ml/min.

Biological Assays

AMPA-Receptor Binding

This can be demonstrated in standard tests, e.g. the [$^{3}$H] CNQX binding test (Honoré et al. Biochem. Pharmacol. 1989, 38: 3207-3212). This test is performed as follows:

Brain membranes: The animals are decapitated, the brain removed and homogenized in 10 volumes of ice-cold 10% sucrose with a glass/Teflon homogenizer at positions 5 for 30 sec. The membranes are centrifuged at 1000×g for 10 min, and the supernatant centrifuged at 20,000×g for 15 min. The resulting pellet is resuspended in 10 volumes of cold water with a tissue homogenizer (Brinkman Polytron) at position 5 for 15 sec and the suspension centrifuged at 8000×g for 10 min. The supernatant including the buffy layer is centrifuged at 40,000×g for 20 min, the pellet resuspended in 5 volumes of water and the suspension frozen (20-30 min in dry ice/methanol) and thawed (water-bath at 37° C.) twice. The suspension is centrifuged at 40,000×g for 20 min, the pellet resuspended in 50 mM HEPES/KOH, pH 7.5, and centrifuged at 40,000×g for 10 min. The final pellet is resuspended with a glass/Teflon homogenizer in 5 volumes of HEPES/KOH buffer; 2 ml aliquots are frozen and stored in liquid nitrogen.

Pretreatment of membranes: Membranes are thawed at 35° C. and once washed with 50 mM HEPES/KOH by centrifugation at 39,000×g for 10 min. The final pellet is resuspended with a glass/Teflon homogenizer in the same buffer.

Radioligand binding assay: It is performed using 96-well microtiterplates in a volume of 0.3 ml of 50 mM HEPES/KOH, pH 7.2, 100 µg membrane protein, 5 nM [$^3$H]-CNQX (NEN) and the compound to be tested. Incubation is performed at 4° C. for 40 min and the reaction is terminated by centrifugation (Sigma 4K10) at 3700×g for 30 min. The pellet is washed once with cold buffer and then dissolved in 0.02 ml of the tissue solubilizer Soluene for 20 min. Two hundred µl of the scintillation fluid Microscint 20 (Packard) are added and the radioactivity is counted in a Packard Topcount scintillation counter at an efficiency of 40-45%. Nonspecific binding is defined by 10 µM CNQX. Assays are performed in triplicate. For example, in this assay the compound of Example 4 has an $IC_{50}$ of 0.29 µM.

Functional Test for AMPA-Receptor Activity

For the determination of functional agonism or antagonism at the AMPA-receptor, experiments can be performed on *Xenopus* oocytes as previously described in detail (Urwyler et al., *Mol. Pharmacol.* 2001, 60, 963-971). Briefly, two electrode voltage clamp recordings are performed from *Xenopus laevis* oocytes expressing GluR3 AMPA receptors. Plasmids for the rat GluR3-(flop) (Hollmann et al., *Science* 1991, 252, 851-853) are linearized and transcribed into capped cRNA using an in vitro RNA synthesis kit (Ambion, Tex.) with T7 Polymerase. Stock solutions are kept in 70% ethanol. Before use, cRNA is precipitated and resuspended in DEPC-treated water. Oocytes are injected with RNA coding the rat GluR3-(flop) AMPA receptor. For recordings, oocytes are placed in a perfusion chamber with continuous gravity flow of frog Ringer's solution. For recordings from oocytes expressing rGluR3-(flop) receptors frog, Ringer's solution containing $Mg^{2+}$ (81 mM NaCl; 2.5 mM KCl; 1 mM $CaCl_2$; 1 mM $MgCl_2$, 2.5 mM $NaHCO_3$, 5 mM HEPES, pH 7.4) is used. Test compounds are washed in with gravity.

For example, in this assay the compound of Example 4 is an antagonist at the rGluR3 AMPA receptor with an $IC_{50}$-value of 2.3 µM.

Audiogenic Seizures Model

For example the compounds of the invention have pronounced anticonvulsive properties which are determined in vivo, for example in mice, by reference to their pronounced protective action with respect to convulsions triggered by sound, electric shock or metrazole. Sound induced seizures are elicited in DBA/2 mice (Collins R L in: Experimental models of epilepsy, eds Pupura, Penry Tower, Woodbury Walter; Raven Press, New York, 1972). For testing, 20-day-old animals are placed in a sound attenuated chamber. Following a 60 s habituation period the animals are stimulated using band limited noise (14-20 kHz, 118 dB SPL) lasting for maximally 60 s. DBA/2 mice respond with a sequence of wild running, clonic seizures, tonic seizures, and respiratory arrest to the acoustic stimulus. For data analysis the occurrence as well as the duration of the different behavioural phases are measured. The ED50 values for the different behavioural phases are calculated. ED50 values following systemic drug applications (intraperitoneal, subcutaneous, oral) range between 0.5 mg/kg and 100 mg/kg.

In addition, the compounds of the invention show pronounced effects in the well established electric shock mouse model or the mouse model for metrazole-induced convulsions according to Schmutz et al, *Naunyn-Schmiedeberg's Arch Pharmacol* 1990, 342, 61-66. ED50 values range between 1 mg/kg and 200 mg/kg.

The antischizophrenic activity of the compounds of the invention can be demonstrated, e.g. in the amphetamine-induced hyperlocomotion test. Blockade of amphetamine-induced hyperlocomotion is well known as screening paradigm for antischizophrenic activity.

Further, the compounds of formula (I) (also referred to as AMPA receptor antagonist ) may be combined with other active ingredients (a "combined preparation").

The structure of other active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutical effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

Such combined preparations have beneficial pharmaceutical effects, for example such preparations show a synergistic effect. The combined preparations may be used in the indications named in this specification. The invention provides the method of use of combined preparations for the prevention, treatment, delay of progression of disorders and diseases identified in this specification.

The below given combinations and uses are of particular relevance.

Thus, in a further aspect the invention relates to a combination, which comprises at least one compound of formula (I) ("AMPA receptor antagonist") and at least one nootropic. In such a combination the active ingredients are present in each case in free form or in the form of a pharmaceutically acceptable salt and optionally at least one pharmaceutically acceptable carrier; for simultaneous, separate or sequential use.

The term "nootropics" as used herein includes, but is not limited to nootropical plant extracts, calcium antagonists, cholinesterase inhibitors, dihydroergotoxin, nicergoline, piracetame, purine derivates, pyritinol, vincamine and vinpocetine. In a preferred embodiment of the invention, the combination partner is a cholinesterase inhibitor.

The term "nootropical plant extracts" as used herein includes, but is not limited to extracts from Ginkgo leafs. The term "calcium antagonists" as used herein includes, but is not limited to cinnarizine and nimodipine. The term "cholinesterase inhibitors" as used herein includes, but is not limited to donepezil hydrochloride, rivastigmine and galantamine hydrobromide. The term "purine derivates" as used herein includes, but is not limited to pentifyllin.

Extracts from Ginkgo leafs can be administered, e.g., in the form as marketed, e.g. under the trademark Ginkodilat™ according to the information provided by the package insert. Cinnarizine can be administered, e.g., in the form as marketed, e.g. under the trademark Cinnarizin forte-ratiopharm™. Nimodipine can be administered, e.g., in the form as marketed, e.g. under the trademark Nimotop™. Donepezil hydrochloride can be administered, e.g., in the form as marketed, e.g. under the trademark Aricept™. Rivastigmine can be prepared as disclosed in U.S. Pat. No. 5,602,176. It can be administered, e.g., in the form as marketed, e.g. under the trademark Exelon™. Galantamine hydrobromide can be administered, e.g., in the form as marketed, e.g. under the trademark Reminyl™. Dihydroergotoxin can be administered, e.g., in the form as marketed, e.g. under the trademark Hydergin™. Nicergoline can be administered, e.g., in the form as marketed, e.g. under the trademark Sermion™. Piracetam can be administered, e.g., in the form as marketed, e.g. under the trademark Cerebroforte™. Pentifyllin can be administered, e.g., in the form as marketed, e.g. under the trademark Cosaldon™. Pyritinol can be administered, e.g., in the form as marketed, e.g. under the trademark Encephabol™. Vinpocetin can be administered, e.g., in the form as marketed, e.g. under the trademark Cavinton™.

The structure of the active ingredients identified by code nos., generic or trade names mentioned herein may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

When the combination partners employed in the COMBINATION OF THE INVENTION are applied in the form as marketed as single drugs, their dosage and mode of administration can take place in accordance with the information provided on the packet leaflet of the respective marketed drug in order to result in the beneficial effect described herein, if not mentioned herein otherwise. In particular, Cinnarizine may be administered to a patient in a total daily dosage of between about 75 to about 150 mg. Nimodipine may be administered to a patient in a total daily dosage of between about 60 to about 120 mg. Donepezil hydrochloride may be administered to a patient in a total daily dosage of between about 5 mg and 10 mg. Rivastigmine may be administered to a patient in a total daily dosage of between about 6 and about 12 mg. Galantamine may be administered to a patient in a total daily dosage of between about 12 and 24 mg, e.g. 12 mg twice daily. Dihydroergotoxin may be administered in the form of its methansulfonate to a patient in a total daily dosage of between about 4 mg and 10 mg, e.g. about 8 mg. Nicergoline may be administered in the form of its tartrate by intramuscular injection to a patient in a total daily dosage of between about 4 mg and 8 mg. Piracetam may be administered to a patient in a total daily dosage of between about 1200 and 5000 mg, e.g. 4800 mg/day. Pentifyllin may be administered to a patient in a total daily dosage of between about 400 and 800 mg. Pyritinol may be administered in the form of its hydrochloride to a patient in a total daily dosage of about 600 mg. Vinpocetin may be administered to a patient in a total daily dosage of between about 10 and 15 mg.

In a further aspect, the invention provides a combination which comprises at least one AMPA receptor antagonist and at least one compound selected from the group consisting of (a) anti-epileptic drugs selected from barbiturates and derivatives thereof, benzodiazepines, carboxamides, hydantoins, succinimides, valproic acid and other fatty acid derivates and other anti-epileptic drugs, and/or (b) conventional antipsychotics and/or (c) atypical antipsychotics is greater than the additive effect of the combined drugs. Furthermore, the combinations disclosed herein can be used to treat schizophrenia which is refractory to monotherapy employing one of the combination partners alone.

The term "barbiturates and derivatives thereof" as used herein includes, but is not limited to phenobarbital, pentobarbital, mepobarbital and primidon. The term "benzodiazepines" as used herein includes, but is not limited to clonazepam, diazepam and lorazepam. The term "carboxamides" as used herein includes, but is not limited to carbamazepine, oxcarbazepine, 10-hydroxy-10,11-dihydrocarbamazepine and the compounds of formula II

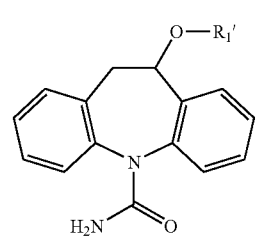

(II)

wherein $R_1'$ represents $C_1$-$C_3$alkyl carbonyl. The term "hydantoins" as used herein includes, but is not limited to phenytoin. The term "succinimides" as used herein includes, but is not limited to ethosuximide, phensuximide and mesuximide. The term "valproic acid and other fatty acid derivates" as used herein includes, but is not limited to valproic acid sodium salt, tiagabine hydrochloride monohydrate and vigrabatrine. The term "other anti-epileptic drugs" as used herein includes, but is not limited to levetiracetam, lamotrigine, gabapentin, sultiam, felbamate, the 1,2,3-1H-triazoles disclosed in EP 114 347 and the 2-aryl-8-oxodihydro-purines disclosed in WO99/28320.

The term "conventional antipsychotics" as used herein includes, but is not limited to haloperidol, fluphenazine, thiotixene and flupentixol.

The term "atypical antipsychotics" as used herein relates to clozaril, risperidone, olanzapine, quetiapine, ziprasidone and aripiprazol.

The structure of the active ingredients identified by code nos., generic or trade names and their preparation may be taken from the actual edition of the standard compendium "The Merck Index" (e.g.M. J. O'Neil et al., ed., 'The Merck Index', 13$^{th}$ ed., Merck Research Laboratories, 2001) or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

In still a further aspect the invention provides a combination which comprises at least one AMPA receptor antagonist and at least one compound selected from the group consisting of anti-anxiety drugs, antidepressants, antihistamines, anticonvulsants, vasodilators, zinc salts and anesthetics is greater than the additive effect of the combined drugs. Furthermore, the combinations disclosed herein can be used to treat tinnitus which is refractory to monotherapy employing one of the combination partners alone.

Hence, the invention relates to a combination, such as a combined preparation or pharmaceutical composition, which comprises at least one AMPA receptor antagonist and at least one compound selected from the group consisting of anti-anxiety drugs, antidepressants, antihistamines, anticonvulsants, vasodilators, zinc salts and anesthetics, in which the active ingredients are present in each case in free form or in the form of a pharmaceutically acceptable salt and optionally at least one pharmaceutically acceptable carrier; for simultaneous, separate or sequential use.

The term "AMPA receptor antagonists" as used herein includes compounds of formula (I)

The term "anti-anxiety drug" as used herein includes, but is not limited to alprazolam.

The term "antidepressants" as used herein includes, but is not limited to nortriptyline (N-methyl-3-(10,11-dihydro-5H-dibenzo[a,d]cyclohepten-5-yliden)propylamine).

The term "anticonvulsants" as used herein includes, but is not limited to oxcarbazepine.

The term "anesthetics" as used herein includes, but is not limited to lidocaine.

The term "vasodilators" as used herein includes, but is not limited to pentoxifylline.

The term "zinc salts" as used herein includes, but is not limited to zinc sulfate.

Topiramate can be administered, e.g., in the form as marketed, e.g. under the trademark Topamax™. The compounds of formula I as well as their production process and pharmaceutical compositions thereof are known, e.g., from WO 98/17672. Alprazolam can be administered, e.g., in the form as marketed, e.g. under the trademark Xanax™. Nortriptyline can be administered, e.g., in the form as marketed, e.g. under the trademark Nortrilen™. Oxcarbazepine can be administered, e.g., in the form as marketed, e.g. under the trademark Trileptal™. Lidocaine can be administered in the form of its hydrochloride, e.g., in the form as marketed as injection solution, e.g. under the trademark Heweneural™. zinc sulfate can be administered, e.g., in the form as marketed, e.g. under the trademark Zink-Sandoz™. Pentoxifyllin can be administered, e.g., in the form as marketed, e.g. under the trademark Trental™. The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

In still a further aspect, the invention provides a combination which comprises a compound of formula (I) and a anti-epileptic drug selected from the list consisting of barbiturates and derivatives thereof, benzodiazepines, carboxamides, hydantoins, succinimides, valproic acid and other fatty acid derivates and other anti-epileptic drugs. The therapeutic effect of such combination is greater than the additive effect of one single drug. Furthermore, the combinations disclosed herein can be used to treat epilepsy which is refractory to monotherapy employing one of the combinations alone.

Hence, the invention relates to a combination, such as a combined preparation or pharmaceutical composition, which comprises two anti-epileptics selected from the list consisting of barbiturates and derivatives thereof, benzodiazepines, carboxamides, hydantoins, succinimides, valproic acid and other fatty acid derivates, AMPA antagonists and other anti-epileptic drugs, in which the active ingredients are present in each case in free form or in the form of a pharmaceutically acceptable salt and optionally at least one pharmaceutically acceptable carrier; for simultaneous, separate or sequential use.

The term "barbiturates and derivatives thereof" as used herein includes, but is not limited to phenobarbital, pentobarbital, mepobarbital and primidon. The term "benzodiazepines" as used herein includes, but is not limited to clonazepam, diazepam and lorazepam. The term "carboxamides" as used herein includes, but is not limited to carbamazepine, oxcarbazepine, 10-hydroxy-10,11-dihydrocarbamazepine and the compounds of formula II In still a further aspect, the invention provides a combination which comprises at least one compound of formula (I) ("AMPA receptor antagonist") and at least one compound selected from the group consisting of lithium, valproic acid sodium salt, conventional antipsychotics, atypical antipsychotics, lamotrigine, methylphenidate, antidepressants and antiepileptics is greater than the additive effect of the combined drugs.

Furthermore, such combinations can be used to treat affective and attention disorders which is refractory to monotherapy employing one of the combination partners alone.

Hence, the invention relates to a combination, such as a combined preparation or pharmaceutical composition, which comprises at least one AMPA receptor antagonist and at least one compound selected from the group consisting of lithium, valproic acid sodium salt, conventional antipsychotics, atypical antipsychotics, lamotrigine, methylphenidate, antidepressants and antiepileptics, in which the active ingredients are present in each case in free form or in the form of a pharmaceutically acceptable salt and optionally at least one pharmaceutically acceptable carrier; for simultaneous, separate or sequential use.

The term "affective and attention disorders" as used herein includes, but is not limited to bipolar disorder, e.g. manic-depressive psychoses, mania with or without psychotic feature, attention deficit hyperactivity disorder (ADHD), and other attention disorders, e.g. autism, as well as those behavioural states characterized by social withdrawal, e.g., negative symptoms.

The term "lithium" as used herein includes, but is not limited to lithium acetate, lithium carbonate, lithium chloride, lithium citrate and lithium sulfate. The term "conventional antipsychotics" as used herein includes, but is not limited to haloperidol and fluphenazine. The term "atypical antipsychotics" as used herein includes, but is not limited to olanzapine, quetiapine and risperidone. The term "antidepressants" as used herein includes, but is not limited to tricyclic antidepressants, selective serotonin reuptake inhibitors (SSRI's), or selective serotonin and norepinephrine reuptake inhibitors (SNRI-s). A tricyclic antidepressant suitable for the present invention is especially selected from amitriptyline, butriptyline, clomipramine, desipramine, dibenzepin, dothiepin, doxepin, imipramine, nortriptyline, opipramol, protriptyline, trimipramine, maprotiline, mianserin, and mirtazepine. An SSRI suitable for the present invention is especially selected from fluoxetine, fluvoxamine, sertraline, paroxetine, citalopram and escitalopram, and an SNRI selected from venlafaxine and duloxetine.

The term "anti-epileptics" as used herein includes, but is not limited to barbiturates and derivatives thereof, benzodiazepines, carboxamides, hydantoins, succinimides, valproic acid and other fatty acid derivates, AMPA antagonists and other anti-epileptic drugs, in which the active ingredients are present in each case in free form or in the form of a pharmaceutically acceptable salt and optionally at least one pharmaceutically acceptable carrier; for simultaneous, separate or sequential use.

The term "barbiturates and derivatives thereof" as used herein includes, but is not limited to phenobarbital, pentobarbital, mepobarbital and primidon. The term "benzodiazepines" as used herein includes, but is not limited to clonazepam, diazepam and lorazepam. The term "carboxamides" as used herein includes, but is not limited to carbamazepine, oxcarbazepine, 10-hydroxy-10,11-dihydrocarbamazepine and the compounds of formula II

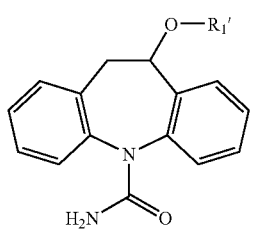

(II)

wherein $R_1'$ represents $C_1$-$C_3$alkyl carbonyl. The term "hydantoins" as used herein includes, but is not limited to phenytoin. The term "succinimides" as used herein includes, but is not limited to ethosuximide, phensuximide and mesuximide. The term "valproic acid and other fatty acid derivates" as used herein includes, but is not limited to valproic acid sodium salt, tiagabine hydrochloride monohydrate and vigrabatrine. The term "other anti-epileptic drugs" as used herein includes, but is not limited to levetiracetam, lamotrigine, gabapentin, sultiam, felbamate, the 1,2,3-1H-triazoles disclosed in EP 114 347, esp. rufinamide [1-(2,6-difluoro-benzyl)-1H-[1,2,3]triazole-4-carboxylic acid amide] and the 2-aryl-8-oxodihydropurines disclosed in WO99/28320.

In still a further aspect, the invention provides a combination which comprises at least one compound of formula (I) ("AMPA receptor antagonist") and at least one compound selected from the group consisting of benzodiazepines, selective serotonin reuptake inhibitors (SSRIs), selective serotonin and norepinephrine reuptake inhibitors (SNRIs), buspirone and pregabalin is greater than the additive effect of the combined drugs. Furthermore, the combinations disclosed herein can be used to treat anxiety disorders or other psychiatric disorders with underlying anxiety symptomatologies which are refractory to monotherapy employing one of the combination partners alone.

Hence, the invention relates to a combination, such as a combined preparation or pharmaceutical composition, which comprises at least one AMPA receptor antagonist and at least one compound selected from the group consisting-of benzodiazepines, SSRIs, SNRIs, buspirone and pregabalin, in which the active ingredients are present in each case in free form or in the form of a pharmaceutically acceptable salt and optionally at least one pharmaceutically acceptable carrier; for simultaneous, separate or sequential use.

The term "anxiety or other psychiatric disorders with underlying anxiety symptomatologies" as used herein includes, but is not restricted to anxiety disorders, such as general anxiety disorder, social anxiety disorder, post traumatic stress disorder, obsessive compulsive disorder, panic and anxiety occurring following cessation of psychostimulants or intake of other psychotropics with abuse potential.

An SSRI suitable for the present invention is especially selected from fluoxetine, fuvoxamine, sertraline, paroxetine, citalopram and escitalopram.

An SNRI suitable for the present invention is especially selected from venlafaxine and duloxetine.

The term "benzodiazepines" as used herein includes, but is not limited to clonazepam, diazepam and lorazepam.

In still a further aspect, the invention provides a combination which comprises at least one compound of formual (I) ("AMPA receptor antagonist") and at least one least one compound selected from the group consisting of pirenzepine, telenzepine, ortho-methoxy-sila-hexocyclium, γ-amino butyric acid (GABA) and GABA agonists is greater than the additive effect of the combined drugs. Furthermore, the combinations disclosed herein can be used to treat myopia which is refractory to monotherapy employing one of the combination partners alone.

Hence, the invention relates to a combination, such as a combined preparation or pharmaceutical composition, which comprises at least one AMPA receptor antagonist and at least one compound selected from the group consisting of pirenzepine, telenzepine, ortho-methoxy-sila-hexocyclium, γ-amino butyric acid (GABA) and GABA agonists, in which the active ingredients are present in each case in free form or in the form of a pharmaceutically acceptable salt and optionally at least one pharmaceutically acceptable carrier; for simultaneous, separate or sequential use.

Topiramate can be administered, e.g., in the form as marketed, e.g. under the trademark Topamax™. The compounds of formula I as well as their production process and pharmaceutical compositions thereof are known e.g. from WO 98/17672.

Pirenzepine, telenzepine and ortho-methoxy-sila-hexocyclium can be applied as described in U.S. Pat. No. 5,122,522.

The term "γ-amino butyric acid (GABA) and GABA agonists" as used herein includes, but is not limited to the compounds disclosed in WO03/032975.

In still a further aspect, the invention provides a combination which comprises at least one AMPA receptor antagonist and at least one combination partner selected from the group consisting of cyclooxygenase inhibitors, vanilloid receptor antagonists, opioids, tricyclic antidepressants, anticonvulsants, cathepsin S inhibitors and $GABA_B$ receptor agonists is greater than the additive effect of the combined drugs. Furthermore, the combinations disclosed herein can be used to treat pain, which is refractory to monotherapy employing one of the combination partners alone.

Hence, the invention relates to a combination, such as a combined preparation or pharmaceutical composition, which comprises at least one AMPA receptor antagonist and at least one combination partner selected from the group consisting of cyclooxygenase inhibitors, vanilloid receptor antagonists, opioids, tricyclic antidepressants, anticonvulsants, cathepsin S inhibitors and $GABA_B$ receptor agonists, in which the active ingredients are present in each case in free form or in the form of a pharmaceutically acceptable salt and optionally at least one pharmaceutically acceptable carrier; for simultaneous, separate or sequential use.

The term "pain" relates in particular, but is not limited to, neuropathic pain.

The term cyclooxigenase inhibitors as used herein includes, but is not limited to specific COX-2 inhibitors, e.g. celecoxib and rofecoxib, and nonsteroidal anti-inflammatory drugs (NSAIDs), e.g. acetylsalicylic acid and propionic acid derivatives.

The term "tricyclic antidepressants" as used herein includes, but is not limited to Anafranil®, Asendin®, Aventyl®, Elavil®, Endep®, Norfranil®, Norpramin®, Pamelore®, Sinequan®, Surmontil®, Tipramine®, Tofranil®, Vivactil® and Tofranil-PM®.

The term "anticonvulsants" as used herein includes, but is not limited to oxcarbazepine and gabapentin. The term "cathepsin S inhibitors" as used herein includes, but is not limited to the compounds disclosed in WO03/020287. The term "$GABA_B$ receptor agonists" as used herein includes, but is not limited to L-baclofen.

The term "opioid" as used herein refers to all drugs, both natural and synthetic, with morphine-like actions. An opioid suitable for the present invention is especially selected from the group comprising alfentanil, allylprodine, alphaprodine, anileridine, benzylmorphine, bezitramide, buprenorphine, butorphanol, clonitazene, codeine, cyclorphan, desomorphine, dextromoramide, dezocine, diampromide, dihydrocodeine, dihydromorphine, eptazocine, ethylmorphine, fentanyl, hydrocodone, hydromorphone, hydroxypethidine, levophenacylmorphan, levorphanol, lofentanil, methylmorphine, morphine, necomorphine, normethadone, normorphine, opium, oxycodone, oxymorphone, pholcodine, profadol and sufentanil.

The invention claimed is:
1. Compounds of the formula (I)

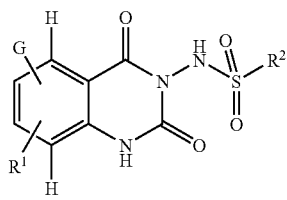

(I)

wherein G is in the 6-position and $R^1$ is in the 7-position of the benzpyrimidin-dione;

G is $NR^3R^4$;

$R^3$ and $R^4$ together with the adjacent nitrogen atom form a mono- or polycyclic aromatic 5- to 10-membered heteroaryl residue being attached via this nitrogen ring atom and containing one or more hetero ring atoms; wherein said residue is unsubstituted or substituted by substituents selected from halogen, nitro, cyano, formyl, carboxamido, hydroxyl, amino, $(C_1-C_4)$-alkylamino, di-$(C_1-C_4)$-alkylamino, $(C_1-C_4)$-alkyl, $(C_1-C_4)$-alkoxy, $(C_1-C_4)$-alkoxycarbonyl, $(C_1-C_4)$-alkanesulfonyl, $(C_1-C_4)$-alkyl-carbonyl, $(C_1-C_4)$-alkoxycarbonylamino, $(C_1-C_4)$-alkylcarbonylamino, aryl, $(C_1-C_8)$-alkyl-alkyl, substituted by aryl, aryloxy-$(C_1-C_8)$-alkyl, aminocarbonyl-$(C_1-C_8)$ mono-$(C_1-C_8)$-alkyl-aminocarbonyl-$(C_1-C_8)$-alkyl, di-$(C_1-C_8)$-alkyl-aminocarbonyl-$(C_1-C_8)$-alkyl and morpholinocarbonyl-$(C_1-C_8)$-alkyl, wherein the aryl groups are selected from phenyl, naphthyl and a mono- or polycyclic aromatic 5- to 10-membered heteroaryl containing one or more hetero ring atoms, and wherein the aryl groups themselves are unsubstituted or substituted by substituents selected from halogen, nitro, cyano, formyl, carboxamido, hydroxyl, amino, $(C_1-C_4)$-alkylamino, di-$(C_1-C_4)$-alkylamino, $(C_1-C_4)$-alkyl, $(C_1-C_4)$-alkoxy, $(C_1-C_4)$-alkoxycarbonyl, $(C_1-C_4)$-alkanesulfonyl, $(C_1-C_4)$-alkyl-carbonyl, $(C_1-C_4)$-alkoxycarbonylamino and $(C_1-C_4)$-alkylcarbonylamino;

or $R^3$ and $R^4$ together with the adjacent nitrogen atom form a mono- or polycyclic saturated or partially unsaturated heterocyclyl residue containing three to ten ring atoms being attached via this nitrogen ring atom and wherein one or more of the ring atoms are hetero atoms; wherein said residue is unsubstituted or substituted by substituents selected from halogen, nitro, cyano, formyl, carboxamido, hydroxyl, amino, $(C_1-C_4)$-alkylamino, di-$(C_1-C_4)$-alkylamino, $(C_1-C_4)$-alkyl, $(C_1-C_4)$-alkoxy, $(C_1-C_4)$-alkoxycarbonyl, $(C_1-C_4)$-alkanesulfonyl, $(C_1-C_4)$-alkyl-carbonyl, $(C_1-C_4)$-alkoxycarbonylamino, $(C_1-C_4)$-alkylcarbonylamino, aryl, $(C_1-C_8)$-alkyl substituted by aryl, aryloxy-$(C_1-C_8)$-alkyl, aminocarbonyl-$(C_1-C_8)$-alkyl, mono-$(C_1-C_8)$-alkyl-aminocarbonyl-$(C_1-C_8)$-alkyl, di-$(C_1-C_8)$-alkyl-aminocarbonyl-$(C_1-C_8)$-alkyl and morpholinocarbonyl-$(C_1-C_8)$-alkyl, wherein the aryl groups are selected from phenyl, naphthyl and a mono- or polycyclic aromatic 5- to 10-membered heteroaryl containing one or more hetero ring atoms, and wherein the aryl groups themselves are unsubstituted or substituted by substituents selected from halogen, nitro, cyano, formyl, carboxamido, hydroxyl, amino, $(C_1-C_4)$-alkylamino, di-$(C_1-C_4)$-alkylamino, $(C_1-C_4)$-alkyl, $(C_1-C_4)$-alkoxy, $(C_1-C_4)$-alkoxycarbonyl, $(C_1-C_4)$-alkanesulfonyl, $(C_1-C_4)$-alkyl-carbonyl, $(C_1-C_4)$-alkoxycarbonylamino and $(C_1-C_4)$-alkylcarbonylamino;

$R^1$ is nitro or trifluoromethyl;

$R^2$ is $(C_1-C_8)$-alkyl, aryl or $(C_1-C_8)$-alkyl substituted by aryl, wherein the aryl groups are selected from phenyl, naphthyl and a mono- or polycyclic aromatic 5- to 10-membered heteroaryl containing one or more hetero ring atoms, and wherein the aryl groups themselves are unsubstituted or substituted by substituents selected from halogen, nitro, cyano, formyl, carboxamido, hydroxyl, amino, $(C_1-C_4)$-alkylamino, di-$(C_1-C_4)$-alkylamino, $(C_1-C_4)$-alkyl, $(C_1-C_4)$-alkoxy, $(C_1-C_4)$-alkoxycarbonyl, $(C_1-C_4)$-alkanesulfonyl, (C₁-C₄)-alkyl-carbonyl, (C₁-C₄)-alkoxycarbonylamino and (C₁-C₄)-alkylcarbonylamino;
and their physiologically acceptable salts.

2. A compound of the formula (I) according to claim 1, wherein said compound is selected from the group consisting of N-(6-Imidazol-1-yl-7-nitro-2,4-dioxo-1,4-dihydro-2H-quinazolin-3-yl)-methanesulfonamide;
N-[6-(4-Hydroxymethyl-imidazol-1-yl)-7-nitro-2,4-dioxo-1,4-dihydro-2H-quinazolin-3-yl]-methanesulfonamide;
N-(6-Morpholin-4-yl-7-nitro-2,4-dioxo-1,4-dihydro-2H-quinazolin-3-yl)-methanesulfonamide;
N-(7-Nitro-2,4-dioxo-6-pyrrol-1-yl-1,4-dihydro-2H-quinazolin-3-yl)-methanesulfonamide;
N-[6-(3-Formyl-pyrrol-1-yl)-7-nitro-2,4-dioxo-1,4-dihydro-2H-quinazolin-3-yl]-methanesulfonamide;
N-[6-(4-Bromo-imidazol-1-yl)-7-nitro-2,4-dioxo-1,4-dihydro-2H-quinazolin-3-yl]-methanesulfonamide;
N-[7-Nitro-2,4-dioxo-6-(4-phenyl-imidazol-1-yl)-1,4-dihydro-2H-quinazolin-3-yl]-methanesulfonamide;
N-{6-[4-(4-Methoxy-phenyl)-imidazol-1-yl]-7-nitro-2,4-dioxo-1,4-dihydro-2H-quinazolin-3-yl}-methanesulfonamide;
N-[7-Nitro-2,4-dioxo-6-(4-phenyl-piperazin-1-yl)-1,4-dihydro-2H-quinazolin-3-yl]-methanesulfonamide;
N-[6-(2-Methyl-imidazol-1-yl)-7-nitro-2,4-dioxo-1,4-dihydro-2H-quinazolin-3-yl]-methanesulfonamide;
N-{6-[4-(4-Acetyl-phenyl)-piperazin-1-yl]-7-nitro-2,4-dioxo-1,4-dihydro-2H-quinazolin-3-yl}-methanesulfonamide;
N-(7-Nitro-2,4-dioxo-6-[1,2,4]triazol-1-yl-1,4-dihydro-2H-quinazolin-3-yl)-methanesulfonamide;
N-[7-Nitro-2,4-dioxo-6-(2-phenoxy-ethylamino)-1,4-dihydro-2H-quinazolin-3-yl]-methanesulfonamide;
N-(7-Nitro-2,4-dioxo-6-pyrazol-1-yl-1,4-dihydro-2H-quinazolin-3-yl)-methanesulfonamide;
N-[6-(4-Methyl-imidazol-1-yl)-7-nitro-2,4-dioxo-1,4-dihydro-2H-quinazolin-3-yl]-methanesulfonamide;
N-[6-(3-Hydroxy-pyrrolidin-1-yl)-7-nitro-2,4-dioxo-1,4-dihydro-2H-quinazolin-3-yl]-methanesulfonamide;
N-(7-Nitro-2,4-dioxo-6-pyrrolidin-1-yl-1,4-dihydro-2H-quinazolin-3-yl)-methanesulfonamide;
N-{6-[4-(2-Morpholin-4-yl-2-oxo-ethyl)-imidazol-1-yl]-7-nitro-2,4-dioxo-1,4-dihydro-2H-quinazolin-3-yl}-methanesulfonamide;
N-[6-(4,5-Dimethyl-imidazol-1-yl)-7-nitro-2,4-dioxo-1,4-dihydro-2H-quinazolin-3-yl]-methanesulfonamide;
N-Allyl-2-[1-(3-methanesulfonylamino-7-nitro-2,4-dioxo-1,2,3,4-tetrahydro-quinazolin-6-yl)-1H-imidazol-4-yl]-acetamide;
N-[6-((S)-3-Hydroxy-pyrrolidin-1-yl)-7-nitro-2,4-dioxo-1,4-dihydro-2H-quinazolin-3-yl]-methanesulfonamide;
N-[6-((R)-3-Hydroxy-pyrrolidin-1-yl)-7-nitro-2,4-dioxo-1,4-dihydro-2H-quinazolin-3-yl]-methanesulfonamide;
N-(6-Azetidin-1-yl-7-nitro-2,4-dioxo-1,4-dihydro-2H-quinazolin-3-yl)-methanesulfonamide;
N-(7-Nitro-2,4-dioxo-6-[1,2,3]triazol-1-yl-1,4-dihydro-2H-quinazolin-3-yl)-methanesulfonamide;
N-[6-(4-Cyanomethyl-imidazol-1-yl)-7-nitro-2,4-dioxo-1,4-dihydro-2H-quinazolin-3-yl]-methanesulfonamide;
N-[6-(4-Methoxymethyl-imidazol-1-yl)-7-nitro-2,4-dioxo-1,4-dihydro-2H-quinazolin-3-yl]-methanesulfonamide;
N-(6-Morpholin-4-yl-2,4-dioxo-7-trifluoromethyl-1,4-dihydro-2H-quinazolin-3-yl)-methanesulfonamide;
N-(2,4-Dioxo-6-[1,2,4]triazol-4-yl-7-trifluoromethyl-1,4-dihydro-2H-quinazolin-3-yl)-methanesulfonamide;
Ethanesulfonic acid (2,4-dioxo-6-[1,2,4]triazol-4-yl-7-trifluoromethyl-1,4-dihydro-2H-quinazolin-3-yl)-amide;
1-(3-Methanesulfonylamino-2,4-dioxo-7-trifluoromethyl-1,2,3,4-tetrahydro-quinazolin-6-yl)-1H-[1,2,4]triazole-3-carboxylic acid ethyl ester;
1-(3-Methanesulfonylamino-2,4-dioxo-7-trifluoromethyl-1,2,3,4-tetrahydro-quinazolin-6-yl)-1H-[1,2,4]triazole-3-carboxylic acid methylamide;
N-(6-Imidazol-1-yl-2,4-dioxo-7-trifluoromethyl-1,4-dihydro-2H-quinazolin-3-yl)-methanesulfonamide;
N-(2,4-Dioxo-6-thiomorpholin-4-yl-7-trifluoromethyl-1,4-dihydro-2H-quinazolin-3-yl)-methanesulfonamide;
N-(6-[1,4]Oxazepan-4-yl-2,4-dioxo-7-trifluoromethyl-1,4-dihydro-2H-quinazolin-3-yl)-methanesulfonamide;
N-[6-(4,4-Difluoro-piperidin-1-yl)-2,4-dioxo-7-trifluoromethyl-1,4-dihydro-2H-quinazolin-3-yl-methanesulfonamide;
N-[6-(1,4-Dioxa-8-aza-spiro[4.5]dec-8-yl)-2,4-dioxo-7-trifluoromethyl-1,4-dihydro-2H-quinazolin-3-yl]-methanesulfonamide;
N-[2,4-Dioxo-6-(4-oxo-piperidin-1-yl)-7-trifluoromethyl-1,4-dihydro-2H-quinazolin-3-yl]-methanesulfonamide;
N-(6-Azetidin-1-yl-2,4-dioxo-7-trifluoromethyl-1,4-dihydro-2H-quinazolin-3-yl)-methanesulfonamide;
N-{6-[4-(4-Methoxy-phenyl)-imidazol-1-yl]-2,4-dioxo-7-trifluoromethyl-1,4-dihydro-2H-quinazolin-3-yl}-methanesulfonamide;
N-{6-[4-(4-Methoxymethyl-phenyl)-imidazol-1-yl]-2,4-dioxo-7-trifluoromethyl-1,4-dihydro-2H-quinazolin-3-yl}-methanesulfonamide;
N-[2,4-Dioxo-6-(2-oxo-2H-pyridin-1-yl)-7-trifluoromethyl-1,4-dihydro-2H-quinazolin-3-yl]-methanesulfonamide;
1-(3-methanesulfonylamino-2,4-dioxo-7-trifluoromethyl-1,2,3,4-tetrahydro-quinazolin-6-yl)-1H-imidazole-4-carboxylic acid methyl ester;
1-(3-Methanesulfonylamino-2,4-dioxo-7-trifluoromethyl-1,2,3,4-tetrahydro-quinazolin-6-yl)-1H-imidazole-4-carboxylic acid;
1-(3-Methanesulfonylamino-2,4-dioxo-7-trifluoromethyl-1,2,3,4-tetrahydro-quinazolin-6-yl)-1H-imidazole-4-carboxylic acid dimethylamide;
1-(3-Methanesulfonylamino-2,4-dioxo-7-trifluoromethyl-1,2,3,4-tetrahydro-quinazolin-6-yl)-1H-imidazole-4-carboxylic acid methylamide;
1-(3-Methanesulfonylamino-2,4-dioxo-7-trifluoromethyl-1,2,3,4-tetrahydro-quinazolin-6-yl)-1H-imidazole-4-carboxylic acid amide;
N-[6-(4-Hydroxymethyl-imidazol-1-yl)-2,4-dioxo-7-trifluoromethyl-1,4-dihydro-2H-quinazolin-3-yl]-methanesulfonamide;
N-[6-(4-Cyano-imidazol-1-yl)-2,4-dioxo-7-trifluoromethyl-1,4-dihydro-2H-quinazolin-3-yl]-methanesulfonamide;

N-[6-(4-Bromo-imidazol-1-yl)-2,4-dioxo-7-trifluoromethyl-1,4-dihydro-2H-quinazolin-3-yl]-methanesulfonamide;
N-[6-(4-Trifluoromethyl-imidazol-1-yl)-2,4-dioxo-7-trifluoromethyl-1,4-dihydro-2H-quinazolin-3-yl]-methanesulfonamide;
N-(2,4-Dioxo-6-pyrrol-1-yl-7-trifluoromethyl-1,4-dihydro-2H-quinazolin-3-yl)-methanesulfonamide;
N-[6-(3-Formyl-pyrrol-1-yl)-2,4-dioxo-7-trifluoromethyl-1,4-dihydro-2H-quinazolin-3-yl]-methanesulfonamide;
1-(3-Benzenesulfonylamino-2,4-dioxo-7-trifluoromethyl-1,2,3,4-tetrahydro-quinazolin-6-yl)-1H-imidazole-4-carboxylic acid;
N-[6-(2-Methyl-pyrrol-1-yl)-2,4-dioxo-7-trifluoromethyl-1,4-dihydro-2H-quinazolin-3-yl]-methanesulfonamide;
1-(3-Benzenesulfonylamino-2,4-dioxo-7-trifluoromethyl-1,2,3,4-tetrahydro-quinazolin-6-yl)-1H-imidazole-4-carboxylic acid methyl ester;
Acetic acid 1-(3-methanesulfonylamino-2,4-dioxo-7-trifluoromethyl-1,2,3,4-tetrahydro-quinazolin-6-yl)-1H-pyrrol-3-ylmethyl ester;
N-[6-(3-Hydroxymethyl-pyrrol-1-yl)-2,4-dioxo-7-trifluoromethyl-1,4-dihydro-2H-quinazolin-3-yl]-methanesulfonamide; and
N-[6-(4-Methyl-2-oxo-2,3-dihydro-pyrrol-1-yl)-2,4-dioxo-7-trifluoromethyl-1,4-dihydro-2H-quinazolin-3-yl]-methanesulfonamide.

3. A compound of the formula (I) according to claim 1, wherein said compound is N-(6-Imidazol-1-yl-7-nitro-2,4-dioxo-1,4-dihydro-2H-quinazolin-3-yl)-methanesulfonamide.

4. A compound of the formula (I) according to claim 1, wherein said compound is N-(6-Morpholin-4-yl-2,4-dioxo-7-trifluoromethyl-1,4-dihydro-2H-quinazolin-3-yl)-methanesulfonamide.

5. A compound of the formula (I) according to claim 1, wherein said compound is N-(6-[1,4]Oxazepan-4-yl-2,4-dioxo-7-trifluoromethyl-1,4-dihydro-2H-quinazolin-3-yl)-methanesulfonamide.

6. A compound of the formula (I) according to claim 1, wherein said compound is N-(6-Imidazol-1-yl-2,4-dioxo-7-trifluoromethyl-1,4-dihydro-2H-quinazolin-3-yl)-methanesulfonamide.

\* \* \* \* \*